United States Patent
Stevenson et al.

(10) Patent No.: US 12,371,712 B2
(45) Date of Patent: Jul. 29, 2025

(54) GENETIC DATA COMPRESSION AND METHODS OF USE

(71) Applicant: University of Oregon, Eugene, OR (US)

(72) Inventors: Zachary C. Stevenson, Eugene, OR (US); Stephen A. Banse, Eugene, OR (US); Patrick C. Phillips, Eugene, OR (US)

(73) Assignee: University of Oregon, Eugene, OR (US)

( * ) Notice: Subject to any disclaimer, the term of this patent is extended or adjusted under 35 U.S.C. 154(b) by 468 days.

(21) Appl. No.: 17/236,556

(22) Filed: Apr. 21, 2021

(65) Prior Publication Data

US 2021/0332387 A1    Oct. 28, 2021

Related U.S. Application Data

(60) Provisional application No. 63/013,365, filed on Apr. 21, 2020.

(51) Int. Cl.
*A01K 67/64* (2025.01)
*C12N 15/85* (2006.01)
*C12N 15/90* (2006.01)

(52) U.S. Cl.
CPC ............ *C12N 15/902* (2013.01); *A01K 67/64* (2025.01); *C12N 15/8509* (2013.01); *A01K 2227/703* (2013.01); *C12N 2310/20* (2017.05); *C12N 2800/80* (2013.01)

(58) Field of Classification Search
None
See application file for complete search history.

(56) References Cited

U.S. PATENT DOCUMENTS

| | | | |
|---|---|---|---|
| 2016/0122748 | A1 | 5/2016 | St. Onge et al. |
| 2018/0298377 | A1 | 10/2018 | Levy et al. |

OTHER PUBLICATIONS

Gaidukov, L., Wroblewska, L., Teague, B., Nelson, T., Zhang, X., Liu, Y., . . . & Weiss, R. (2018). A multi-landing pad DNA integration platform for mammalian cell engineering. Nucleic acids research, 46(8), 4072-4086 and Supplemental. (Year: 2018).*
Kanca, O., Zirin, J., Garcia-Marques, J., Knight, S. M., Yang-Zhou, D., Amador, G., . . . & Bellen, H. J. (2019). An efficient CRISPR-based strategy to insert small and large fragments of DNA using short homology arms. Elife, 8, e51539. (Year: 2019).*
Daniel J Dickinson, Bob Goldstein, CRISPR-Based Methods for Caenorhabditis elegans Genome Engineering, Genetics, vol. 202, Issue 3, Mar. 1, 2016, pp. 885-901, (Year: 2016).*
Levy et al., "Quantitative evolutionary dynamics using high-resolution lineage tracking," *Nature*, vol. 519, No. 7542, pp. 181-186, 2015 (Author manuscript version, 17 pages).
Stevenson et al., "Rapid self-selecting and clone free integration of transgenes into engineered CRISPR safe harbor locations in *C. elegans*," *Genome Engineering: Frontiers of CRISPR-Cas*, Cold Spring Harbor Laboratory, Oct. 10-13, 2019 (1 page).
Stevenson, "Quantifying the Evolutionary Trajectories of Novel Mutations using High-Resolution Lineage Tracking in *Caenorhabditis elegans*," Presentation at University of Oregon, Mar. 19, 2019 (65 pages).

* cited by examiner

*Primary Examiner* — Brian Whiteman
*Assistant Examiner* — Khaleda B Hasan
(74) *Attorney, Agent, or Firm* — Klarquist Sparkman, LLP

(57) ABSTRACT

Provided herein are genetically modified cells and methods of their production, wherein such methods include introducing a nucleic acid molecule including a plurality of index sequences into a cell comprising a synthetic landing pad, wherein each of the plurality of index sequences includes a first portion of a sequence and the synthetic landing pad includes a second portion of the sequence. The method further includes generating a plurality of cells that include the synthetic landing pad and the nucleic acid molecule including the plurality of index sequences and integrating one of the plurality of index sequences into the synthetic landing pad in each of the cells, thereby linking the first and second portions of the sequence. The linked first and second portions of the sequence result in a functional gene and cells including the integrated index sequence are selected based on presence or activity of the functional gene.

15 Claims, 12 Drawing Sheets

Specification includes a Sequence Listing.

FIG. 1A
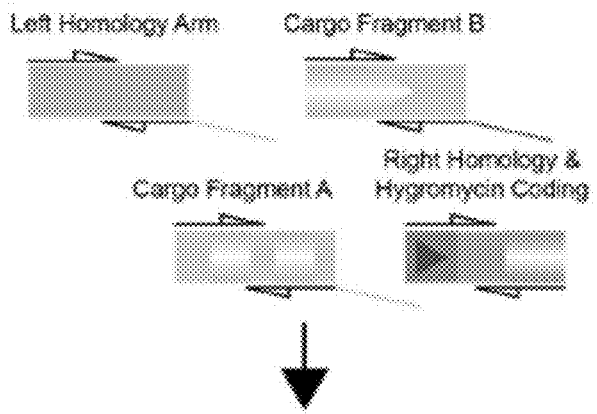
FIG. 1B Optional PCR complexing of fragments
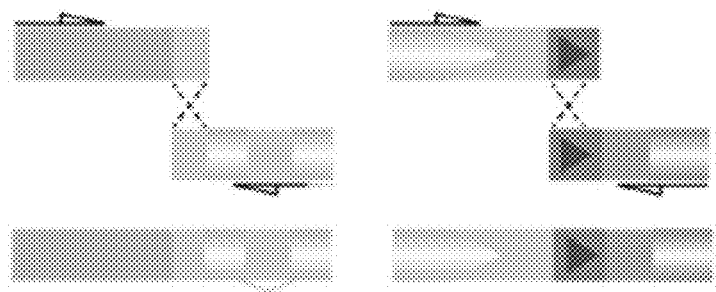
Fragments are injected into the C. elegans gonad which recognizes microhomology and assembles the donor homology for integration
FIG. 1C
FIG. 1D
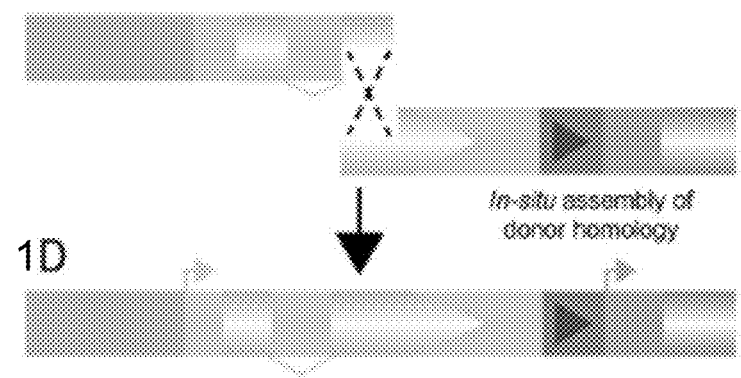
Donor homology is ready for integration

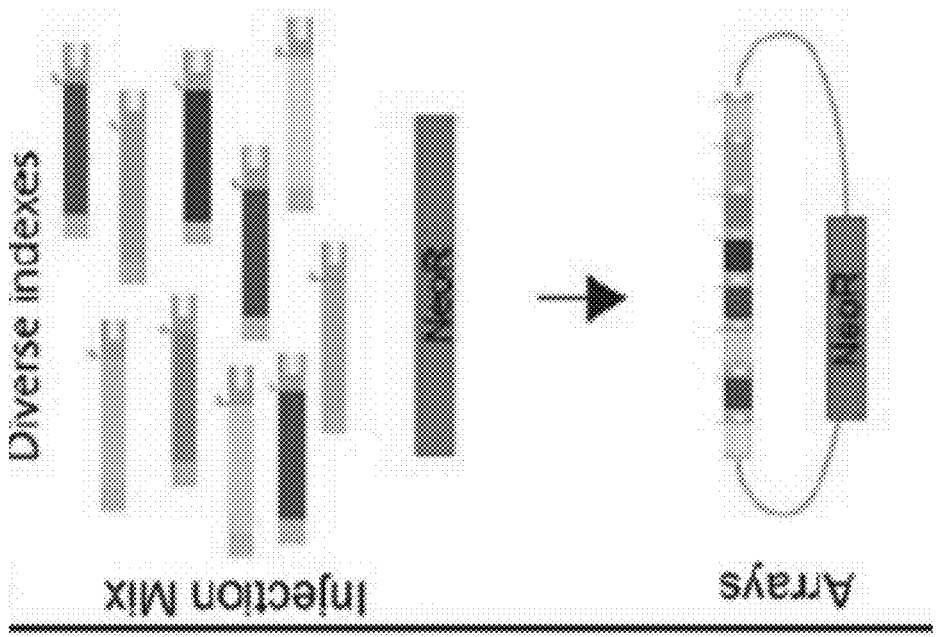
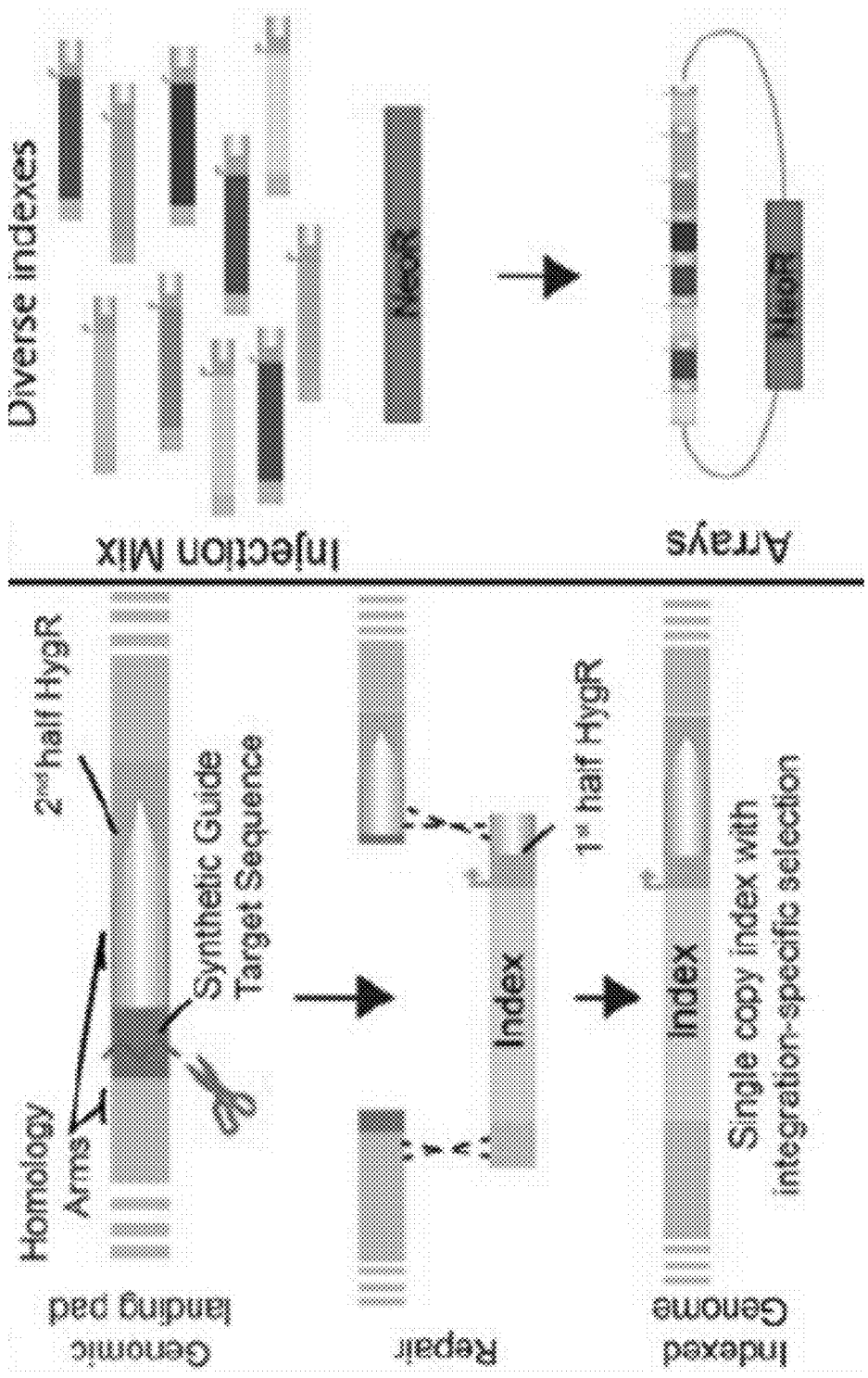
FIG. 3A
FIG. 3B

SEQUENCE LISTING

```
<160> NUMBER OF SEQ ID NOS: 61

<210> SEQ ID NO 1
<211> LENGTH: 79
<212> TYPE: DNA
<213> ORGANISM: Artificial Sequence
<220> FEATURE:
<223> OTHER INFORMATION: Amplification template oligonucleotide ZCS133
<220> FEATURE:
<221> NAME/KEY: misc_feature
<222> LOCATION: (34)..(48)
<223> OTHER INFORMATION: n is a, c, g, or t

<400> SEQUENCE: 1
ccgacggatt ctacaaggta agtttaaaca tatnnnnnnn nnnnnnnnta tttaaatttt      60
caggaccgtt acgtctacc                                                   79

<210> SEQ ID NO 2
<211> LENGTH: 59
<212> TYPE: DNA
<213> ORGANISM: Artificial Sequence
<220> FEATURE:
<223> OTHER INFORMATION: Oligonucleotide primer ZCS134, a forward primer
      used to amplify off of the template ZCS133.  It also provides
      additional sequence to add 35 bases of homology to the genome on
      the left hand side, while providing the intron/exon boundary for
      restoration of Hyg

<400> SEQUENCE: 2
gatacgtcct ccgtgtcaac tcctgcgccg acggattcta caaggtaagt ttaaacata      59

<210> SEQ ID NO 3
<211> LENGTH: 59
<212> TYPE: DNA
<213> ORGANISM: Artificial Sequence
<220> FEATURE:
<223> OTHER INFORMATION: Oligonucleotide primer ZCS135, a reverse primer
      used to amplify off of the template ZCS133.  Also provides
      additional sequence to add 35 bases of homology to the genome on
      the right hand side, while providing the intron/exon boundary for
      restoration of Hyg
```

```
<400> SEQUENCE: 3
attgggaggg cggcggaggc gaagtgacgg tagacgtaac ggtcctgaaa atttaaata      59

<210> SEQ ID NO 4
<211> LENGTH: 17
<212> TYPE: DNA
<213> ORGANISM: Artificial Sequence
<220> FEATURE:
<223> OTHER INFORMATION: Oligonucleotide primer ZCS273, a forward primer
      used to amplify off of a standard Hygromycin template to provide
      500 bases of homology to the genome on the left hand side.

<400> SEQUENCE: 4
cgcgtctctt ccgtgcg                                                    17

<210> SEQ ID NO 5
<211> LENGTH: 16
<212> TYPE: DNA
<213> ORGANISM: Artificial Sequence
<220> FEATURE:
<223> OTHER INFORMATION: Oligonucleotide primer ZCS275, a reverse primer
      used to amplify off of a standard Hygromycin template to provide
      500 bases of homology to the genome on the left hand side

<400> SEQUENCE: 5
cgtcggcgca ggagtt                                                     16

<210> SEQ ID NO 6
<211> LENGTH: 21
<212> TYPE: DNA
<213> ORGANISM: Artificial Sequence
<220> FEATURE:
<223> OTHER INFORMATION: Oligonucleotide primer ZCS276, a forward primer
      used to amplify off of a standard Hygromycin template to provide
      500 bases of homology to the genome on the right hand side.

<400> SEQUENCE: 6
gtctaccgtc acttcgcctc c                                               21

<210> SEQ ID NO 7
<211> LENGTH: 22
<212> TYPE: DNA
<213> ORGANISM: Artificial Sequence
<220> FEATURE:
<223> OTHER INFORMATION: Oligonucleotide primer ZCS278, a reverse primer
      used to amplify off of a standard Hygromycin template to provide
      500 bases of homology to the genome on the right hand side

<400> SEQUENCE: 7
gacctcgtat tgggagtctc cg                                              22

<210> SEQ ID NO 8
<211> LENGTH: 23
<212> TYPE: DNA
<213> ORGANISM: Artificial Sequence
<220> FEATURE:
<223> OTHER INFORMATION: Primer oligonucleotide ZCS149

<400> SEQUENCE: 8
gggatcctct agagtcgacc tgc                                             23

<210> SEQ ID NO 9
<211> LENGTH: 22
<212> TYPE: DNA
<213> ORGANISM: Artificial Sequence
<220> FEATURE:
<223> OTHER INFORMATION: Primer oligonucleotide ZCS150
```

```
<400> SEQUENCE: 9
cgggtaccga gctcgaattc ac                                              22

<210> SEQ ID NO 10
<211> LENGTH: 55
<212> TYPE: DNA
<213> ORGANISM: Artificial Sequence
<220> FEATURE:
<223> OTHER INFORMATION: Primer oligonucleotide ZCS139

<400> SEQUENCE: 10
tgagaatgga agatagacaa tcgagggcag cctcggagat aagcttttgc tctcc          55

<210> SEQ ID NO 11
<211> LENGTH: 27
<212> TYPE: DNA
<213> ORGANISM: Artificial Sequence
<220> FEATURE:
<223> OTHER INFORMATION: Primer oligonucleotide ZCS138

<400> SEQUENCE: 11
ctgccctcga ttgtctatct tccattc                                         27

<210> SEQ ID NO 12
<211> LENGTH: 34
<212> TYPE: DNA
<213> ORGANISM: Artificial Sequence
<220> FEATURE:
<223> OTHER INFORMATION: Primer oligonucleotide ZCS140

<400> SEQUENCE: 12
cggtcttctg tataactaca aaaagaata aaaa                                  34

<210> SEQ ID NO 13
<211> LENGTH: 59
<212> TYPE: DNA
<213> ORGANISM: Artificial Sequence
<220> FEATURE:
<223> OTHER INFORMATION: Primer oligonucleotide ZCS145

<400> SEQUENCE: 13
aagtttaaaa taacttcgta tagcatacat tatacgaagt tattttcagg gagagcaaa      59

<210> SEQ ID NO 14
<211> LENGTH: 58
<212> TYPE: DNA
<213> ORGANISM: Artificial Sequence
<220> FEATURE:
<223> OTHER INFORMATION: Primer oligonucleotide ZCS141

<400> SEQUENCE: 14 tattctttt tgtagttata cagaagaccg attttttgctt tcgtcgtaaa tctacaca       58

<210> SEQ ID NO 15
<211> LENGTH: 17
<212> TYPE: DNA
<213> ORGANISM: Artificial Sequence
<220> FEATURE:
<223> OTHER INFORMATION: Primer oligonucleotide ZCS154

<400> SEQUENCE: 15
cgtcggcgca ggagttg                                                    17

<210> SEQ ID NO 16
```

```
<211> LENGTH: 50
<212> TYPE: DNA
<213> ORGANISM: Artificial Sequence
<220> FEATURE:
<223> OTHER INFORMATION: Primer oligonucleotide ZCS155

<400> SEQUENCE: 16
acgtcctccg tgtcaactcc tgcgccgacg gtctaccgtc acttcgcctc            50

<210> SEQ ID NO 17
<211> LENGTH: 59
<212> TYPE: DNA
<213> ORGANISM: Artificial Sequence
<220> FEATURE:
<223> OTHER INFORMATION: Primer oligonucleotide ZCS144

<400> SEQUENCE: 17
tgtatgctat acgaagttat tttaaactta ctaaaaattg cggtcataaa ctgaaacgt  59

<210> SEQ ID NO 18
<211> LENGTH: 52
<212> TYPE: DNA
<213> ORGANISM: Artificial Sequence
<220> FEATURE:
<223> OTHER INFORMATION: Primer oligonucleotide ZCS164

<400> SEQUENCE: 18
catgcctgca ggtcgactct agaggatccc actggccgtc gttttacaat tt          52

<210> SEQ ID NO 19
<211> LENGTH: 59
<212> TYPE: DNA
<213> ORGANISM: Artificial Sequence
<220> FEATURE:
<223> OTHER INFORMATION: Primer oligonucleotide ZCS165

<400> SEQUENCE: 19
gacggccagt gaattcgagc tcggtacccg aaacagttat gtttggtata ttgggaatg  59

<210> SEQ ID NO 20
<211> LENGTH: 200
<212> TYPE: DNA
<213> ORGANISM: Artificial Sequence
<220> FEATURE:
<223> OTHER INFORMATION: Primer oligonucleotide ZCS357
<220> FEATURE:
<221> NAME/KEY: misc_feature
<222> LOCATION: (94)..(108)
<223> OTHER INFORMATION: n is a, c, g, or t

<400> SEQUENCE: 20
actcctgcgc cgacggattc tacaaggtaa gtttaaacat atgcccgggc gagtcataat  60
acactctttc cctacacgac gctcttccga tctnnnnnnn nnnnnnnag atcggaagag  120 cacacgtctg aactccagtc acattatgac tcgcccgggc tatttaaatt ttcaggaccg  180
ttacgtctac cgtcacttcg                                              200

<210> SEQ ID NO 21
<211> LENGTH: 18
<212> TYPE: DNA
<213> ORGANISM: Artificial Sequence
<220> FEATURE:
<223> OTHER INFORMATION: Primer oligonucleotide ZCS286

<400> SEQUENCE: 21
gaggacggct gggagctc                                                18
```

<210> SEQ ID NO 22
<211> LENGTH: 21
<212> TYPE: DNA
<213> ORGANISM: Artificial Sequence
<220> FEATURE:
<223> OTHER INFORMATION: Primer oligonucleotide ZCS285

<400> SEQUENCE: 22
tgaccgccac atccgtagag a                                             21

<210> SEQ ID NO 23
<211> LENGTH: 60
<212> TYPE: DNA
<213> ORGANISM: Artificial Sequence
<220> FEATURE:
<223> OTHER INFORMATION: Primer oligonucleotide ZCS287
<220> FEATURE:
<221> NAME/KEY: misc_feature
<222> LOCATION: (34)..(37)
<223> OTHER INFORMATION: n is a, c, g, or t

<400> SEQUENCE: 23
acactctttc cctacacgac gctcttccga tctnnnncta caaggtaagt ttaaacatat    60

<210> SEQ ID NO 24
<211> LENGTH: 57
<212> TYPE: DNA
<213> ORGANISM: Artificial Sequence
<220> FEATURE:
<223> OTHER INFORMATION: Primer oligonucleotide ZCS288
<220> FEATURE:
<221> NAME/KEY: misc_feature
<222> LOCATION: (33)..(36)
<223> OTHER INFORMATION: n is a, c, g, or t

<400> SEQUENCE: 24
gactggagtt cagacgtgtg ctcttccgat ctnnnnacgg tcctgaaaat ttaaata      57

<210> SEQ ID NO 25
<211> LENGTH: 52
<212> TYPE: DNA
<213> ORGANISM: Artificial Sequence
<220> FEATURE:
<223> OTHER INFORMATION: Primer oligonucleotide ZCS304
<220> FEATURE:
<221> NAME/KEY: misc_feature
<222> LOCATION: (21)..(28)
<223> OTHER INFORMATION: n is a, c, g, or t

<400> SEQUENCE: 25
cgctagcacg tcaatcagtc nnnnnnnngt aacggtcctg aaaatttaaa ta           52

<210> SEQ ID NO 26
<211> LENGTH: 18
<212> TYPE: DNA
<213> ORGANISM: Artificial Sequence
<220> FEATURE:
<223> OTHER INFORMATION: Primer oligonucleotide ZCS305

<400> SEQUENCE: 26
ttctcagttg tgatacgg                                                 18

<210> SEQ ID NO 27
<211> LENGTH: 69
<212> TYPE: DNA
<213> ORGANISM: Artificial Sequence
<220> FEATURE:

```
<223> OTHER INFORMATION: Primer oligonucleotide ZCS306
<220> FEATURE:
<221> NAME/KEY: misc_feature
<222> LOCATION: (34)..(37)
<223> OTHER INFORMATION: n is a, c, g, or t

<400> SEQUENCE: 27
acactctttc cctacacgac gctcttccga tctnnnncga cggattctac aaggtaagtt      60
taaacatat                                                              69

<210> SEQ ID NO 28
<211> LENGTH: 56
<212> TYPE: DNA
<213> ORGANISM: Artificial Sequence
<220> FEATURE:
<223> OTHER INFORMATION: Primer oligonucleotide ZCS307
<220> FEATURE:
<221> NAME/KEY: misc_feature
<222> LOCATION: (33)..(36)
<223> OTHER INFORMATION: n is a, c, g, or t

<400> SEQUENCE: 28
gactggagtt cagacgtgtg ctcttccgat ctnnnncgct agcacgtcaa tcagtc          56

<210> SEQ ID NO 29
<211> LENGTH: 20
<212> TYPE: DNA
<213> ORGANISM: Artificial Sequence
<220> FEATURE:
<223> OTHER INFORMATION: Primer oligonucleotide MS376

<400> SEQUENCE: 29
cgtctgctgc tccatacaag                                                  20

<210> SEQ ID NO 30
<211> LENGTH: 26
<212> TYPE: DNA
<213> ORGANISM: Artificial Sequence
<220> FEATURE:
<223> OTHER INFORMATION: Primer oligonucleotide MS248

<400> SEQUENCE: 30
cagccaaatt cgttgactga gtattc                                           26

<210> SEQ ID NO 31
<211> LENGTH: 19
<212> TYPE: DNA
<213> ORGANISM: Artificial Sequence
<220> FEATURE:
<223> OTHER INFORMATION: Primer oligonucleotide ZCS84

<400> SEQUENCE: 31
gatagacaat cgagggcag                                                   19

<210> SEQ ID NO 32
<211> LENGTH: 21
<212> TYPE: DNA
<213> ORGANISM: Artificial Sequence
<220> FEATURE:
<223> OTHER INFORMATION: Primer oligonucleotide MS121

<400> SEQUENCE: 32
caggaaacag ctatgaccat g                                                21

<210> SEQ ID NO 33
<211> LENGTH: 332
```

```
<212> TYPE: DNA
<213> ORGANISM: Artificial Sequence
<220> FEATURE:
<223> OTHER INFORMATION: tbb-2 3'UTR

<400> SEQUENCE: 33
gataaatgca aaatcctttc aagcattccc ttcttctcta tcactcttct ttcttttgt    60 caaaaaattc tctcgctaat ttatttgctt ttttaatgtt attattttat gactttttat   120
agtcactgaa aagtttgcat ctgagtgaag tgaatgctat caaaatgtga ttctgtctga   180
tgtactttca caatctctct tcaattccat tttgaagtgc tttaaacccg aaaggttgag   240
aaaaatgcga gcgctcaaat atttgtattg tgttcgttga gtgacccaac aaaaagagga   300
aactttattg tgccgccaag aaaaaagtct ca                                 332

<210> SEQ ID NO 34
<211> LENGTH: 350
<212> TYPE: DNA
<213> ORGANISM: Artificial Sequence
<220> FEATURE:
<223> OTHER INFORMATION: U6 promoter

<400> SEQUENCE: 34
caaaaaaaac tagcaataaa ggaataaaaa actgtacacc ttaaaggcgc acactctgtt    60
ttgcaaattt tattttagt tgtgaatttt ctgctgagac ctgaaaatag caactttagt    120
actactataa tttgtcaacc ttttcaaaaa aagcatgcaa ttttttgagaa actcttataa   180 aagctattat taaaaaaaca cctttttccc aaaattattc cacaaaaaat atgttatgaa   240
atgcctacac cctctcacac acactcttta tactactctg tcaaactcac gagatgtctg   300
ccgcctcttg tgttgcccct atataaacac ctcctattgc gagatgtctt              350

<210> SEQ ID NO 35
<211> LENGTH: 80
<212> TYPE: DNA
<213> ORGANISM: Artificial Sequence
<220> FEATURE:
<223> OTHER INFORMATION: gRNA scaffold from pDD162

<400> SEQUENCE: 35
gttttagagc tagaaatagc aagttaaaat aaggctagtc cgttatcaac ttgaaaaagt    60
ggcaccgagt cggtgctttt                                                80

<210> SEQ ID NO 36
<211> LENGTH: 3273
<212> TYPE: DNA
<213> ORGANISM: Artificial Sequence
<220> FEATURE:
<223> OTHER INFORMATION: U6::guideRNA plasmid pZCS41

<400> SEQUENCE: 36
aacactgcgg ccaacttact tctgacaacg atcggaggac cgaaggagct aaccgctttt    60
ttgcacaaca tggggatca tgtaactcgc cttgatcgtt gggaaccgga gctgaatgaa    120
gccataccaa acgacgagcg tgacaccacg atgcctgtag caatggcaac aacgttgcgc   180
aaactattaa ctggcgaact acttactcta gcttcccggc aacaattaat agactggatg   240
gaggcggata agttgcagg accacttctg cgctcggccc ttccggctgg ctggtttatt   300
gctgataaat ctggagccgg tgagcgtggg tctcgcggta tcattgcagc actggggcca   360
gatggtaagc cctcccgtat cgtagttatc tacacgacgg ggagtcaggc aactatggat   420
```

```
gaacgaaata gacagatcgc tgagataggt gcctcactga ttaagcattg gtaactgtca    480
gaccaagttt actcatatat actttagatt gatttaaaac ttcatttttta atttaaaagg    540 atctaggtga agatccttt tgataatctc atgaccaaaa tcccttaacg tgagttttcg    600
ttccactgag cgtcagaccc cgtagaaaag atcaaaggat cttcttgaga tccttttttt    660
ctgcgcgtaa tctgctgctt gcaaacaaaa aaaccaccgc taccagcggt ggtttgtttg    720
ccggatcaag agctaccaac tcttttttccg aaggtaactg gcttcagcag agcgcagata    780
ccaaatactg ttcttctagt gtagccgtag ttaggccacc acttcaagaa ctctgtagca    840
ccgcctacat acctcgctct gctaatcctg ttaccagtgg ctgctgccag tggcgataag    900
tcgtgtctta ccgggttgga ctcaagacga tagttaccgg ataaggcgca gcggtcgggc    960
tgaacggggg gttcgtgcac acagcccagc ttggagcgaa cgacctacac cgaactgaga   1020
tacctacagc gtgagctatg agaaagcgcc acgcttcccg aagggagaaa ggcggacagg   1080
tatccggtaa cgcggcaggg tcggaacagga gagcgcacga gggagcttcc agggggaaac   1140
gcctggtatc tttatagtcc tgtcgggttt cgccacctct gacttgagcg tcgatttttg   1200
tgatgctcgt caggggggcg gagcctatgg aaaaacgcca gcaacgcggc cttttttacgg   1260 ttcctggcct tttgctggcc ttttgctcac atgttctttc ctgcgttatc ccctgattct   1320
gtggataacc gtattaccgc ctttgagtga gctgataccg ctcgccgcag ccgaacgacc   1380
gagcgcagcg agtcagtgag cgaggaagcg gaagagcgcc caatacgcaa accgcctctc   1440
cccgcgcgtt ggccgattca ttaatgcagc tggcacgaca ggtttcccga ctggaaagcg   1500
ggcagtgagc gcaacgcaat taatgtgagt tagctcactc attaggcacc ccaggcttta   1560
cactttatgc ttccggctcg tatgttgtgt ggaattgtga gcggataaca atttcacaca   1620
ggaaacagct atgaccatga ttacgccaag cttgcatgcc tgcaggtcga ctctagagga   1680
tcccattata catagttgat aattcactgg ccgtcgtttt acaacgtcgt gactgggaaa   1740
accaaaaaaa actagcaata aaggaataaa aaactgtaca ccttaaaggc gcacactctg   1800
ttttgcaaat tttatttta gttgtgaatt ttctgctgag acctgaaaat agcaactta    1860 gtactactat aatttgtcaa cctttttcaaa aaaagcatgc aatttttgag aaactcttat   1920
aaaagctatt attaaaaaaa cacctttttt ccaaaattat tccacaaaaa atatgttatg   1980
aaatgcctac accctctcac acacactctt tatactactc tgtcaaactc acgagatgtc   2040
tgccgcctct tgtgttgccc ctatataaac acctcctatt gcgagatgtc ttggcgaagt   2100
gacggtagac cgtgttttag agctagaaat agcaagttaa aataaggcta gtccgttatc   2160
aacttgaaaa agtggcaccg agtcggtgct ttttgtgaaa tttctggcgt aatagcgaag   2220
aggcccgcac cgatcgccct tcccaacagt tgcgcagcct gaatggcgaa tcgggtaccg   2280
agctcgaatt cactggccgt cgttttacaa cgtcgtgact gggaaaaccc tggcgttacc   2340
caacttaatc gccttgcagc acatccccct ttcgccagct ggcgtaatag cgaagaggcc   2400
cgcaccgatc gcccttccca cagttgcgc agcctgaatg cgaatggcg cctgatgcgg   2460 tatttttctcc ttacgcatct gtgcggtatt tcacaccgca tatggtgcac tctcagtaca   2520
atctgctctg atgccgcata gttaagccag ccccgacacc cgccaacacc cgctgacgcg   2580
ccctgacggg cttgtctgct cccggcatcc gcttacagac aagctgtgac cgtctccggg   2640
agctgcatgt gtcagaggtt ttcaccgtca tcaccgaaac gcgcgagacg aaagggcctc   2700
gtgatacgcc tatttttata ggttaatgtc atgataataa tggtttctta cgtcaggt    2760 ggcactttc ggggaaatgt gcgcggaacc cctatttgtt tatttttcta aatacattca    2820
```

-continued

```
aatatgtatc cgctcatgag acaataaccc tgataaatgc ttcaataata ttgaaaaagg      2880
aagagtatga gtattcaaca tttccgtgtc gcccttattc cctttttgc ggcatttgc        2940 cttcctgttt ttgctcaccc agaaacgctg gtgaaagtaa aagatgctga agatcagttg     3000
ggtgcacgag tgggttacat cgaactggat ctcaacagcg gtaagatcct tgagagtttt    3060
cgccccgaag aacgttttcc aatgatgagc acttttaaag ttctgctatg tggcgcggta     3120
ttatcccgta ttgacgccgg gcaagagcaa ctcggtcgcc gcatacacta ttctcagaat     3180
gacttggttg agtactcacc agtcacagaa aagcatctta cggatggcat gacagtaaga    3240
gaattatgca gtgctgccat aaccatgagt gat                                  3273
```

<210> SEQ ID NO 37
<211> LENGTH: 20
<212> TYPE: DNA
<213> ORGANISM: Artificial Sequence
<220> FEATURE:
<223> OTHER INFORMATION: Site-specific nuclease recognition site

<400> SEQUENCE: 37
gcgaagtgac ggtagaccgt                                                 20

<210> SEQ ID NO 38
<211> LENGTH: 20
<212> TYPE: DNA
<213> ORGANISM: Artificial Sequence
<220> FEATURE:
<223> OTHER INFORMATION: gRNA targeting GT300 synthetic site

<400> SEQUENCE: 38
ggacagtcct gccgaggtgg                                                 20

<210> SEQ ID NO 39
<211> LENGTH: 1203
<212> TYPE: DNA
<213> ORGANISM: Artificial Sequence
<220> FEATURE:
<223> OTHER INFORMATION: HYGR?3'::unc-54 3' UTR
<220> FEATURE:
<221> NAME/KEY: misc_feature
<222> LOCATION: (1)..(1)
<223> OTHER INFORMATION: Last base of Cas9 PAM sequence
<220> FEATURE:
<221> NAME/KEY: misc_feature
<222> LOCATION: (2)..(850)
<223> OTHER INFORMATION: HYGRdelta3'
<220> FEATURE:
<221> NAME/KEY: misc_feature
<222> LOCATION: (851)..(1203)
<223> OTHER INFORMATION: unc-54 3'UTR

<400> SEQUENCE: 39

```
ggaccgttac gtctaccgtc acttcgcctc cgccgccctc ccaatcccag aggtcctcga     60
catcggagag ttctccgagt ccctcaccta ctgcatctcc cgtcgtgccc aaggagtcac   120
cctccaagac ctcccagaga ccgagctccc agccgtcctc caaccagtcg ccgaggccat  180
ggacgccatc gccgccgccg acctctccca aacctccgga ttcggaccat tcggaccaca  240
aggaatcgga caatacacca cctggcgtga cttcatctgc gccatcgccg acccacacgt  300
ctaccactgg caaaccgtca tggacgacac cgtctccgcc tcgtcgccc aagccctcga   360 cgagctcatg ctctgggccg aggactgcc agaggtccgt cacctcgtcc acgccgactt   420
cggatccaac aacgtcctca ccgacaacgg acgtatcacc gccgtcatcg actggtccga   480
```

-continued

```
ggccatgttc ggagactccc aatacgaggt cgccaacatc ttcttctggc gtccatggct    540
cgcctgcatg gagcaacaaa cccgttactt cgagcgtcgt cacccagagc tcgccggatc    600
cccacgtctc cgtgcctaca tgctccgtat cggactcgac caactctacc aatccctcgt    660
cgacggaaac ttcgacgacg ccgcctgggc ccaaggacgt tgcgacgcca tcgtccgttc    720
cggagccgga accgtcggac gtacccaaat cgcccgtcgt tccgccgccg tctggaccga    780
cggatgcgtc gaggtcctcg ccgactccgg aaaccgtcgt ccatccaccc gtccacgtgc    840
caaggagtaa gtccaattac tcttcaacat ccctacatgc tctttctccc tgtgctccca    900
cccctatttt tgttattat caaaaaactt ctcttaattt ctttgttttt tagcttcttt     960
taagtcacct ctaacaatga aattgtgtag attcaaaaat agaattaatt cgtaataaaa   1020
agtcgaaaaa aattgtgctc cctcccccca ttaataataa ttctatccca aaatctacac   1080
aatgttctgt gtacacttct tatgtttttt acttctgata aattttttg aaacatcata   1140 gaaaaaccg cacacaaaat accttatcat atgttacgtt tcagtttatg accgcaattt   1200
tta                                                                 1203
```

<210> SEQ ID NO 40
<211> LENGTH: 608
<212> TYPE: DNA
<213> ORGANISM: Artificial Sequence
<220> FEATURE:
<223> OTHER INFORMATION: eft-3p

<400> SEQUENCE: 40

```
gcacctttgg tcttttattg tcaacttcca ttggttcttc cattgtttct gttaaattaa     60 tgaattttc ataaaataaa gacattatac aatataaaaa tgaagaattt attgaaaata    120
aactgccaga gagaaaaagt atgcaacact cccgccgaga gtgtttgaaa tggtgtacgg    180
tacattttcg tgctaggagt tagatgtgca ggcagcaacg agaggggag agatttttt     240 gggccttgtg aaattaacgt gagttttctg gtcatctgac taatcatgtt ggttttttgt    300
tggtttattt tgtttttatc tttgttttta tccagattag gaaatttaaa ttttatgaat    360
ttataatgag gtcaaacatt cagtcccagc gtttttcctg ttctcactgt ttagtcgaat    420
tttattttta ggctttcaac aaatgttcta actgtcttat ttgtgacctc acttttata     480 tttttttaat tttaaaaat attagaagtt tctaggataa ttttttcgac ttttattctc    540
tctaccgtcc gcactcttct tacttttaaa ttaaattgtt tttttttcag ttgggaaaca    600
ctttgctc                                                             608
```

<210> SEQ ID NO 41
<211> LENGTH: 696
<212> TYPE: DNA
<213> ORGANISM: Artificial Sequence
<220> FEATURE:
<223> OTHER INFORMATION: wrmScarlet

<400> SEQUENCE: 41

```
atggtcagca agggagaggc agttatcaag gagttcatgc gtttcaaggt ccacatggag     60
ggatccatga acggacacga gttcgagatc gaggagaggg agagggacg tccatacgag    120 gaacccaaa ccgccaagct caaggtcacc aagggaggac cactcccatt ctcctgggac    180
atcctctccc cacaattcat gtacggatcc cgtgccttca ccaagcaccc agccgacatc    240
ccagactact acaagcaatc cttcccagag ggattcaagt gggagcgtgt catgaacttc    300
gaggacggag gagccgtcac cgtcacccaa gacacctccc tcgaggacgg aaccctcatc    360
```

```
tacaaggtca agctccgtgg aaccaacttc ccaccagacg gaccagtcat gcaaaagaag      420
accatgggat gggaggcctc caccgagcgt ctctacccag aggacggagt cctcaaggga      480
gacatcaaga tggccctccg tctcaaggac ggaggacgtt acctcgccga cttcaagacc      540
acctacaagg ccaagaagcc agtccaaatg ccaggagcct acaacgtcga ccgtaagctc      600
gacatcacct cccacaacga ggactacacc gtcgtcgagc aatacgagcg ttccgaggga      660
cgtcactcca ccggaggaat ggacgagctc tacaag                               696

<210> SEQ ID NO 42
<211> LENGTH: 19
<212> TYPE: DNA
<213> ORGANISM: Artificial Sequence
<220> FEATURE:
<223> OTHER INFORMATION: gRNA from pMS79, targeting PX696 landing pad

<400> SEQUENCE: 42
gacagtcctg ccgaggtgg                                                  19

<210> SEQ ID NO 43
<211> LENGTH: 2085
<212> TYPE: DNA
<213> ORGANISM: Artificial Sequence
<220> FEATURE:
<223> OTHER INFORMATION: PX696 landing pad
<220> FEATURE:
<221> NAME/KEY: misc_feature
<222> LOCATION: (1)..(783)
<223> OTHER INFORMATION: Left homology arm, corresponding to F14E5.8 in
      Caenorhabditis elegans genome
<220> FEATURE:
<221> NAME/KEY: misc_feature
<222> LOCATION: (784)..(806)
<223> OTHER INFORMATION: sgRNA target 5 (SG5)
<220> FEATURE:
<221> NAME/KEY: misc_feature
<222> LOCATION: (807)..(1655)
<223> OTHER INFORMATION: unc-54 3'UTR
<220> FEATURE:
<221> NAME/KEY: misc_feature
<222> LOCATION: (2009)..(2033)
<223> OTHER INFORMATION: Downstream loxP site
<220> FEATURE:
<221> NAME/KEY: misc_feature
<222> LOCATION: (2034)..(2067)
<223> OTHER INFORMATION: loxP site
<220> FEATURE:
<221> NAME/KEY: misc_feature
<222> LOCATION: (2068)..(2085)
<223> OTHER INFORMATION: Spacer sequence

<400> SEQUENCE: 43
cactcgttta ggctattccc ctattttttga tattccttcg cacatatgaa aactactttt     60
tttcgaaact gttaactcca gaatttataa atctatagcc cttacttgat tatttattat     120
catggttact cacctcatgt ctctttctct tttcaagaag tcttcgttca tatctgttgt     180
ctctttcctc cttttgaatc tctgctttgc tcttcgccat tgtttcctga aaataatgta     240
acttgaattg tgtaatatac tttttttaatt tgaatttggc ttgtaacgcg gaatcactac     300
gtgcgggatc atttcttact agaaaaccca gaaaatgcca tatttcactt atctcggggt     360
catttctaat tagaaaagct acaaaaacca tttctaatta cggtgacttt agaactggtc     420
gaaatagcta attagaaatg ggttttttgct aattagaggt gactctatgt tatctgagta     480
agcctcgttt gtatgtaaac tcacagtact aataaatgca agacaccggg tttgtctag      540 atatgaaata attgaaatat caattctgac agacaataat ggtaatcttg ataaggagtt     600
```

```
ccacgcccag gagaacacgt tagtttctt gttttgatt gcgtgcgtta ttttggagaa    660
aaactcgatt tttacaaaa taattttttg aaaggaacac tgttcaataa gttttgtctt    720
ttttctcagt tgtgatacgg ttttttattc tttttgtag ttatacagaa gaccgcctgc    780
aggggacagt cctgccgagg tggagggacc gttacgtcta ccgtcacttc gcctccgccg    840
ccctcccaat cccagaggtc ctcgacatcg agagttctc cgagtccctc acctactgca    900
tctcccgtcg tgcccaagga gtcaccctcc aagacctccc agagaccgag ctcccagccg    960
tcctccaacc agtcgccgag gccatggacg ccatcgccgc cgccgacctc tcccaaacct   1020
ccggattcgg accattcgga ccacaaggaa tcggacaata caccacctgg cgtgacttca   1080
tctgcgccat cgccgaccca cacgtctacc actggcaaac cgtcatggac gacaccgtct   1140
ccgcctccgt cgcccaagcc ctcgacgagc tcatgctctg ggccgaggac tgcccagagg   1200
tccgtcacct cgtccacgcc gacttcggat ccaacaacgt cctcaccgac aacggacgta   1260
tcaccgccgt catcgactgg tccgaggcca tgttcggaga ctcccaatac gaggtcgcca   1320
acatcttctt ctggcgtcca tggctcgcct gcatggagca acaaacccgt tacttcgagc   1380
gtcgtcaccc agagctcgcc ggatccccac gtctccgtgc ctacatgctc cgtatcggac   1440
tcgaccaact ctaccaatcc ctcgtcgacg gaaacttcga cgacgccgcc tgggcccaag   1500
gacgttgcga cgccatcgtc cgttccggag ccggaaccgt cggacgtacc caaatcgccc   1560
gtcgttccgc cgccgtctgg accgacggat gcgtcgaggt cctcgccgac tccggaaacc   1620
gtcgtccatc cacccgtcca cgtgccaagg agtaagtcca attactcttc aacatcccta   1680
catgctcttt ctccctgtgc tcccaccccc tattttgtt attatcaaaa aacttctctt   1740
aatttctttg tttttagct tcttttaagt cacctctaac aatgaaattg tgtagattca   1800
aaaatagaat taattcgtaa taaaagtcg aaaaaaattg tgctccctcc ccccattaat   1860
aataattcta tcccaaaatc tacacaatgt tctgtgtaca cttcttatgt tttttacttc   1920
tgataaattt ttttgaaaca tcatagaaaa aaccgcacac aaaataccttt atcatatgtt   1980 acgtttcagt ttatgaccgc aattttttact agtgcaggag ctgtaagttt aaaataactt   2040
cgtatagcat acattatacg aagttatttt cagggagccg gatct                   2085
```

<210> SEQ ID NO 44
<211> LENGTH: 2308
<212> TYPE: DNA
<213> ORGANISM: Artificial Sequence
<220> FEATURE:
<223> OTHER INFORMATION: pDSP57 mScarlet donor homology sequences
<220> FEATURE:
<221> NAME/KEY: misc_feature
<222> LOCATION: (1)..(1016)
<223> OTHER INFORMATION: mScarlet coding sequence, and partial prsp-0
      coding sequence
<220> FEATURE:
<221> NAME/KEY: misc_feature
<222> LOCATION: (1017)..(1032)
<223> OTHER INFORMATION: Additional prps-0 promoter
<220> FEATURE:
<221> NAME/KEY: misc_feature
<222> LOCATION: (1033)..(1066)
<223> OTHER INFORMATION: LoxP site
<220> FEATURE:
<221> NAME/KEY: misc_feature
<222> LOCATION: (1067)..(1105)
<223> OTHER INFORMATION: Multiple cloning site
<220> FEATURE:
<221> NAME/KEY: misc_feature
<222> LOCATION: (1106)..(1505)
<223> OTHER INFORMATION: hsp-16.41 promoter

```
<220> FEATURE:
<221> NAME/KEY: misc_feature
<222> LOCATION: (1506)..(2308)
<223> OTHER INFORMATION: 5' portion of mScarlet coding sequence

<400> SEQUENCE: 44
gccattgtcc gtcaggacat tgttggagcc gaaatccgcg tgcacgaggt gccggacttc      60
ggggcagtcc tcggcccaaa gcatcagctc atcgagagcc tgcgcgacgg acgcactgac     120
ggtgtcgtcc atcacagttt gccagtgata cacatgggga tcagcaatcg cgcatatgaa     180
atcacgccat gtagtgtatt gaccgattcc ttgcggtccg aatgggccga acccgctcgt     240
ctggctaaga tcgccgcag cgatcgcatc catggcctcc gcgaccggct gcagaacagc      300
gggcagttcg gtttcaggca ggtcttgcaa cgtgacaccc tgtgcacggc gggagatgca     360
ataggtcagg ctctcgctga attccccaat gtcaagcact tccggaatcg ggagcgcggc     420
cgatgcaaag tgccgataaa cataacgatc tttgtagaaa ccatcggcgc agctatttac     480
ccgcaggaca tatccacgcc ctcctacatc gaagctgaaa gcacgagatt cttcgccctc     540
cgagagctgc atcaggtcgg agacgctgtc gaacttttcg atcagaaact tctcgacaga     600
cgtcgcggtg agttcaggct ttttcatgga gcctgctttt ttgtacaaac ttgcggcacc     660
gcctgacata ttaccttaaa attcaaaaat taatttcaga tcagtcataa ccaagaaaac     720
aaaataaacg ttaggacaga aaattcaaat taattaaaaa ttatgctgaa taagaaaatt     780
acatgcaaag cctta ttttc ctcatagaaa cagttgaata acatatttt taattgaaaa     840 catagcaaaa ttcgtggtaa aatttgtcaa aaccttggaa aaaatcgaaa aagaacatt     900 tcccgatgca ttttcctatt tctcgttgcc gacaacgtat aaacgttgaa tactcagtca     960
acgaatttgg ctgctggctt ggactctcgc acggaagaga cgcgtgtgta gatttacgac    1020
gaaagcaaaa atataacttc gtatagcata cattatacga agttatgtaa aacgacggcc    1080
agtccgtaat acgactcact aagggatca ccaaaaacgg aacgttgagc tggacggaaa     1140
tagtggtaaa gtgacatgat tatagtttga agatttctaa tttcacaatt agagcaaatg    1200
ttgttcggta tttattttca acggtatttta tactatttc cacctttttc tagaacattc    1260
gagctgcttg ttgcaaaagg agggcgactc acattcggta catggaaaag tagtgtacac    1320
aataaagaga cccagataca ttttccgtct gcgtctcttt gcacccaccg ggagtatttt    1380
caaacgaatg catctaggac cttctagaac attctgtaag gctgcagaat gcgggtatat    1440
aaggaaagcg ggctcagagg aagccaacac gctttgttct agtgcatcta aaaaacttcg    1500
aaaatatggt ttccaaggga gaggctgtta tcaaggaatt catgacttac ccaaagaaga    1560
agcgtaaggt cgaacttatc aaggagttta tgcgctttaa ggttcacatg gaaggatcta    1620
tgaacggaca cgaattcgaa atcgaaggag aaggagaagg acgtccatac gagggaactc    1680
aaactgctaa gcttaaggta agtttatcta aaagtttttt cattcaaaat gtgtaaaaat    1740
tcatttaaaa taacccaaaa atcattaatc ctcgatattt tcaggttact aaaggaggac    1800
cacttccatt ctcttgggat atcctttctc cacaattcat gtacggatct cgcgctttca    1860
tcaagcaccc agctgatatc ccagattact acaagcaatc tttcccagaa ggattcaaat    1920
gggagcgtgt tatgaacttc gaagatggag gagctgttac cgttacccaa gatacctccc    1980
ttgaggatgg aaccctatc tacaaggtat tttcctgcat ttttcaactg gaaaatgaa      2040 agaaaatcga aatttcagg ttaagcttcg tggaactaat ttcccaccag atggaccagt     2100
tatgcaaaag aagactatgg gatgggaggc ttctaccgag cgcctttacc cagaggatgg    2160
```

-continued

| | |
|---|---|
| agtccttaag ggagatatca agatggctct tcgtcttaag gatggaggac gttaccttgc | 2220 |
| tgatttcaag gtaagttttc tagagacctt tactaactaa ctaggtctca tagatttca | 2280 |
| gactacttac aaggctaaga agccagtt | 2308 |

<210> SEQ ID NO 45
<211> LENGTH: 2803
<212> TYPE: DNA
<213> ORGANISM: Artificial Sequence
<220> FEATURE:
<223> OTHER INFORMATION: pDSP58 unc-119 donor homology sequences
<220> FEATURE:
<221> NAME/KEY: misc_feature
<222> LOCATION: (1)..(1500)
<223> OTHER INFORMATION: Split unc-119 selection gene, full promoter and
      partial coding sequence
<220> FEATURE:
<221> NAME/KEY: misc_feature
<222> LOCATION: (1501)..(1534)
<223> OTHER INFORMATION: lox N site
<220> FEATURE:
<221> NAME/KEY: misc_feature
<222> LOCATION: (1535)..(1573)
<223> OTHER INFORMATION: Multiple cloning site
<220> FEATURE:
<221> NAME/KEY: misc_feature
<222> LOCATION: (1574)..(1973)
<223> OTHER INFORMATION: hsp-16.41 promoter
<220> FEATURE:
<221> NAME/KEY: misc_feature
<222> LOCATION: (1974)..(2803)
<223> OTHER INFORMATION: Split mNeonGreen 5' coding sequence

<400> SEQUENCE: 45

| | |
|---|---|
| gttgctccga ccgttttgag tttcaaaaag tttggagcaa atctataacg cacgtatctt | 60 |
| gccgactcct gtggcgactc atcattctcc tgatcgttct ccggtttggc gatctcgaaa | 120 |
| agcacttgct cagtgtccag atcacggatt tggaacttgg tgaactcgat gttatagatg | 180 |
| ttcgcagatg gggagcataa gaatcctaaa tttatgtttt aaactgaaat ccaaagggag | 240 |
| caagatacct tgagtgattc ccggaagtgc taaaacgtcg ttcggagtga tttgagcttt | 300 |
| cttcgcaagc tccgattccg ttgtgattcc ttgttcggtg cttggtggtg gccgtggcat | 360 |
| ctggaaatat ggaaaagttc aacaaaaaga aagagaaaa gaatgaaatc ggatatcaag | 420 |
| agttagttga gcggtttctc tagttttctg agtctcacct gcgacgggaa ggtcgccgag | 480 |
| ccgggtggaa tcgatcgttg ttgctcggct ttcatatcgg tttggttgga agcggctgaa | 540 |
| aacggaaaga agtggaagaa ggaaaagagt gtggtgtgac aggaaaatgg taattagagg | 600 |
| gtgccaaata accagctata ttttgttttt ttttgaaaac attttaaaa agaaaaatac | 660 |
| gataatgata tcagatggat ttccggaaaa ctggtatgaa aatttcaac ctttttgagt | 720 |
| acatgtaatc aaaatacact ttgtaaatta tcatttttat tgaaactcca ccattttct | 780 |
| atttataacg ctaataattt gaaaagaaa cctattgcga accgcggggt gaatcccaaa | 840 |
| aacgaatgcg ttttggtgga gtgattgatt cgaatcgaag aagaaaaga gaagacgtg | 900 |
| gaatagagag ctcactctta accgagcagc acacaccgac agaaaaaaa atgaaatgaa | 960 |
| tgagggtctt cttcttcttc ttcttcgaat gattgacaga atgggaaaa agaggaagat | 1020 |
| tgagaaggga aaaggaagg agaaagaag cagaagaaga cgtcagagag gagaggaacg | 1080 |
| agcggaaaag cagcgggcgc aagtcataga agtagcagag ctggggagaa gaagacacta | 1140 |
| tccaagaaag gaatgacgag agagtatgca aaggggtata gggtgcagac agaataggaa | 1200 |
| cagaataaca gatgatgagc caagaagagt tgaaagggc gatgaatttg tcatgtaact | 1260 |

```
taatttgggt caatttgagc atgatgaatt gaaatcatcc cttgttggga gttaataacc    1320
ggtttgttat cagaaaccct gtaatagaag ggcgccctaa ctttgagcca attcatcccg    1380
gtttctgtca aatatatcaa aaagtggtca actgacaaat tgttttttgat attataataa   1440 acattttatc cgttaacaat tttcgaatac tttttacaag gacttggata aattggctca    1500
ataacttcgt atagtatacc ttatacgaag ttatgtaaaa cgacggccag tccgtaatac    1560
gactcactta agggatcacc aaaaacggaa cgttgagctg gacggaaata gtggtaaagt    1620
gacatgatta tagtttgaag atttctaatt tcacaattag agcaaatgtt gttcggtatt    1680
tattttcaac ggtatttata ctattttcca ccttttttcta gaacattcga gctgcttgtt   1740
gcaaaaggag ggcgactcac attcggtaca tggaaaagta gtgtacacaa taaagagacc    1800
cagatacatt ttccgtctgc gtctctttgc acccaccggg agtattttca aacgaatgca    1860
tctaggacct tctagaacat tctgtaaggc tgcagaatgc gggtatataa ggaaagcggg    1920
ctcagaggaa gccaacacgc tttgttctag tgcatctaaa aaacttcgaa aatatggttt    1980
ccaagggaga ggctgttatc aaggaattca tgacttaccc aaagaagaag cgtaaggtcg    2040
gagaagagga caacatggct tctcttccag ctactcacga acttcatatt ttcggatcta    2100
tcaacggagt tgatttcgat atggttggac aaggaactgg aaacccaaac gacggatacg    2160
aagagcttaa ccttaagtct accaaggtaa gtttatctaa aaagttttttc attcaaaatg    2220 tgtaaaaatt catttaaaat aacccaaaaa tcattaatcc tcgatatttt cagggagatc    2280
ttcaattctc tccatggatc cttgttccac acattggata cggattccac caataccttc    2340
catacccaga tggaatgtct ccattccaag ctgctatggt tgacggatct ggataccaag    2400
ttcaccgtac tatgcaattc gaggacggag cttccctcac cgtcaactac cgttacactt    2460
acgaaggatc tcacatcaag gtattttcct gcattttttca actgggaaaa tgaaagaaaa    2520
tcgataattt cagggagaag ctcaagttaa gggaaccgga ttcccagccg atggaccagt    2580
tatgaccaac tctcttaccg ccgctgattg gtgccgctct aagaagacct acccaaacga    2640
taaggtaagt tttctagaga cctttactaa ctaactaggt ctcatagatt ttcagactat    2700
catctctact ttcaagtggt cttacactac cggaaacgga aagcgttacc gctctaccgc    2760
tcgcactact tacactttcg ctaagccaat ggctgccaac tac                      2803
```

<210> SEQ ID NO 46
<211> LENGTH: 1068
<212> TYPE: DNA
<213> ORGANISM: Artificial Sequence
<220> FEATURE:
<223> OTHER INFORMATION: 500 bp donor homology insert from PX742
<220> FEATURE:
<221> NAME/KEY: misc_feature
<222> LOCATION: (1)..(512)
<223> OTHER INFORMATION: Left homology arm, partial prsp-0 promoter and
      exon 1 of Hygromycin B resistance gene
<220> FEATURE:
<221> NAME/KEY: misc_feature
<222> LOCATION: (513)..(558)
<223> OTHER INFORMATION: Synthetic intron between exon 1 and exon 2
<220> FEATURE:
<221> NAME/KEY: misc_feature
<222> LOCATION: (559)..(1068)
<223> OTHER INFORMATION: Right homology arm, partial Hygromycin B
      resistance gene exon 2

<400> SEQUENCE: 46

```
cgcgtctctt ccgtgcgaga gtccaagcca gcagccaaat tcgttgactg agtattcaac       60
gtttatacgt tgtcggcaac gagaaatagg aaaatgcatc gggaaatgtt cttttttcga      120
```

```
ttttttccaa ggttttgaca aattttacca cgaattttgc tatgttttca attaaaaaat      180
atgttattca actgtttcta tgaggaaaat aaggctttgc atgtaatttt cttattcagc      240 ataatttta attaatttga atttctgtc ctaacgttta ttttgttttc ttggttatga       300
ctgatctgaa attaatttt gaattttaag gtaatatgaa aaacccgag ttgaccgcca       360 catccgtaga gaagttcctc atcgagaagt tcgactccgt ctccgacctc atgcaactct     420
ccgagggaga ggagtcccgt gccttctcct tcgacgtcgg aggacgtgga tacgtcctcc    480
gtgtcaactc ctgcgccgac ggattctaca aggtaagttt aaacatatnn nnnnnnnnnn    540
nnntatttaa attttcagga ccgttacgtc taccgtcact tcgcctccgc cgccctccca    600
atcccagagg tcctcgacat cggagagttc tccgagtccc tcacctactg catctcccgt    660
cgtgcccaag gagtcaccct ccaagacctc ccagagaccg agctcccagc cgtcctccaa    720
ccagtcgccg aggccatgga cgccatcgcc gccgccgacc tctcccaaac ctccggattc    780
ggaccattcg gaccacaagg aatcggacaa tacaccaccct ggcgtgactt catctgcgcc  840
atcgccgacc cacacgtcta ccactggcaa accgtcatgg acgacaccgt ctccgcctcc    900
gtcgcccaag ccctcgacga gctcatgctc tgggccgagg actgcccaga ggtccgtcac  960
ctcgtccacg ccgacttcgg atccaacaac gtcctcaccg acaacggacg tatcaccgcc   1020
gtcatcgact ggtccgaggc catgttcgga gactcccaat acgaggtc                1068
```

<210> SEQ ID NO 47
<211> LENGTH: 501
<212> TYPE: DNA
<213> ORGANISM: Artificial Sequence
<220> FEATURE:
<223> OTHER INFORMATION: 501bp pZCS32 (ZCS276-ZCS278) amplification product

<400> SEQUENCE: 47

```
gtctaccgtc acttcgcctc cgccgccctc ccaatcccag aggtcctcga catcggagag      60
ttctccgagt ccctcaccta ctgcatctcc cgtcgtgccc aaggagtcac cctccaagac    120
ctcccagaga ccgagctccc agccgtcctc caaccagtcg ccgaggccat ggacgccatc    180
gccgccgccg acctctccca aacctccgga ttcggaccat tcggaccaca aggaatcgga    240
caatacacca cctggcgtga cttcatctgc gccatcgccg acccacacgt ctaccactgg    300
caaaccgtca tggacgacac cgtctccgcc tccgtcgccc aagccctcga cgagctcatg    360
ctctgggccg aggactgccc agaggtccgt cacctcgtcc acgccgactt cggatccaac   420
aacgtcctca ccgacaacgg acgtatcacc gccgtcatcg actggtccga ggccatgttc    480
ggagactccc aatacgaggt c                                              501
```

<210> SEQ ID NO 48
<211> LENGTH: 501
<212> TYPE: DNA
<213> ORGANISM: Artificial Sequence
<220> FEATURE:
<223> OTHER INFORMATION: 501bp pZCS32 (ZCS273-ZCS275) amplification product

<400> SEQUENCE: 48

```
cgcgtctctt ccgtgcgaga gtccaagcca gcagccaaat tcgttgactg agtattcaac      60
gtttatacgt tgtcggcaac gagaaatagg aaaatgcatc gggaaatgtt ctttttttcga   120 ttttttccaa ggttttgaca aattttacca cgaattttgc tatgttttca attaaaaaat     180
```

```
atgttattca actgtttcta tgaggaaaat aaggctttgc atgtaatttt cttattcagc      240 ataatttta attaatttga atttctgtc ctaacgttta ttttgttttc ttggttatga        300
ctgatctgaa attaattttt gaatttaag gtaatatgaa aaacccgag ttgaccgcca        360 catccgtaga gaagttcctc atcgagaagt tcgactccgt ctccgacctc atgcaactct      420
ccgagggaga ggagtcccgt gccttctcct cgacgtcgg aggacgtgga tacgtcctcc      480
gtgtcaactc ctgcgccgac g                                                501
```

```
<210> SEQ ID NO 49
<211> LENGTH: 150
<212> TYPE: DNA
<213> ORGANISM: Artificial Sequence
<220> FEATURE:
<223> OTHER INFORMATION: 150 bp left homology arm (ZCS285-ZCS275) of
      pZCS32

<400> SEQUENCE: 49
tgaccgccac atccgtagag aagttcctca tcgagaagtt cgactccgtc tccgacctca      60
tgcaactctc cgagggagag gagtcccgtg ccttctcctt cgacgtcgga ggacgtggat      120
acgtcctccg tgtcaactcc tgcgccgacg                                       150

<210> SEQ ID NO 50
<211> LENGTH: 150
<212> TYPE: DNA
<213> ORGANISM: Artificial Sequence
<220> FEATURE:
<223> OTHER INFORMATION: 150 bp right homology arm (ZCS276-ZCS286) of
      pZCS32

<400> SEQUENCE: 50
tgaccgccac atccgtagag aagttcctca tcgagaagtt cgactccgtc tccgacctca      60
tgcaactctc cgagggagag gagtcccgtg ccttctcctt cgacgtcgga ggacgtggat      120
acgtcctccg tgtcaactcc tgcgccgacg                                       150

<210> SEQ ID NO 51
<211> LENGTH: 1773
<212> TYPE: DNA
<213> ORGANISM: Artificial Sequence
<220> FEATURE:
<223> OTHER INFORMATION: pZCS32 lineage tracking landing pad
      (prsp-0::dHygR1::synthetic guide::dHygR2::unc-54UTR::LoxP)
<220> FEATURE:
<221> NAME/KEY: misc_feature
<222> LOCATION: (1)..(1722)
<223> OTHER INFORMATION: prsp-0 promoter, Hygromycin B resistance gene
      missing synthetic intron and 6 conds flanking the intron; when
      exons join, unique Cas9 guide RNA target is created
<220> FEATURE:
<221> NAME/KEY: misc_feature
<222> LOCATION: (1723)..(1733)
<223> OTHER INFORMATION: Synthetic spacer sequence
<220> FEATURE:
<221> NAME/KEY: misc_feature
<222> LOCATION: (1734)..(1767)
<223> OTHER INFORMATION: LoxP site
<220> FEATURE:
<221> NAME/KEY: misc_feature
<222> LOCATION: (1768)..(1773)
<223> OTHER INFORMATION: Synthetic spacer sequence

<400> SEQUENCE: 51
atttttgctt tcgtcgtaaa tctacacacg cgtctcttcc gtgcgagagt ccaagccagc      60
agccaaattc gttgactgag tattcaacgt ttatacgttg tcggcaacga gaaataggaa      120
```

| | | | |
|---|---|---|---|
| aatgcatcgg | gaaatgttct | tttttcgatt | ttttccaagg ttttgacaaa ttttaccacg | 180 |
| aattttgcta | tgttttcaat | taaaaaatat | gttattcaac tgtttctatg aggaaaataa | 240 |
| ggctttgcat | gtaattttct | tattcagcat | aattttaat taatttgaat tttctgtcct | 300 |
| aacgtttatt | ttgttttctt | ggttatgact | gatctgaaat taattttga attttaaggt | 360 |
| aatatgaaaa | acccgagtt | gaccgccaca | tccgtagaga agttcctcat cgagaagttc | 420 |
| gactccgtct | ccgacctcat | gcaactctcc | gagggagagg agtcccgtgc cttctccttc | 480 |
| gacgtcggag | gacgtggata | cgtcctccgt | gtcaactcct gcgccgacgg tctaccgtca | 540 |
| cttcgcctcc | gccgcccctcc | caatcccaga | ggtcctcgac atcggagagt tctccgagtc | 600 |
| cctcacctac | tgcatctccc | gtcgtgccca | aggagtcacc ctccaagacc tcccagagac | 660 |
| cgagctccca | gccgtcctcc | aaccagtcgc | cgaggccatg gacgccatcg ccgccgccga | 720 |
| cctctcccaa | acctccggat | tcggaccatt | cggaccacac ggaatcggac aatacaccac | 780 |
| ctggcgtgac | ttcatctgcg | ccatcgccga | cccacacgtc taccactggc aaaccgtcat | 840 |
| ggacgacacc | gtctccgcct | ccgtcgccca | agccctcgac gagctcatgc tctgggccga | 900 |
| ggactgccca | gaggtccgtc | acctcgtcca | cgccgacttc ggatccaaca acgtcctcac | 960 |
| cgacaacgga | cgtatcaccg | ccgtcatcga | ctggtccgag gccatgttcg gagactccca | 1020 |
| atacgaggtc | gccaacatct | tcttctggcg | tccatggctc gcctgcatgg agcaacaaac | 1080 |
| ccgttacttc | gagcgtcgtc | acccagagct | cgccggatcc ccacgtctcc gtgcctacat | 1140 |
| gctccgtatc | ggactcgacc | aactctacca | atccctcgtc gacggaaact cgacgacgc | 1200 |
| cgcctgggcc | caaggacgtt | gcgacgccat | cgtccgttcc ggagccggaa ccgtcggacg | 1260 |
| tacccaaatc | gcccgtcgtt | ccgccgccgt | ctggaccgac ggatgcgtcg aggtcctcgc | 1320 |
| cgactccgga | aaccgtcgtc | catccaccg | tccacgtgcc aaggagtaag tccaattact | 1380 |
| cttcaacatc | cctacatgct | ctttctccct | gtgctcccac cccctatttt tgttattatc | 1440 |
| aaaaaacttc | tcttaatttc | tttgttttt | agcttctttt aagtcacctc taacaatgaa | 1500 |
| attgtgtaga | ttcaaaaata | gaattaattc | gtaataaaaa gtcgaaaaaa attgtgctcc | 1560 |
| ctcccccccat | taataataat | tctatcccaa | aatctacaca atgttctgtg tacacttctt | 1620 |
| atgtttttta | cttctgataa | atttttttga | aacatcatag aaaaaaccgc acacaaaata | 1680 |
| ccttatcata | tgttacgttt | cagtttatga | ccgcaatttt tagtaagttt aaaataactt | 1740 |
| cgtatagcat | acattatacg | aagttatttt | cag | 1773 |

<210> SEQ ID NO 52
<211> LENGTH: 469
<212> TYPE: DNA
<213> ORGANISM: Artificial Sequence
<220> FEATURE:
<223> OTHER INFORMATION: 150 bp PX745 array
<220> FEATURE:
<221> NAME/KEY: misc_feature
<222> LOCATION: (1)..(154)
<223> OTHER INFORMATION: Left homology arm containing partial Hygromycin
      B resistance gene exon 1
<220> FEATURE:
<221> NAME/KEY: misc_feature
<222> LOCATION: (155)..(185)
<223> OTHER INFORMATION: Left side of intron
<220> FEATURE:
<221> NAME/KEY: misc_feature
<222> LOCATION: (186)..(195)
<223> OTHER INFORMATION: MIyI cut site
<220> FEATURE:
<221> NAME/KEY: misc_feature
<222> LOCATION: (186)..(190)

<223> OTHER INFORMATION: MIyI recognition site
<220> FEATURE:
<221> NAME/KEY: misc_feature
<222> LOCATION: (191)..(195)
<223> OTHER INFORMATION: Spacer to give MIyI blunt cut 4 bp from primer
<220> FEATURE:
<221> NAME/KEY: misc_feature
<222> LOCATION: (196)..(228)
<223> OTHER INFORMATION: Read 1 primer sequence
<220> FEATURE:
<221> NAME/KEY: misc_feature
<222> LOCATION: (229)..(243)
<223> OTHER INFORMATION: Synthetic barcode
<220> FEATURE:
<221> NAME/KEY: misc_feature
<222> LOCATION: (244)..(277)
<223> OTHER INFORMATION: Read 2 primer sequence
<220> FEATURE:
<221> NAME/KEY: misc_feature
<222> LOCATION: (278)..(287)
<223> OTHER INFORMATION: MIyI cut site
<220> FEATURE:
<221> NAME/KEY: misc_feature
<222> LOCATION: (278)..(282)
<223> OTHER INFORMATION: Spacer to give MIyI blunt cut 4 bp from primer
<220> FEATURE:
<221> NAME/KEY: misc_feature
<222> LOCATION: (283)..(287)
<223> OTHER INFORMATION: MIyI recognition site
<220> FEATURE:
<221> NAME/KEY: misc_feature
<222> LOCATION: (288)..(316)
<223> OTHER INFORMATION: Right side of synthetic intron
<220> FEATURE:
<221> NAME/KEY: misc_feature
<222> LOCATION: (317)..(469)
<223> OTHER INFORMATION: Right homology arm containing 5' partial exon 2
    of Hygromycin B resistance gene

<400> SEQUENCE: 52
tgaccgccac atccgtagag aagttcctca tcgagaagtt cgactccgtc tccgacctca      60
tgcaactctc cgagggagag gagtcccgtg ccttctcctt cgacgtcgga ggacgtggat     120
acgtcctccg tgtcaactcc tgcgccgacg gattctacaa ggtaagttta aacatatgcc     180
cgggcgagtc ataatacact ctttccctac acgacgctct tccgatctnn nnnnnnnnn     240 nnnagatcgg aagagcacac gtctgaactc cagtcacatt atgactcgcc cgggctattt     300
aaattttcag gaccgttacg tctaccgtca cttcgcctcc gccgccctcc caatcccaga     360
ggtcctcgac atcggagagt tctccgagtc cctcacctac tgcatctccc gtcgtgccca     420
aggagtcacc ctccaagacc tcccagagac cgagctccca gccgtcctc               469

<210> SEQ ID NO 53
<211> LENGTH: 48
<212> TYPE: DNA
<213> ORGANISM: Artificial Sequence
<220> FEATURE:
<223> OTHER INFORMATION: Illustrative 3'mScarlet coding with tbb-2 UTR
    sequence, positive sense

<400> SEQUENCE: 53
cactccaccg gaggaatgga cgagctctac aagtaaacta gtgataaa                  48

<210> SEQ ID NO 54
<211> LENGTH: 48
<212> TYPE: DNA
<213> ORGANISM: Artificial Sequence
<220> FEATURE:
<223> OTHER INFORMATION: Illustrative 3' mScarlet coding with tbb-2 UTR
    sequence, negative sense

<400> SEQUENCE: 54
gtgaggtggc ctccttacct gctcgagatg ttcatttgat cactattt            48

<210> SEQ ID NO 55
<211> LENGTH: 11
<212> TYPE: PRT
<213> ORGANISM: Artificial Sequence
<220> FEATURE:
<223> OTHER INFORMATION: Illustrative 3' mScarlet coding with tbb-2 UTR
      translation

<400> SEQUENCE: 55

His Ser Thr Gly Gly His Asp Glu Leu Tyr Lys
1               5                   10

<210> SEQ ID NO 56
<211> LENGTH: 37
<212> TYPE: DNA
<213> ORGANISM: Artificial Sequence
<220> FEATURE:
<223> OTHER INFORMATION: Illustrative 3' mScarlet coding with landing
      pad sequence, positive sense

<400> SEQUENCE: 56
cactccaccg gagactagtg ataaatgcaa aatcctt                        37

<210> SEQ ID NO 57
<211> LENGTH: 37
<212> TYPE: DNA
<213> ORGANISM: Artificial Sequence
<220> FEATURE:
<223> OTHER INFORMATION: Illustrative 3' mScarlet coding with landing
      pad sequence, negative sense

<400> SEQUENCE: 57
gtgaggtggc ctctgatcac tatttacgtt ttaggaa                        37

<210> SEQ ID NO 58
<211> LENGTH: 4
<212> TYPE: PRT
<213> ORGANISM: Artificial Sequence
<220> FEATURE:
<223> OTHER INFORMATION: Illustrative 3' mScarlet translation

<400> SEQUENCE: 58

His Ser Thr Gly
1

<210> SEQ ID NO 59
<211> LENGTH: 68
<212> TYPE: DNA
<213> ORGANISM: Artificial Sequence
<220> FEATURE:
<223> OTHER INFORMATION: 3' mScarlet sequence after barcode integration,
      positive sense
<220> FEATURE:
<221> NAME/KEY: misc_feature
<222> LOCATION: (34)..(48)
<223> OTHER INFORMATION: n is a, c, g, or t

<400> SEQUENCE: 59
cactccaccg gaggaatgga cgagctctac aagnnnnnnn nnnnnnnnta aactagtgat   60
aaatgcaa                                                           68

<210> SEQ ID NO 60
<211> LENGTH: 68

```
<212> TYPE: DNA
<213> ORGANISM: Artificial Sequence
<220> FEATURE:
<223> OTHER INFORMATION: 3' mScarlet sequence after barcode integration,
      negative sense
<220> FEATURE:
<221> NAME/KEY: misc_feature
<222> LOCATION: (34)..(48)
<223> OTHER INFORMATION: n is a, c, g, or t

<400> SEQUENCE: 60
gtgaggtggc ctccttacct gctcgagatg ttcnnnnnnn nnnnnnnnat ttgatcacta      60
tttacgtt                                                              68

<210> SEQ ID NO 61
<211> LENGTH: 16
<212> TYPE: PRT
<213> ORGANISM: Artificial Sequence
<220> FEATURE:
<223> OTHER INFORMATION: Illustrative 3' mScarlet restored translation
<220> FEATURE:
<221> NAME/KEY: misc_feature
<222> LOCATION: (12)..(16)
<223> OTHER INFORMATION: Xaa can be any naturally occurring amino acid

<400> SEQUENCE: 61

His Ser Thr Gly Gly His Asp Glu Leu Tyr Lys Xaa Xaa Xaa Xaa Xaa
1               5                   10                  15
```

GENETIC DATA COMPRESSION AND METHODS OF USE

CROSS-REFERENCE TO RELATED APPLICATION

This application claims priority to U.S. Provisional Application No. 63/013,365, filed Apr. 21, 2020, which is incorporated herein by reference in its entirety.

ACKNOWLEDGMENT OF GOVERNMENT SUPPORT

This invention was made with government support under grant numbers AG056436 and GM131838 awarded by the National Institutes of Health. The government has certain rights in the invention.

FIELD

This disclosure relates to systems and methods for producing genetically modified cells or organisms, particularly utilizing genetic data compression to generate a plurality of genetically modified cells or organisms.

SEQUENCE LISTING INCORPORATION BY REFERENCE

The Sequence Listing is submitted as an ASCII text file in the file named Sequence_Listing (Text File), which was created on Apr. 21, 2021, and is 42,682 bytes, which is incorporated by reference herein.

BACKGROUND

A fundamental tool in molecular biology is the generation of transgenic individuals having experimentally provided DNA integrated into their genomes. Technological advances in transgenesis are highly impactful, as illustrated by the role of transgenesis in the foundation of modern molecular biology and the recent changes brought about by the development of targetable nucleases and related genome engineering techniques that allow the creation of non-random, custom-designed genetic modifications. Targetable nucleases such as transposons, zinc-finger nucleases, and Cas proteins have all been widely adopted for such precision genetic engineering. As precision has increased, throughput in transgenesis and DNA synthesis has grown exponentially.

However, all transformation technologies to date, including CRISPR, are limited by the need to move nucleic acids across cell boundaries, e.g., requiring a single nucleic acid transit event per designed genomic modification. This limitation is typically overcome in microbial and cell culture systems by massively parallelizing these transit events, using ease of movement across cell membranes and availability of large population sizes, making library transgenesis possible through transformation and transfection of DNA plasmids. In non-microbial models (e.g., *C. elegans, D. melanogaster*, and mammalian systems), such pre-designed, high-throughput, parallelized techniques are not available. Similar throughput in transgenesis has yet to be realized because of species-specific limitations. Broadly speaking, microinjections (or other low throughput DNA transportation) must be performed at precise stages in development to modify individual genomes. These protocols are typically done with the experimental goal of creating a single transgenic modification. Therefore, creating precision transgenics on the scale of tens to thousands from individual injections has generally yet to be realized. Thus, there is a barrier in non-microbial models to performing experiments such as lineage tracking or DNA transformation-based genetic screening that require generation of large populations of individuals with unique genetic modifications.

SUMMARY

Provided herein are genetic engineering systems that allow creation of large numbers of pre-designed, single-copy lineages simultaneously. The method is in some examples termed Transgenic Arrays Resulting in Diversity of Integrated Sequences (TARDIS). In some examples, the TARDIS system massively increases transformation throughput by supplying the organism with a "database" of DNA sequences in the form of a heritable DNA element (such as an array or artificial chromosome). The DNA element represents a "compressed" state including a plurality of DNA sequences that can be integrated at a future time point. This compression allows individual "transit events" to represent many simultaneous DNA sequences that can later be integrated individually. To integrate the large number of compressed sequences, the TARDIS system uses the heritability of the compressed DNA to enlarge the population carrying the compressed sequences. Integration is then facilitated at genetically engineered sites (e.g., a synthetic landing pad), which are engineered to recombine with the elements of the compressed DNA in a defined way. The recombination event is a "decompression" step, allowing for a functional output.

Some embodiments herein provide methods of producing a plurality of genetically modified cells, which include introducing a nucleic acid molecule including a plurality of index sequences into a cell including a genomic polynucleotide (e.g., an intron or exon of a gene, or a promoter element) that includes a synthetic landing pad, wherein each of the plurality of index sequences includes a first portion of a nucleotide sequence and the synthetic landing pad includes a second portion of the nucleotide sequence to produce a cell including the synthetic landing pad and the nucleic acid molecule including the plurality of index sequences. In some examples, the cell may be a eukaryotic cell (for example, a yeast cell, a mammalian cell, a *Caenorhabditis elegans* cell, or a *Drosophila* cell), or a bacterial cell. In some examples, introducing the nucleic acid molecule including the plurality of index sequences into the cell including the genomic polynucleotide that includes the synthetic landing pad includes injecting the nucleic acid molecule into an animal including the cell. The methods also include generating a plurality of progeny cells including the genomic polynucleotide that includes the synthetic landing pad and the nucleic acid molecule including the plurality of index sequences, integrating a single index sequence into the synthetic landing pad in each of the plurality of progeny cells, thereby linking the first and second portions of the nucleotide sequence, and selecting progeny cells including integrated index sequences based on presence or activity of the linked first and second portions of the nucleotide sequence, thereby producing a plurality of genetically modified cells. In some examples, the lineage of the cell is traced by detecting an index sequence in progeny of at least one of the plurality of genetically modified cells.

In some embodiments, the nucleic acid molecule including the plurality of index sequences is an extrachromosomal array, a plasmid, or an artificial chromosome. In some examples, the nucleic acid molecule including the plurality of index sequences includes about 500-3,000 index sequences. In particular examples, each of the plurality of index sequences includes a homologous fragment of the genomic polynucleotide, wherein each of the plurality of index sequences are different. In these and other examples, the first portion and the second portion of the nucleotide sequence may reconstitute a functional gene (for example, a selectable marker or reporter gene) when linked. In some examples, each of the plurality of index sequences includes a sequence variant of a reference coding sequence, a reference non-coding sequence, a library sequence, a randomized sequence, or a promoter element. In particular examples, the method further includes selecting a single sequence variant of the reference coding sequence by selecting a genetically modified cell including the reference coding sequence variant, selecting a single sequence variant of the reference non-coding sequence by selecting a genetically modified cell including the reference non-coding sequence variant, selecting a single library sequence by selecting a genetically modified cell including the library sequence, selecting a single randomized sequence by selecting a genetically modified cell including the randomized sequence, or selecting a single promoter element by selecting a genetically modified cell including a screenable marker or reporter gene operably linked to the promoter element in the genomic polynucleotide.

In some embodiments, the synthetic landing pad further includes a site-specific nuclease (SSN) recognition site and homology arms flanking the SSN recognition site, and each of the plurality of index sequences is flanked by the homology arms in the nucleic acid molecule including the plurality of index sequences. In particular examples, each of the homology arms is about 150-500 nucleotides in length. In some examples, the SSN is a Cas endonuclease (for example, Cas9), zinc-finger nuclease, or TALEN.

In some embodiments, the method further includes selecting a genetically modified cell including an index sequence by an assay phenotype, or by expression of a selectable marker or reporter, and generating variants of the index sequence. In such embodiments, the method further includes introducing a nucleic acid molecule including the variants of the index sequence into a cell including a genomic polynucleotide comprising a synthetic landing pad, wherein each of the variants of the index sequence includes a first portion of a nucleotide sequence and the synthetic landing pad includes a second portion of the nucleotide sequence to produce a cell including the synthetic landing pad and the nucleic acid molecule including the variants of the index sequence. Such methods further include generating a plurality of progeny cells including the genomic polynucleotide including the synthetic landing pad and the nucleic acid molecule including the variants of the index sequence, integrating a single variant of the index sequence into the synthetic landing pad in each of the plurality of progeny cells, thereby linking the first and second portions of the nucleotide sequence, and selecting progeny cells including integrated variants of the index sequence based on presence or activity of the linked first and second portions of the nucleotide sequence.

Further embodiments herein provide genetically modified cells including an extrachromosomal array including a plurality of index sequences, and a genomic polynucleotide including one of the plurality of index sequences integrated at a synthetic landing pad, wherein the integrated index sequence includes a first portion of a nucleotide sequence and the synthetic landing pad includes a second portion of the nucleotide sequence, and wherein the first and second portions of the nucleotide sequence are operably linked in the genomic polynucleotide. Particular embodiments provide a multicellular organism including such a plurality of genetically modified cells, wherein the genetically modified cells include different index sequences.

The foregoing and other features of the disclosed subject matter will become more apparent from the following detailed description, which proceeds with reference to the accompanying figures.

BRIEF DESCRIPTION OF THE DRAWINGS

A FIG. 1A-D is an overview of in situ assembly. Amplification of homology arms and cargo fragments by PCR with overlaps of about 30 bp (FIG. 1A). Optional complexing by a second round of PCR reduces the number of fragments and increases the frequency of correct integration (FIG. 1B). Upon microinjection, PCR products are recombined by the organism (e.g., a worm) using microhomology (FIG. 1C) to make the complete donor homology ready for integration (FIG. 1D).

FIGS. 3A and 3B show exemplary schematics of index directed modulation of the genome. FIG. 3A shows a genomic synthetic landing pad designed to accept indexes via homology directed repair. The index carries a portion of a selectable DNA sequence of a Hyg Resistance (HygR) cassette. Upon integration, the HygR gene (or other selectable sequence) is reconstituted. FIG. 3B shows that the injected mix of indexes generates complex DNA arrays in the animal via the TARDIS technology. The array acts as a "data compression" technology, with 1,000+ indexes being stitched together to form a single selectable array (e.g., neomycin selectable).

SEQUENCE LISTING

Figure 2:
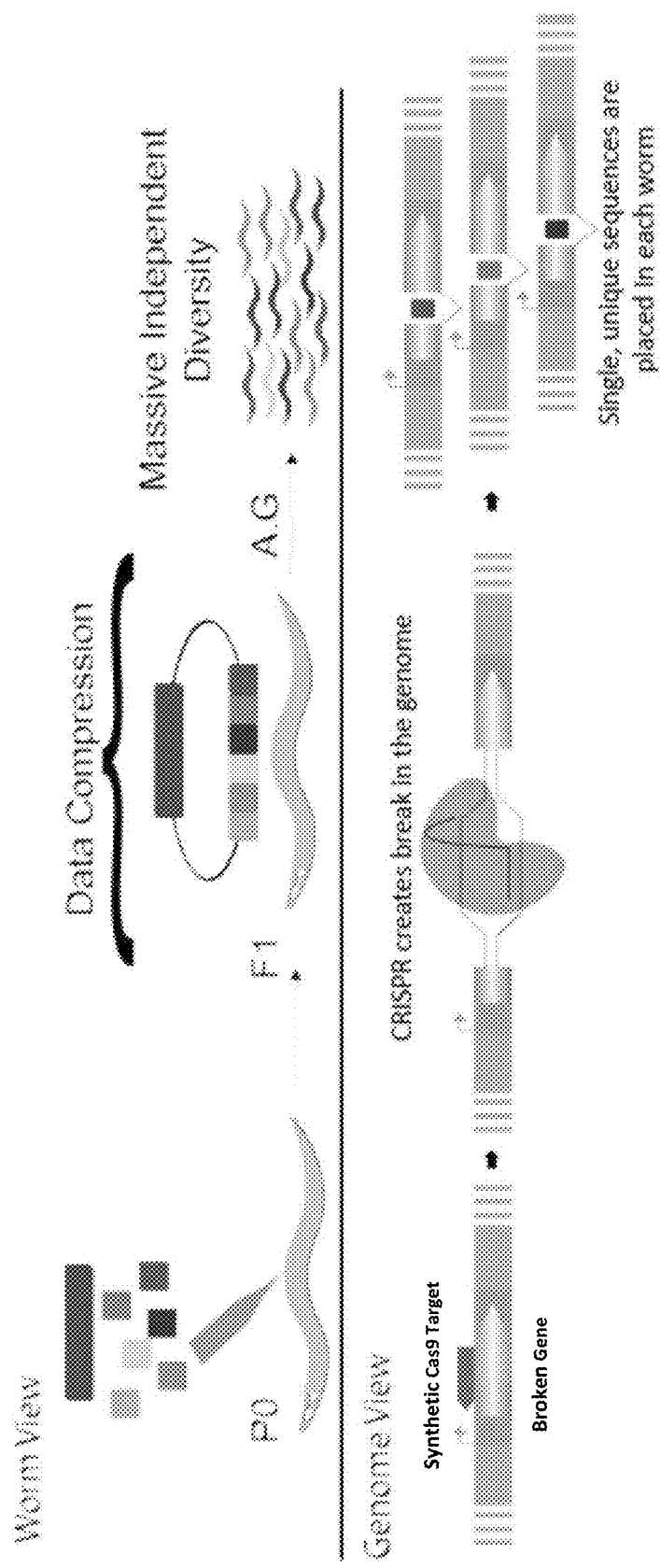
FIG. 2 is a schematic diagram of an embodiment of the technology showing production of C. elegans including an array (e.g., an artificial chromosome or in situ array) of gene fragments in the F1 generation and resulting independent diversity in progeny organisms (top). A single worm is injected with a plurality of sequences, which do not integrate immediately, but produce the array which is inherited to later generations. This population is expanded (advanced generations (A.G.)), and then CRISPR is induced when desired. Once induced, each individual worm takes a random individual sequence. For example, if 1,000 lines are desired, 1,000 unique sequences are injected to form the array. The population is then expanded until it is somewhere significantly over 1,000, and then CRISPR is induced. Each individual worm in the population will try and integrate only 1 of the 1,000 sequences. At the genomic level (bottom), the C. elegans genome includes a "broken gene" or transcription control element (e.g., a promoter), which may be a target for creating variation or a selectable marker with a cargo. This "synthetic landing pad" includes a Cas9 recognition site, such that CRISPR creates a break in the genome and unique sequences from the array of gene fragments are integrated in each progeny worm.

Any nucleic acid and amino acid sequences listed herein or in the accompanying Sequence Listing are shown using standard letter abbreviations for nucleotide bases and amino acids, as defined in 37 C.F.R. § 1.822. In at least some cases, only one strand of each nucleic acid sequence is shown, but the complementary strand is understood as included by any reference to the displayed strand.

SEQ ID NO: 1 is the nucleic acid sequence of Ultramer ZCS133, a long ssDNA oligo which serves as a template for PCR amplification. PCR amplification produces a large diverse double-stranded DNA mixture with random sequences in the place of the Ns, for example for generating barcodes for barcoded lineage tracking.

SEQ ID NOs: 2-32 are the nucleotide sequences of primer oligonucleotides utilized in the representative Examples.

SEQ ID NO: 33 is the nucleic acid sequence of a tbb-2 3'UTR.

SEQ ID NO: 34 is the nucleic acid sequence of a U6 promoter.

SEQ ID NO: 35 is the nucleic acid sequence of a gRNA scaffold from pDD162:

GTTTTAGAGCTAGAAATAGCAAGTTAAAATAAGGCTAGTCCGTTATCAA

CTTGAAAAAGTGGCACCGAGTCGGTGCTTTT

SEQ ID NO: 36 is the nucleic acid sequence of pZCS41, an exemplary U6::guideRNA plasmid for targeting the TARDIS SLP for barcoded lineage tracking.

aacactgcggccaacttacttctgacaacgatcggaggaccgaaggagctaaccgcttttttgcacaac atgggggatcatgtaactcgccttgatcgttgggaaccggagctgaatgaagccataccaaacgacgag cgtgacaccacgatgcctgtagcaatggcaacaacgttgcgcaaactattaactggcgaactacttact ctagcttcccggcaacaattaatagactggatggaggcggataaagttgcaggaccacttctgcgctcg -continued

```
gcccttccggctggctggtttattgctgataaatctggagccggtgagcgtgggtctcgcggtatcatt gcagcactggggccagatggtaagccctcccgtatcgtagttatctacacgacggggagtcaggcaact atggatgaacgaaatagacagatcgctgagataggtgcctcactgattaagcattggtaactgtcagac caagtttactcatatatactttagattgatttaaaacttcattttttaatttaaaaggatctaggtgaag atccttttttgataatctcatgaccaaaatcccttaacgtgagttttcgttccactgagcgtcagacccc gtagaaaagatcaaaggatcttcttgagatcctttttttctgcgcgtaatctgctgcttgcaaacaaaa aaaccaccgctaccagcggtggtttgtttgccggatcaagagctaccaactcttttttccgaaggtaact ggcttcagcagagcgcagataccaaatactgttcttctagtgtagccgtagttaggccaccacttcaag aactctgtagcaccgcctacatacctcgctctgctaatcctgttaccagtggctgctgccagtggcgat aagtcgtgtcttaccgggttggactcaagacgatagttaccggataaggcgcagcggtcgggctgaacg gggggttcgtgcacacagcccagcttggagcgaacgacctacaccgaactgagatacctacagcgtgag ctatgagaaagcgccacgcttcccgaagggagaaaggcggacaggtatccggtaagcggcagggtcgga acaggagagcgcacgagggagcttccaggggggaaacgcctggtatctttatagtcctgtcgggtttcgc cacctctgacttgagcgtcgatttttgtgatgctcgtcaggggggcggagcctatggaaaaacgccagc aacgcggcctttttacggttcctggccttttgctggccttttgctcacatgttctttcctgcgttatcc cctgattctgtggataaccgtattaccgcctttgagtgagctgataccgctcgccgcagccgaacgacc gagcgcagcgagtcagtgagcgaggaagcggaagagcgcccaatacgcaaaccgcctctccccgcgcgt tggccgattcattaatgcagctggcacgacaggtttcccgactggaaagcgggcagtgagcgcaacgca attaatgtgagttagctcactcattaggcaccccaggctttacactttatgcttccggctcgtatgttg tgtggaattgtgagcggataacaatttcacacaggaaacagctatgaccatgattacgccaagcttgca tgcctgcaggtcgactctagaggatcccattatacatagttgataattcactggccgtcgttttacaac gtcgtgactgggaaaaccaaaaaaaactagcaataaaggaataaaaaactgtacaccttaaaggcgcac actctgttttgcaaattttattttagttgtgaattttctgctgagacctgaaaatagcaactttagta ctactataatttgtcaacctttcaaaaaagcatgcaattttttgagaaactcttataaaagctattat taaaaaaacacctttttttccaaaattattccacaaaaaatatgttatgaaatgcctacaccctctcaca cacactctttatactactctgtcaaactcacgagatgtctgccgcctcttgtgttgccctatataaac acctcctattgcgagatgtcttGGCGAAGTGACGGTAGACCGTGTTTTAGAGCTAGAAATAGCAAGTTA AAATAAGGCTAGTCCGTTATCAACTTGAAAAAGTGGCACCGAGTCGGTGCTTTTTGTGAAATTTctggc gtaatagcgaagaggcccgcaccgatcgcccttcccaacagttgcgcagcctgaatggcgaatcgggta ccgagctcgaattcactggccgtcgttttacaacgtcgtgactgggaaaaccctggcgttacccaactt aatcgccttgcagcacatccccctttcgccagctggcgtaatagcgaagaggcccgcaccgatcgccct tcccaacagttgcgcagcctgaatggcgaatggcgcctgatgcggtattttctccttacgcatctgtgc ggtatttcacaccgcatatggtgcactctcagtacaatctgctctgatgccgcatagttaagccagccc cgacacccgccaacacccgctgacgcgccctgacgggcttgtctgctcccggcatccgcttacagacaa gctgtgaccgtctccgggagctgcatgtgtcagaggttttcaccgtcatcaccgaaacgcgcgagacga aagggcctcgtgatacgcctatttttataggttaatgtcatgataataatggtttcttagacgtcaggt ggcacttttcggggaaatgtgcgcggaacccctatttgtttatttttctaaatacattcaaatatgtat ccgctcatgagacaataaccctgataaatgcttcaataatattgaaaaaggaagagtatgagtattcaa catttccgtgtcgcccttattcccttttttgcggcattttgccttcctgttttgctcacccagaaacg ctggtgaaagtaaaagatgctgaagatcagttgggtgcacgagtgggttacatcgaactggatctcaac agcggtaagatccttgagagttttcgccccgaagaacgttttccaatgatgagcacttttaaagttctg
```

```
ctatgtggcgcggtattatcccgtattgacgccgggcaagagcaactcggtcgccgcatacactattct cagaatgacttggttgagtactcaccagtcacagaaaagcatcttacggatggcatgacagtaagagaa ttatgcagtgctgccataaccatgagtgat
```

SEQ ID NO: 37 is the nucleotide sequence of a synthetic SSN recognition site.

GCGAAGTGACGGTAGACCGT

SEQ ID NO: 38 is the nucleotide sequence of a gRNA targeting the GT300 synthetic site.

GGACAGTCCTGCCGAGGTGG

SEQ ID NO: 39 is the nucleotide sequence of the HYGRΔ3'::unc-54 3' UTR.
SEQ ID NO: 40 is the nucleotide sequence of eft-3p.
SEQ ID NO: 41 is the nucleotide sequence of wrmScarlet.
SEQ ID NO: 42 is the nucleotide sequence of a gRNA targeting the PX696 landing pad:

GACAGTCCTGCCGAGGTGG

SEQ ID NO: 43 is the nucleotide sequence of the PX696 landing pad:

```
CACTCGTTTAGGCTATTCCCCTATTTTTGATATTCCTTCGCACATATGAAA
ACTACTTTTTTTCGAAACTGTTAACTCCAGAATTTATAAATCTATAGCCCT
TACTTGATTATTTATTATCATGGTTACTCACCTCATGTCTCTTTCTCTTTT
CAAGAAGTCTTCGTTCATATCTGTTGTCTCTTTCCTCCTTTTGAATCTCTG
CTTTGCTCTTCGCCATTGTTTCCTGAAAATAATGTAACTTGAATTGTGTAA
TATACTTTTTTAATTTGAATTTGGCTTGTAACGCGGAATCACTACGTGCGG
GATCATTTCTTACTAGAAAACCCAGAAAATGCCATATTTCACTTATCTCGG
GGTCATTTCTAATTAGAAAAGCTACAAAAACCATTTCTAATTACGGTGACT
TTAGAACTGGTCGAAATAGCTAATTAGAAATGGGTTTTTGCTAATTAGAGG
TGACTCTATGTTATCTGAGTAAGCCTCGTTTGTATGTAAACTCACAGTACT
AATAAATGCAAGACACCCGGGTTTGTCTAGATATGAAATAATTGAAATATC
AATTCTGACAGACAATAATGGTAATCTTGATAAGGAGTTCCACGCCCAGGA
GAACACGTTAGTTTTCTTGTTTTTGATTGCGTGCGTTATTTTGGAGAAAAA
CTCGATTTTTTACAAAATAATTTTTTGAAAGGAACACTGTTCAATAAGTTT
TGTCTTTTTTCTCAGTTGTGATACGGTTTTTTATTCTTTTTTGTAGTTATA
CAGAAGACCGCCTGCAGGGACAGTCCTGCCGAGGTGGAGGgaccgttacg
tctaccgtcacttcgcctccccgccctcccaatcccagaggtcctcgaca
tcggagagttctccgagtccctcacctactgcatctcccgtcgtgcccaag
gagtcaccctccaagacctcccagagaccgagctcccagccgtcctccaac
cagtcgccgaggccatggacgccatcgccgccgccgacctctcccaaacct
ccggattcggaccattcggaccacaaggaatcggacaatacaccacctggc
gtgacttcatctgcgccatcgccgacccacacgtctaccactggcaaaccg
tcatggacgacaccgtctccgcctccgtcgcccaagccctcgaccagctca
tgctctgggccgacgactgcccagaggtccgtcacctcgtccacgccgact
tcggatccaacaacgtcctcaccgacaacggacgtatcaccgccgtcatcg
actcgtccgaggccatgttcggagactcccaataccaggtcccaacatct
tcttctggcgtccatggctcgcctgcatggagcaacaaacccgttacttcg
agcgtcgtcacccagagctcgccggatcccacgtctccgtgcctacatgc
tccgtatcggactcgaccaactctaccaatccctcgtccacggaaacttcg
acgacgccgcctgggcccaaggacgttgcgacgccatcgcccgttccggag
ccggaaccgtcggacgtacccaaatcgccctcgttccgccgccgtctgga
ccgaccgatgcctcgagctcctcgccgactccggaaaccgtcgtccatcca
cccgtccacgtgccaaggagtaaGTCCAATTACTCTTCAACATCCCTACAT
GCTCTTTCTCCCTGTGCTCCCACCCCCTATTTTTGTTATTATCAAAAAACT
TCTCTTAATTTCTTTGTTTTTTAGCTTCTTTTAAGTCACCTCTAACAATGA
AATTGTGTAGATTCAAAAATAGAATTAATTCGTAATAAAAAGTCGAAAAAA
ATTGTGCTCCCTCCCCCCATTAATAATAATTCTATCCCAAAATCTACACAA
TGTTCTGTGTACACTTCTTATGTTTTTTACTTCTGATAAATTTTTTTGAAA
CATCATAGAAAAAACCGCACACAAAATACCTTATCATATGTTACGTTTCAG
TTTATGACCGCAATTTTTActagtgcaggagctgtaagtttaaaATAACTT
CGTATAGCATACATTATACGAAGTTATtttcagGGAGCCGGATCT
```

SEQ ID NO: 44 is the nucleotide sequence of pDSP57, containing split mScarlet donor homology sequences:

```
GCCATTGTCCGTCAGGACATTGTTGGAGCCGAAATCCGCGTGCACGAGGTG
CCGGACTTCGGGGCAGTCCTCGGCCCAAAGCATCAGCTCATCGAGAGCCTG
CGCGACGGACGCACTGACGGTGTCGTCCATCACAGTTTGCCAGTGATACAC
ATGGGGATCAGCAATCGCGCATATGAAATCACGCCATGTAGTGTATTGACC
GATTCCTTGCGGTCCGAATGGGCCGAACCCGCTCGTCTGGCTAAGATCGGC
CGCAGCGATCGCATCCATGGCCTCCGCGACCGGCTGCAGAACAGCGGGCAG
TTCGGTTTCAGGCAGGTCTTGCAACGTGACACCCTGTGCACGGCGGGAGAT
GCAATAGGTCAGGCTCTCGCTGAATTCCCCAATGTCAAGCACTTCCGGAAT
CGGGAGCGCGGCCGATGCAAAGTGCCGATAAACATAACGATCTTTGTAGAA
ACCATCGGCGCAGCTATTTACCCGCAGGACATATCCACGCCCTCCTACATC
GAAGCTGAAAGCACGAGATTCTTCGCCCTCCGAGAGCTGCATCAGGTCGGA
GACGCTGTCGAACTTTTCGATCAGAAACTTCTCGACAGACGTCGCGGTGAG
TTCAGGCTTTTTCATGGAGGCTGCTTTTTTGTACAAACTTGCGGCACCGCC
TGACATATTACCTTAAAATTCAAAAATTAATTTCAGATCAGTCATAACCAA
```

```
GAAAACAAAATAAACGTTAGGACAGAAAATTCAAATTAATTAAAAATTATG
CTGAATAAGAAAATTACATGCAAAGCCTTATTTTCCTCATAGAAACAGTTG
AATAACATATTTTTTAATTGAAAACATAGCAAAATTCGTGGTAAAATTTGT
CAAAACCTTGGAAAAAATCGAAAAAAGAACATTTCCCGATGCATTTTCCTA
TTTCTCGTTGCCGACAACGTATAAACGTTGAATACTCAGTCAACGAATTTG
GCTGCTGGCTTGGACTCTCGCACGGAAGAGACGCGTGTGTAGATTTAcgac
gaaagcaaaaatATAACTTCGTATAGCATACATTATACGAAGTTAT*GTAAA*
*ACGACGGCCAGTCCGTAATACGACTCACTTAAGG*gatcaccaaaaacggaa
cgttgagctggacggaaatagtggtaaagtgacatgattatagtttgaaga
tttctaatttcacaattagagcaaatgttgttcggtatttattttcaacgg
tatttatactattttccaccttttttctagaacattcgagctgcttgttgca
aaaggagggcgactcacattcggtacatggaaaagtagtgtacacaataaa
gagacccagatacattttccgtctgcgtctctttgcacccaccgagagtat
tttcaaacgaatgcatctaggaccttctagaacattctgtaaggctgcaga
atgcgggtatataaggaaagcgggctcagaggaagccaacacgctttgttc
tagtgcatctaaaaaacttcgaaaatATGGTTTCCAAGGGAGAGGCTGTTA
TCAAGGAATTCATGACTTACCCAAAGAAGAAGCGTAAGGTCGAACTTATCA
AGGAGTTTATGCGCTTTAAGGTTCACATGGAAGGATCTATGAACGGACACG
AATTCGAAATCGAAGGAGAAGGAGAAGGACGTCCATACGAGGGAACTCAAA
CTGCTAAGCTTAAGGTAAGTTTATCTAAAAAGTTTTTCATTCAAAATGTGT
AAAAATTCATTTAAAATAACCCAAAAATCATTAATCCTCGATATTTTCAGG
TTACTAAAGGAGGACCACTTCCATTCTCTTGGGATATCCTTTCTCCACAAT
TCATGTACGGATCTCGCGCTTTCATCAAGCACCCAGCTGATATCCCAGATT
ACTACAAGCAATCTTTCCCAGAAGGATTCAAATGGGAGCGTGTTATGAACT
TCGAAGATGGAGGAGCTGTTACCGTTACCCAAGATACCTCCCTTGAGGATG
GAACCCTTATCTACAAGGTATTTTCCTGCATTTTTCAACTGGGAAAATGAA
AGAAAATCGATAATTTCAGGTTAAGCTTCGTGGAACTAATTTCCCACCAGA
TGGACCAGTTATGCAAAAGAAGACTATGGGATGGGAGGCTTCTACCGAGCG
CCTTTACCCAGAGGATGGAGTCCTTAAGGGAGATATCAAGATGGCTCTTCG
TCTTAAGGATGGAGGACGTTACCTTGCTGATTTCAAGGTAAGTTTTCTAGA
GACCTTTACTAACTAACTAGGTCTCATAGATTTTCAGACTACTTACAAGGC
TAAGAAGCCAGTT
```

SEQ ID NO: 45 is the nucleotide sequence of the pDSP58, containing split unc-119 donor homology sequences:

```
gttgctccgaccgttttgagtttcaaaaagtttggagcaaatctataacgc
acgtatcttgccgactcctgtggcgactcatcattctcctgatcgttctcc
ggtttggcgatctcgaaaagcacttgctcagtgtccagatcacggatttgg
aacttggtgaactcgatgttatagatgttcgcagatgggagcataagaat
cctaaatttatgttttaaactgaaatccaaagggagcaagataccttgagt
gattcccggaagtgctaaaacgtcgttcggagtgatttgagctttcttcgc
aagctccgattccgttgtgattccttgttcggtgcttggtggtggccgtgg
catctggaaatatggaaaagttcaacaaaaagaaaagagaaaagaatgaaa
tcggatatcaagagttagttgagcggtttctctagttttctgagtctcacc
tgcgacgggaaggtcgccgagccgggtggaatcgatCgttgttgctcggct
ttcatatcggtttggttggaagcggctgaaaacggaaagaagtggaagaag
gaaaagagtgtggtgtgacaggaaaatggtaattagagggtgccaaataac
cagctatattttgttttttttgaaaacattttttaaaaagaaaaatacgat
aatgatatcagatggatttccggaaaactggtatgaaaaatttcaacctttt
ttgagtacatgtaatcaaaatacactttgtaaattatcattttttattgaaa
ctccaccattttttctatttataacgctaataatttgaaaaagaaacctAtt
gcgaaccgcgggtgaatcccaaaaacgaatgcgttttggtggagtgattg
attcgaatcgaagaagaaaaagaagaagacgtggaatagagagctcactct
taaccgagcagcacacaccgacagaaaaaaaatgaaatgaatgagggtct
tcttcttcttctccgaatgattgacagaaatgggaaaaagaggaagat
tgagaagggaaaaaggaaggagaaaagaagcagaagaagacgtcagagagg
agaggaacgagcggaaaagcagcgggcgcaagtcatagaagtagcagagct
ggggagaagaagacactatccaagaaaggaatgacgagagagtatgcaaag
gggtatagggtgcagacagaataggaacagaataacagatgatgagccaag
aagagttgaaaagggcgatgaatttgtcatgtaacttaatttgggtcaatt
tgagcatgatgaattgaaatcatcccttgtgggagttaataaccggtttg
ttatcagaaaccctgtaatagaagggcgccctaactttgagccaattcatc
ccggtttctgtcaaatatatcaaaaagtggtcaactgacaaattgttttttg
atattataataaacattttatccgttaacaattttcgaatactttttacaa
ggacttggataaattggctcaATAACTTCGTATAGTATACCTTATACGAAG
TTATGT*AAAACGACGGCCAGTCCGTAATACGACTCACTTAAGG*gatcacca
aaaacggaacgttgagctggacggaaatagtggtaaagtgacatgattata
gtttgaagatttctaatttcacaattagagcaaatgttgttcggtatttat
tttcaacggtatttatactattttccaccttttttctagaacattcgagctg
cttgttgcaaaaggagggcgactcacattcggtacatggaaaagtagtgta
cacaataaagagacccagatacattttccgtctgcgtctctttgcacccac
cgggagtattttcaaacgaatgcatctaggaccttctagaacattctgtaa
ggctgcagaatgcgggtatataaggaaagcgggctcagaggaagccaacac
gcttcgttctagtgcatctaaaaaacttcgaaaatATGGTTTCCAAGGGAG
AGGCTGTTATCAAGGAATTCATGACTTACCCAAAGAAGAAGCGTAAGGTCG
GAGAAGAGGACAACATGGCTTCTCTTCCAGCTACTCACGAACTTCATATTT
TCGGATCTATCAACGGAGTTGATTTCGATATGGTTGGACAAGGAACTGGAA
ACCCAAACGACGGATACGAAGAGCTTAACCTTAAGTCTACCAAGGTAAGTT
TATCTAAAAAGTTTTTCATTCAAAATGTGTAAAAATTCATTTAAAATAACC
CAAAAATCATTAATCCTCGATATTTTCAGGGAGATCTTCAATTCTCTCCAT
GGATCCTTGTTCCACACATTGGATACGGATTCCACCAATACCTTCCATACC
```

```
CAGATGGAATGTCTCCATTCCAAGCTGCTATGGTTGACGGATCTGGATACC

AAGTTCACCGTACTATGCAATTCGAGGACGGAGCTTCCCTCACCGTCAACT

ACCGTTACACTTACGAAGGATCTCACATCAAGGTATTTTCCTGCATTTTTC

AACTGGGAAAATGAAAGAAAATCGATAATTTCAGGGAGAAGCTCAAGTTAA

GGGAACCGGATTCCCAGCCGATGGACCAGTTATGACCAACTCTCTTACCGC

CGCTGATTGGTGCCGCTCTAAGAAGACCTACCCAAACGATAAGGTAAGTTT

TCTAGAGACCTTTACTAACTAACTAGGTCTCATAGATTTTCAGACTATCAT

CTCTACTTTCAAG7GGTCTTACACTACCGGAAACGGAAAGCGTTACCGCTC

TACCGCTCGCACTACTTACACTTTCGCTAAGCCAATGGCTGCCAACTAC
```

SEQ ID NO: 46 is the nucleotide sequence of a 500 bp donor homology insert from PX742:

```
CGCGTCTCTTCCGTGCGAGAGTCCAAGCCAGCAGCCAAATTCGTTGACTGA

GTATTCAACGTTTATACGTTGTCGGCAACGAGAAATAGGAAAATGCATCGG

GAAATGTTCTTTTTTCGATTTTTTCCAAGGTTTTGACAAATTTTACCACGA

ATTTTGCTATGTTTTCAATTAAAAAATATGTTATTCAACTGTTTCTATGAG

GAAAATAAGGCTTTGCATGTAATTTTCTTATTCAGCATAATTTTTAATTAA

TTTGAATTTTCTGTCCTAACGTTTATTTTGTTTTCTTGGTTATGACTGATC

TGAAATTAATTTTTGAATTTTAAGGTAATATGAAAAAACCCGAGTTGACCG

CCACATCCGTAGAGAAGTTCCTCATCGAGAAGTTCGACTCCGTCTCCGACC

TCATGCAACTCTCCGAGGGAGAGGAGTCCCGTGCCTTCTCCTTCGACGTCG

GAGGACGTGGATACGTCCTCCGTGTCAACTCCTGCGCCGACGGATTCTACA

AGGTAAGTTTAAACATATNNNNNNNNNNNNNNNNTATTTAAATTTTCAGGAC

CGTTACGTCTACCGTCACTTCGCCTCCGCCGCCCTCCCAATCCCAGAGGTC

CTCGACATCGGAGAGTTCTCCGAGTCCCTCACCTACTGCATCTCCCGTCGT

GCCCAAGGAGTCACCCTCCAAGACCTCCCAGAGACCGAGCTCCCAGCCGTC

CTCCAACCAGTCGCCGAGGCCATGGACGCCATCGCCGCCGCCGACCTCTCC

CAAACCTCCGGATTCGGACGATTCGGACCACAAGGAATCGGACAATACACC

ACCTGGCGTGACTTCATCTGCGCCATCGCCGACCCACACGTCTACCACTGG

CAAACCGTCATGGACGACACCGTCTCCGCCTCCGTCGCCCAAGCCCTCGAC

GAGCTCATGCTCTGGGCCGAGGACTGCCCAGAGGTCCGTCACCTCGTCCAC

GCCGACTTCGGATCCAACAACGTCCTCACCGACAACGGACGTATCACCGCC

GTCATCGACTGGTCCGAGGCCATGTTCGGAGACTCCCAATACGAGGTC
```

SEQ ID NO: 47 is the 501 bp pZCS32 nucleotide sequence amplified with primers ZCS276 and ZCS278:

```
GTCTACCGTCACTTCGCCTCCGCCGCCCTCCCAATCCCAGAGGTCCTCGAC

ATCGGAGAGTTCTCCGAGTCCCTCACCTACTGCATCTCCCGTCGTGCCCAA

GGAGTCACCCTCCAAGACCTCCCAGAGACCGAGCTCCCAGCCGTCCTCCAA

CCAGTCGCCGAGGCCATGGACGCCATCGCCGCCGCCGACCTCTCCCAAACC

TCCGGATTCGGACCATTCGGACCACAAGGAATCGGACAATACACCACCTGG

CGTGACTTCATCTGCGCCATCGCCGACCCACACGTCTACCACTGGCAAACC

GTCATGGACGACACCGTCTCCGCCTCCGTCGCCCAAGCCCTCGACGAGCTC

ATGCTCTGGGCCGAGGACTGCCCAGAGGTCCGTCACCTCGTCCACGCCGAC

TTCGGATCCAACAACGTCCTCACCGACAACGGACGTATCACCGCCGTCATC

GACTGGTCCGAGGCCATGTTCGGAGACTCCCAATACGAGGTC
```

SEQ ID NO: 48 is the 501 bp pZCS32 nucleotide sequence amplified with primers ZCS273 and ZCS275:

```
CGCGTCTCTTCCGTGCGAGAGTCCAAGCCAGCAGCCAAATTCGTTGACTGA

GTATTCAACGTTTATACGTTGTCGGCAACGAGAAATAGGAAAATGCATCGG

GAAATGTTCTTTTTTCGATTTTTTCCAAGGTTTTGACAAATTTTACCACGA

ATTTTGCTATGTTTTCAATTAAAAAATATGTTATTCAACTGTTTCTATGAG

GAAAATAAGGCTTTGCATGTAATTTTCTTATTCAGCATAATTTTTAATTAA

TTTGAATTTTCTGTCCTAACGTTTATTTTGTTTTCTTGGTTATGACTGATC

TGAAATTAATTTTTGAATTTTAAGGTAATATGAAAAAACCCGAGTTGACCG

CCACATCCGTAGAGAAGTTCCTCATCGAGAAGTTCGACTCCGTCTCCGACC

TCATGCAACTCTCCGAGGGAGAGGAGTCCCGTGCCTTCTCCTTCGACGTCG

GAGGACGTGGATACGTCCTCCGTGTCAACTCCTGCGCCGACG
```

SEQ ID NO: 49 is the nucleotide sequence of the 150 bp left homology arm of pZCS32, amplified with primers ZCS285 and ZCS275:

```
TGACCGCCACATCCGTAGAGAAGTTCCTCATCGAGAAGTTCGACTCCGTCT

CCGACCTCATGCAACTCTCCGAGGGAGAGGAGTCCCGTGCCTTCTCCTTCG

ACGTCGGAGGACGTGGATACGTCCTCCGTGTCAACTCCTGCGCCGACG
```

SEQ ID NO: 50 is the nucleotide sequence of the 150 bp right homology arm of pZCS32, amplified with primers ZCS276 and ZCS286:

```
TGACCGCCACATCCGTAGAGAAGTTCCTCATCGAGAAGTTCGACTCCGTCT

CCGACCTCATGCAACTCTCCGAGGGAGAGGAGTCCCGTGCCTTCTCCTTCG

ACGTCGGAGGACGTGGATACGTCCTCCGTGTCAACTCCTGCGCCGACG
```

SEQ ID NO: 51 is the nucleotide sequence of the pZCS32 landing pad (prsp-0::ΔHygR1::synthetic guide::ΔHygR2::unc-54UTR::LoxP):

```
ATTTTTGCTTTCGTCGTAAATCTACACACGCGTCTCTTCCGTGCGAGAGTC

CAAGCCAGCAGCCAAATTCGTTGACTGAGTATTCAACGTTTATACGTTGTC

GGCAACGAGAAATAGGAAAATGCATCGGGAAATGTTCTTTTTTCGATTTTT

TCCAAGGTTTTGACAAATTTTACCACGAATTTTGCTATGTTTTCAATTAAA

AAATATGTTATTCAACTGTTTCTATGAGGAAAATAAGGCTTTGCATGTAAT

TTTCTTATTCAGCATAATTTTTAATTAATTTGAATTTTCTGTCCTAACGTT

TATTTTGTTTTCTTGGTTATGACTGATCTGAAATTAATTTTTGAATTTTAA

GGTAATATGAAAAAACCCGAGTTGACCGCCACATCCGTAGAGAAGTTCCTC

ATCGAGAAGTTCGACTCCGTCTCCGACCTCATGCAACTCTCCGAGGGAGAG
```

```
GAGTCCCGTGCCTTCTCCTTCGACGTCGGAGGACGTGGATACGTCCTCCGT

GTCAACTCCTGCGCCGACGGTCTACCGTCACTTCGCCTCCGCCGCCCTCCC

AATCCCAGAGGTCCTCGACATCGGAGAGTTCTCCGAGTCCCTCACCTACTG

CATCTCCCGTCGTGCCCAAGGAGTCACCCTCCAAGACCTCCCAGAGACCGA

GCTCCCAGCCGTCCTCCAACCAGTCGCCGAGGCCATGGACGCCATCGCCGC

CGCCGACCTCTCCCAAACCTCCGGATTCGGACCATTCGGACCACAAGGAAT

CGGACAATACACCACCTGGCGTGACTTCATCTGCGCCATCGCCGACCCACA

CGTCTACCACTGGCAAACCGTCATGGACGACACCGTCTCCGCCTCCGTCGC

CCAAGCCCTCGACGAGCTCATGCTCTGGGCCGAGGACTGCCCAGAGGTCCG

TCACCTCGTCCACGCCGACTTCGGATCCAACAACGTCCTCACCGACAACGG

ACGTATCACCGCCGTCATCGACTGGTCCGAGGCCATGTTCGGAGACTCCCA

ATACGAGGTCGCCAACATCTTCTTCTGGCGTCCATGGCTCGCCTGCATGGA

GCAACAAACCCGTTACTTCGAGCGTCGTCACCCAGAGCTCGCCGGATCCCC

ACGTCTCCGTGCCTACATGCTCCGTATCGGACTCGACCAACTCTACCAATC

CCTCGTCGACGGAAACTTCGACGACGCCGCCTGGGCCCAAGGACGTTGCGA

CGCCATCGTCCGTTCCGGAGCCGGAACCGTCGGACGTACCCAAATCGCCCG

TCGTTCCGCCGCCGTCTGGACCGACGGATGCGTCGAGGTCCTCGCCGACTC

CGGAAACCGTCGTCCATCCACCCGTCCACGTGCCAAGGAGTAAGTCCAATT

ACTCTTCAACATCCCTACATGCTCTTTCTCCCTGTGCTCCCACCCCCTATT

TTTGTTATTATCAAAAAACTTCTCTTAATTTCTTTGTTTTTTAGCTTCTTT

TAAGTCACCTCTAACAATGAAATTGTGTAGATTCAAAAATAGAATTAATTC

GTAATAAAAAGTCGAAAAAAATTGTGCTCCCTCCCCCCATTAATAATAATT

CTATCCCAAAATCTACACAATGTTCTGTGTACACTTCTTATGTTTTTTACT

TCTGATAAATTTTTTTGAAACATCATAGAAAAAACCGCACACAAAATACCT

TATCATATGTTACGTTTCAGTTTATGACCGCAATTTTTAgtaagtttaaaA

TAACTTCGTATAGCATACATTATACGAAGTTATtttcag
```

SEQ ID NO: 52 is the nucleotide sequence of the PX743 array library:

```
TGACCGCCACATCCGTAGAGAAGTTCCTCATCGAGAAGTTCGACTCCGTCT

CCGACCTCATGCAACTCTCCGAGGGAGAGGAGTCCCGTGCCTTCTCCTTCG

ACGTCGGAGGACGTGGATACGTCCTCCGTGTCAACTCCTGCGCCGACGGAT

TctacaaggtaagtttaaacatatgcccgggcGAGTCataatACACTCTTT

CCCTACACGACGCTCTTCCGATCTNNNNNNNNNNNNNNNNAGATCGGAAGAG

CACACGTCTGAACTCCAGTCACattatGACTCgcccgggctatttaaattt tcaggaccgtTACGTCTACCGTCACTTCGCCTCCGCCGCCCTCCCAATCCC

AGAGGTCCTCGACATCGGAGAGTTCTCCGAGTCCCTCACCTACTGCATCTC

CCGTCGTGCCCAAGGAGTCACCCTCCAAGACCTCCCAGAGACCGAGCTCCC

AGCCGTCCTC
```

Figure 6:
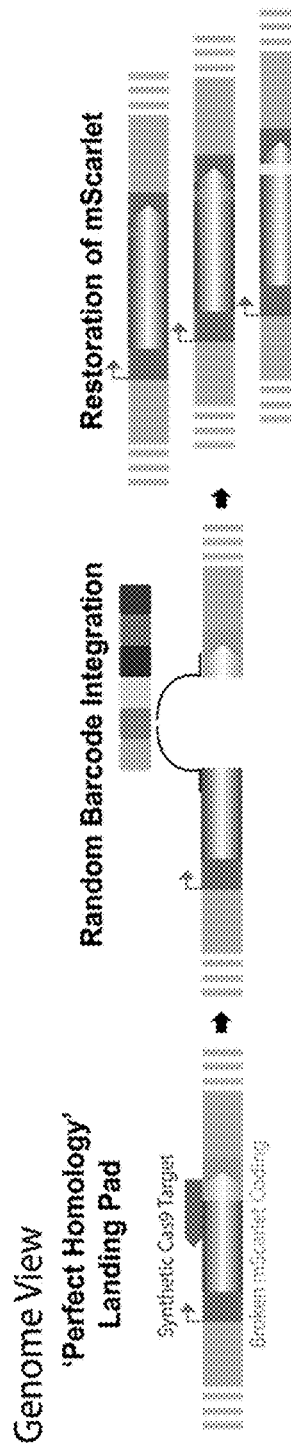
FIG. 6 includes a diagram showing the creation and marking of individuals utilizing a TARDIS landing pad design. In this example, an organism's genome contains a landing pad characterized by a genomic polynucleotide (positive sense strand DNA (SEQ ID NO: 53); negative sense strand DNA (SEQ ID NO: 54); translation (SEQ ID NO: 55)) including a Cas9 recognition site ("synthetic Cas9 target") followed by a 3' fragment of a reporter gene (mScarlet) (left). A Cas9 induces a DNA break at the recognition site (positive sense strand DNA (SEQ ID NO: 56); negative sense strand DNA (SEQ ID NO: 57); translation (SEQ ID NO: 58)), which is then repaired by homology directed repair (HDR) to integrate a single, random index sequence (e.g., a random barcode) and the 5' fragment of the reporter gene from an array of index sequences (middle). Integration of the index sequence (positive sense strand DNA (SEQ ID NO: 59); negative sense strand DNA (SEQ ID NO: 60); translation (SEQ ID NO: 61)) therefore reconstitutes the functional mScarlet reporter, allowing selection of an individual with an integrated index sequence (right). By selecting a plurality of cells descended from the cell containing the array, a library of individual cells that each contain a single index sequence from the array is generated.
Figure 7:
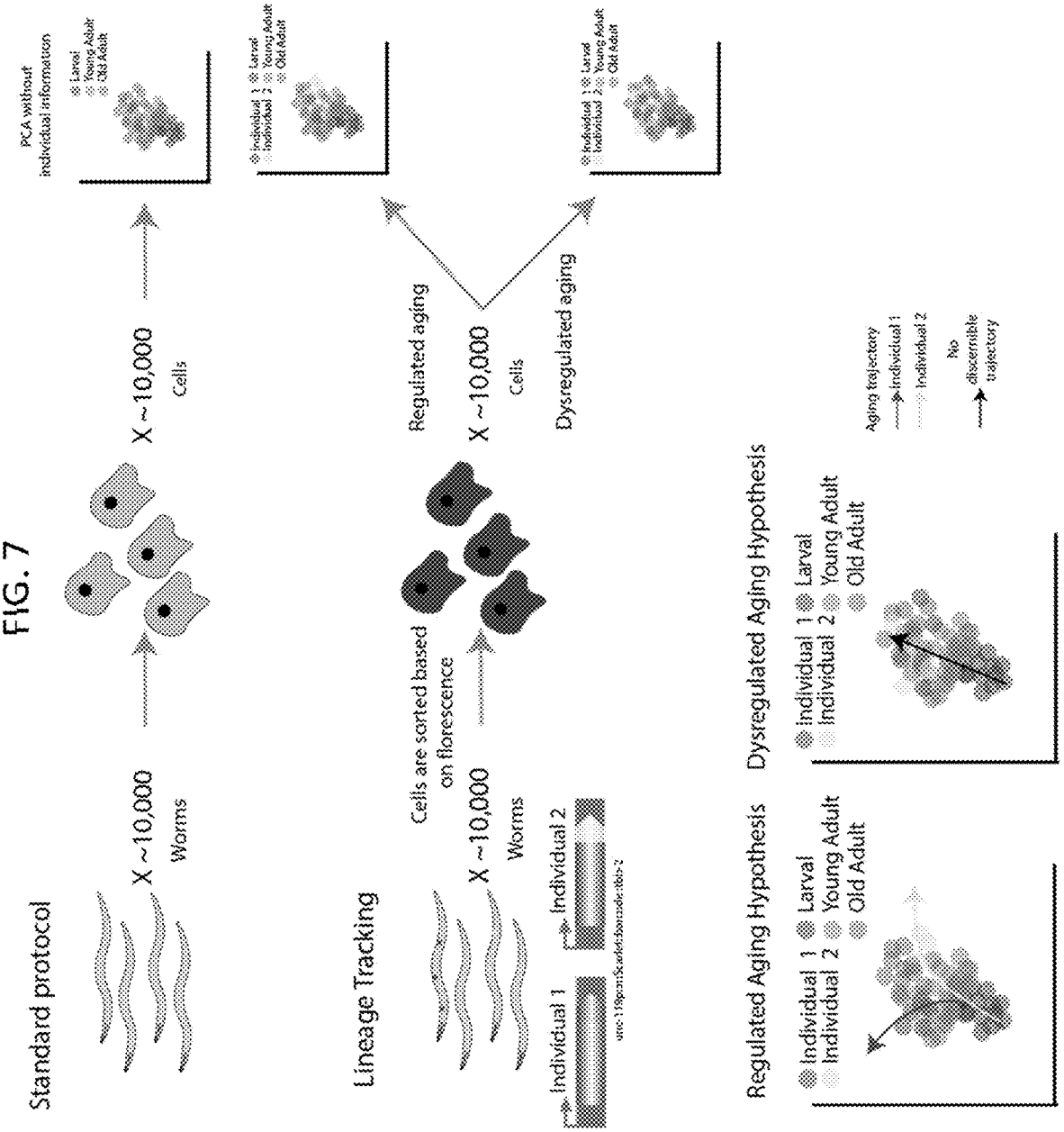
FIG. 7 illustrates an exemplary method for detecting individuals using single-cell sequencing of individuals marked on the mRNA level, as compared to existing methods for single-cell sequencing, in a process of studying aging. In existing methods (top), the lineage of particular cells from transformed worms is not able to be identified and tracked. In such methods, it is impossible to discern from a population of cells descended from transformants which cells in different stages of growth are descended from particular transformants, because there is no mRNA "barcode" identifying individual transformants. According to methods disclosed herein (middle), an mRNA barcode corresponding to particular index sequences identifies individual transformed cells, which can then be used to identify their progeny cells at different stages of growth. The "regulated aging" hypothesis postulates that the lineages of different barcoded individuals will be directed to particular cell types during aging (bottom left). On the other hand, the "dysregulated aging" null hypothesis is that particular cell types during aging will contain cells descended from random individual transformants (bottom right). Using the methods provided herein, it is possible to test the regulated aging hypothesis in complex multicellular organisms.

SEQ ID NOs: 53-61 are illustrative sequences shown in FIG. 6 for the purpose of diagraming a strategy for creation and marking of individuals utilizing a TARDIS landing pad design.

DETAILED DESCRIPTION

Unless otherwise noted, technical terms are used according to conventional usage. Definitions of common terms in molecular biology may be found in *Lewin's Genes X*, ed. Krebs et al., Jones and Bartlett Publishers, 2009 (ISBN 0763766321); Kendrew et al. (eds.), *The Encyclopedia of Molecular Biology*, published by Blackwell Publishers, 1994 (ISBN 0632021829); Robert A. Meyers (ed.), *Molecular Biology and Biotechnology: a Comprehensive Desk Reference*, published by Wiley, John & Sons, Inc., 1995 (ISBN 0471186341); and George P. Rédei, *Encyclopedic Dictionary of Genetics, Genomics, Proteomics and Informatics*, $3^{rd}$ Edition, Springer, 2008 (ISBN: 1402067534), and other similar references.

Unless otherwise explained, all technical and scientific terms used herein have the same meaning as commonly understood by one of ordinary skill in the art to which this disclosure belongs. The singular terms "a," "an," and "the" include plural referents unless the context clearly indicates otherwise. "Comprising A or B" means including A, or B, or A and B. It is further to be understood that all base sizes or amino acid sizes, and all molecular weight or molecular mass values, given for nucleic acids or polypeptides are approximate, and are provided for description.

Although methods and materials similar or equivalent to those described herein can be used in the practice or testing of the present disclosure, suitable methods and materials are described below. All publications, patent applications, patents, and other references mentioned herein are incorporated by reference in their entirety, as are the GenBank Accession numbers (for the sequences present in GenBank on Mar. 26, 2020). In case of conflict, the present specification, including explanations of terms, will control. In addition, the materials, methods, and examples are illustrative only and not intended to be limiting.

Overview of Several Embodiments

Provided herein are compressed nucleic acid sequences (e.g., arrays) and target genomic loci (e.g., landing pads) that can be utilized for genomic analysis and manipulation, among other uses. This system, referred to in some embodiments as Transgenic Arrays Resulting in Diversity of Integrated Sequences ("TARDIS") is applicable in any biological system in which genetically diverse, heritable DNA elements can be generated. When utilized in animal systems, including bacteria, yeast, *C. elegans*, fish, and mammalian systems, TARDIS provides a library-based transgenic approach that rivals the throughput of microbial and cell culture methods. TARDIS facilitates high throughput transgenesis in animals by using two engineered components, a heritable DNA array that carries a library of index sequences for integration, and a genomic landing pad that facilitates integration of single sequence units from the library. An advantage of the disclosed TARDIS data compression system is the ability to generate large numbers of novel genetic variants without the need to create and integrate individual sequences one at a time, as in traditional transgenesis systems.

The features of the disclosed systems include "compressed" DNA sequences. For example, in some embodiments applying TARDIS to *Caenorhabditis elegans*, TARDIS utilizes artificial chromosomes, or arrays, as a "compressed" nucleic acid molecular library comparable to synthetic libraries used in microbial systems. *C. elegans* arrays are known to be large in size, and generally are 1-2 MB (Woglar et al. (2020) *PLOS Biology* 18(8), e3000817). Unlike plasmids, artificial chromosomes do not require specific sequences to form and replicate, which allows for experimental flexibility in the composition. Arrays can be inherited, but do not follow typical Mendelian inheritance. Because experimental composition is highly flexible, selectable genes can be added to the array to select for only progeny that inherit the array.

The second component of the TARDIS integration system relies on a pre-integrated "landing pad" sequence. Landing pads are engineered locations in the genome, which facilitate future integrations of single sequence units from the heritable library/array. In some embodiments, the landing pad contains components needed to express the "compressed" sequence. These features, combined with a library of compressed sequences (e.g., within an artificial chromosome or within a native chromosomal location) allows for experimental diversity not previously possible with other transgenic methodologies.

In some embodiments, the compressed index sequences include a gene or promoter fragment that is not functional until combined with a second fragment in the landing pad by integration of the index sequence. For example, an index sequence and a landing pad may each comprise half of a split selectable gene, for example, a gene that encodes antibiotic (e.g., Hygromycin B) resistance. The landing pad can generally be targetable from any nuclease or recombinase that either creates a double-strand break, or recombines synthetic sequence into the genome at a recognition site. In some embodiments, the landing pad is targeted by Cas9.

In some embodiments, provided herein are methods of producing a plurality of genetically modified cells, which include introducing a nucleic acid molecule comprising a plurality of index sequences into a cell comprising a synthetic landing pad, wherein each of the plurality of index sequences comprises a first portion of a sequence and the synthetic landing pad comprises a second portion of the sequence, to produce a cell comprising the synthetic landing pad and the nucleic acid molecule comprising the plurality of index sequences. The method also includes generating a plurality of cells comprising the synthetic landing pad and the nucleic acid molecule comprising the plurality of index sequences (for example by allowing the cells to proliferate or expanding the cell population), integrating one of the plurality of index sequences into the synthetic landing pad in each of the plurality of cells, thereby linking the first and second portions of the sequence, and selecting cells comprising the integrated index sequence based on presence or activity of the linked first and second portions of the sequence, thereby producing a plurality of genetically modified cells.

In particular examples, the sequence is a non-functional gene and the first portion and the second portion reconstitute a functional gene when linked. The non-functional gene can be any gene that provides a detectable readout. In some examples, the non-functional gene is an antibiotic resistance gene (e.g., hygromycin resistance), such that when one of the plurality of index sequences is integrated into the landing pad, the cell expresses the antibiotic resistance gene and cells with a correct integration can be identified or selected based on antibiotic resistance. In other examples, the non-functional gene is a reporter gene, such as a fluorescent protein (e.g., a green fluorescent protein, a red fluorescent protein, or a cyan fluorescent protein, including but not limited to mScarlet or GFPnovo2), such that when one of the plurality of index sequences is integrated into the landing pad, the cell expresses the reporter protein and cells with a correct integration can be identified or selected based on detection of fluorescence. Additional reporters can include LacZ or CAT. In other examples, one portion of the non-functional gene may include a regulatory element (such as a promoter) and the other portion of the non-functional gene may be a coding sequence or portion thereof. Other examples are described in the particular embodiments below.

The plurality of index sequences can be any nucleic acid sequence of interest. In some embodiments, the index sequences are from about 1-15,000 nucleotides in length (e.g., about 1-50 nucleotides, about 10-100 nucleotides, about 25-250 nucleotides, about 50-500 nucleotides, about 200-1000 nucleotides, about 500-2500 nucleotides, about 1000-5000 nucleotides, about 2500-10,000 nucleotides, or about 5000-15,000 nucleotides long). In other examples, the index sequences are greater than 10,000 nucleotides, such as greater than 15,000 nucleotides, greater than 20,000 nucleotides, greater than 25,000 nucleotides, greater than 50,000 nucleotides, greater than 75,000 nucleotides, or greater than 100,000 nucleotides. In some examples, the index sequences are gene coding sequences or portions and/or fragments thereof (such as a gene library), non-coding sequences, promoter elements or portions and/or fragments thereof, amplicon products, randomized genomic sequences, or barcodes. The synthetic landing pads may include gene regulatory elements or portions and/or fragments thereof, a reporter sequence (such as a fluorescent protein or antibiotic resistance gene), or portions of a gene coding sequence. Specific examples of index sequences and synthetic landing pads are discussed in further detail below.

In some embodiments, site-specific integration of an index sequence is accomplished by utilizing a site-specific nuclease (SSN) that recognizing and binding to particular nucleotide sequences, for example, in the genome of a host organism. A DNA sequence that is recognized by the SSN may be referred to as a SSN recognition site. Polypeptide domains that are capable of recognizing and binding to DNA in a site-specific manner generally fold correctly and function independently to bind DNA in a site-specific manner, even when expressed in a polypeptide other than the protein from which the domain was originally isolated. Similarly, SSN recognition sites for recognition and binding by DNA-binding polypeptides are generally able to be recognized and bound by such polypeptides, even when present in large DNA structures (e.g., a chromosome), particularly when the site where the target sequence is located is one known to be accessible to soluble cellular proteins (e.g., a gene).

While DNA-binding polypeptides identified from proteins that exist in nature typically bind to a discrete nucleotide sequence or motif (e.g., a consensus recognition sequence), methods exist and are known in the art for modifying many such DNA-binding polypeptides to recognize a different site. DNA-binding polypeptides include, for example and without limitation: zinc finger DNA-binding domains, leucine zippers, UPA DNA-binding domains, GAL4, TAL, LexA, RNA-guided CRISPR-Cas9, Tet repressors, LacR, and steroid hormone receptors.

In some embodiments, methods provided herein utilize a SSN that includes a DNA-binding polypeptide to recognize and bind a recognition site for the SSN, create a double-strand break targeted to a synthetic landing pad, resulting in integration of an index sequence into the synthetic landing pad by homology-directed repair (HDR). In particular embodiments, the SSN comprises a DNA-binding polypeptide selected from the group consisting of a zinc finger, TAL, and RNA-guided CRISPR/Cas-derived DNA-binding polypeptide. In particular examples, the SSN is a CRISPR endonuclease, such as Cas9, xCas9, SpRY Cas9, or Cas12a. In other examples, the endonuclease is a Zinc finger nuclease (ZFN) or a TAL Effector nuclease (TALEN). In still further examples, a transposon-based method such as mos1-mediated single copy insertion (mosSCI,) or Tol2 is used, or a very rare cutting endonuclease is used, for which a cutting site could be engineered into the landing pad (e.g., srfI in *C. elegans*). The double strand break is then repaired with one of the plurality of index sequences by homology directed recombination. In some examples, the synthetic landing pad and each of the plurality of index sequences further comprise flanking homology arms which are the same (e.g., the 5' ("left") homology arm in the landing pad and the index sequences are the same and the 3' ("right") homology arm in the landing pad and the index sequence are the same). In particular examples, a homology arm is about 100-1,000 nucleotides in length (e.g., about 150-750 nucleotides, about 150-600 nucleotides, about 150-500 nucleotides, about 250-600 nucleotides, or about 500 nucleotides long).

In specific examples, the methods utilize Cas9, and the synthetic landing pad includes a Cas9 guide RNA and flanking homology arms and each of the plurality of index sequences further comprise the same flanking homology arms. In some examples, the cell is transgenic for Cas9, or a recombinant Cas9 protein is introduced into the cell.

The disclosed methods can be performed in a eukaryotic cell (such as a yeast, *Caenorhabditis elegans*, or mammalian cell) or a bacterial cell (such as a *E. coli* cell). In some examples, the methods are carried out in vitro. In other examples, the methods are carried out in vivo, for example in *C. elegans*. Thus, in some examples, an organism is transgenic for the synthetic landing pad and is administered the plurality of index sequences. In one non-limiting example, the plurality of index sequences is administered to the germline of *C. elegans* (see, e.g., FIG. 2).

In some examples, the plurality of index sequences that are introduced into the cell are in an extrachromosomal array of nucleic acids, a plasmid, or an artificial chromosome (such as a bacterial artificial chromosome or a yeast artificial chromosome).

In particular examples, the plurality of index sequences are in an extrachromosomal array. In one example, an extrachromosomal array of nucleic acid molecules is produced in *C. elegans* by injecting a plurality of nucleic acid molecules into the gonad arm of the *C. elegans*, thereby forming the extrachromosomal array of nucleic acids comprising the nucleic acid molecules. In some examples, the extrachromosomal array includes about 1-65,000 index sequences, for example, about 1-1000 about 10-100, about 50-250, about 200-600, about 500-1000, about 750-1500, about 500-3000, about 1000-5000, about 2500-10,000, about 5000-15,000, about 10,000-25,000, about 30,000-50,000, or about 40,000 to 65,000 index sequences. In one non-limiting example, the array includes about 600 index sequences. The size of the extrachromosomal array is in some examples about 1 kb to about 2 Mb, for example, about 1-500 kb, about 100-200 kb, about 250-750 kb, about 500-1000 kb, about 750-1500 kb, or about 1000-2000 kb.

Exemplary Method Embodiments

The disclosed methods can be utilized in a variety of methods for analysis of gene expression, function, and evolution. Exemplary embodiments are provided below. While at least some of the embodiments discussed below refer to CRISPR/Cas9 methods, it should be understood that other CRISPR systems or other methods for integration of index sequences (such as those discussed above) can also be utilized in these methods.

Integration of gene libraries. In this embodiment, the index sequences (e.g., a disclosed array) include gene libraries, which may be native or non-native to the cell or organism utilized. The landing pad includes regulatory elements for genes within the library. Upon recombination, the single genes within the library integrate and are expressed uniformly across independent strains. Thus, large gene libraries can be compared within a single experiment. In some embodiments, the first portion of the sequence in each of the plurality of index sequences is an element from a gene library, and the second portion of the sequence in the synthetic landing pad is a regulatory sequence for the elements from the gene library, wherein each of the plurality of genetically modified cells comprises a single element from the gene library Identification of gene expression patterns. In this embodiment, the index sequences (e.g., a disclosed array) include a library of promoter elements, and the landing pad includes an inactive reporter protein coding sequence. Integration of a single promoter element restores the reporter protein coding sequence, showing the expression pattern of the gene from which the promoter element is taken. If the library contains ~1000 variants, integration of each promoter for a genome of ~20,000 genes would reduce the required labor by ~1000-fold compared to current individual analysis methods.

In some embodiments of the method, the first portion of the sequence in each of the plurality of index sequences is a different promoter element, and the second portion of the sequence in the synthetic landing pad encodes a reporter. In some examples the reporter encodes a fluorescent protein (e.g., a green fluorescent protein, a red fluorescent protein, or a cyan fluorescent protein, including but not limited to mScarlet or GFPnovo2). Additional reporters include LacZ or CAT. In particular examples, each of the plurality of genetically modified cells comprises a single promoter element linked to the reporter sequence and the reporter. The method further includes detecting a signal from the reporter, such as detecting fluorescence if the reporter is a fluorescent protein. The signal from the reporter can provide qualitative and/or quantitative information regarding the expression of the gene from which the promoter element is taken, including but not limited to spatial and/or temporal expression patterns.

Evolution of novel proteins. In this embodiment, the index sequences (e.g., a disclosed array) are formed from amplicon products. Several organisms (e.g. yeast and *C. elegans*) are capable of recombining amplicons in a directed way to result in a functional gene or portion thereof. These variable amplicon products are recombined in the array (e.g., artificial TARDIS chromosome) to produce several combinations. The landing pad includes elements which are not varied, and depend on the protein that is being evolved. Once simultaneously integrated, variants are selected based on an assay phenotype.

In some embodiments of the method, each of the plurality of index sequences comprises a first portion of a reference sequence of interest (e.g., a coding or non-coding sequence) comprising at least one variation from the reference sequence, and the synthetic landing pad comprises a second portion of the reference sequence of interest, wherein each of the plurality of genetically modified cells comprises a reconstituted sequence of interest comprising the at least one variation. In particular examples, the reference sequence is a native form of the sequence of interest. In some examples, the plurality of variants of the sequence of interest is generated by mutagenic PCR.

The method may also further include detecting an assay phenotype resulting from the reconstituted variant sequence and/or selecting a variant of interest based on the assay phenotype. Exemplary assay phenotypes include, but are not limited to membrane transport activity (for example for new molecular ligand activity), neuronal longevity (for example, for a neuropeptide variant), or enzyme activity (for example, temperature sensitivity). An appropriate assay can be selected based on the sequence being evolved.

Down-regulation of genes. In this embodiment, the index sequences (e.g., a disclosed array) include gene promoter fragments or fragments of gene coding sequence. In some embodiments, the array includes promoter fragments, and the landing pad includes an inactive CRISPR guide RNA, which becomes active upon recombination with the promoter sequence and targets an inactive version of Cas9 to the native gene promoter, decreasing or inhibiting gene expression. Thus, in one example, the first portion of the sequence in each of the plurality of index sequences is a different promoter element, and the second portion of the sequence in the synthetic landing pad further includes a CRISPR guide RNA. The cell also includes a catalytically inactive Cas9 (e.g., the cell is transgenic for a Cas9, such as dCas9). Expression of the reconstituted sequence is down-regulated upon activation of Cas9.

In other embodiments, the index sequences (e.g., a disclosed array) includes gene coding sequences and the landing pad includes a mechanism to produce an RNAi response to decrease gene expression. In some examples, the landing pad includes dual and opposite orienting promoter elements to produce an RNAi response, thereby decreasing or inhibiting gene expression. In one example, the first portion of the sequence in each of the plurality of index sequences comprises a different gene coding sequence or portion thereof, and the second portion of the sequence in the synthetic landing pad comprises dual and opposing promoter elements. Expression of the reconstituted sequence is then down-regulated by an RNA interference process. In other examples, the landing pad includes a constant region, which would be transcribed into the mRNA. That constant region is targeted by a constitutive RNAi process, which is seeded by dsRNA generated from another location in the genome or experimentally introduced into the animal/cells, thus down-regulating the reconstituted sequence by RNAi.

In some examples, expression (e.g., amount) of the sequence is detected by observation the amount of a reporter, such as a fluorescent protein. In another example, tissue samples are obtained and the quantity of the protein (e.g., if the protein has a tag, such as a His tag) or mRNA is measured. Down-regulation of expression can be determined by comparison of expression of the sequence compared to a control.

Up-regulation of genes. In this embodiment, the index sequences (e.g., a disclosed array) includes gene promoter fragments and the landing pad includes an inactive CRISPR guide RNA, which becomes active upon recombination with the promoter sequence. This targets an inactive Cas9 coupled to a transcription factor to the native promoter and increases gene expression. Thus, in some examples of the methods, the first portion of the sequence in each of the plurality of index sequences is a different promoter element, and the second portion of the sequence in the synthetic landing pad further comprises a CRISPR guide RNA. The cell further also includes a catalytically inactive Cas9 linked to a transcription activator, wherein expression of the reconstituted sequence is up-regulated upon activation of Cas9.

In some examples, expression of the sequence is detected by observation the amount of a reporter, such as a fluorescent protein. In another example, tissue samples are obtained and the quantity of the protein (e.g., if the protein has a tag, such as a His tag) or mRNA is measured. Up-regulation of expression can be determined by comparison of expression of the sequence compared to a control.

Mutagenesis of genes. In this embodiment, the index sequences (e.g., a disclosed array) include randomized genomic sequences extracted from the organism. The landing pad includes an inactive CRISPR guide RNA, which becomes active upon recombination and targets an active version of Cas9 to the corresponding native sequence. This causes repeated cutting of the locus from the Cas9 until the native site is mutated. This method allows random mutagenesis, while being able to identify the targeted gene without whole genome sequencing. For example, because the location of the landing pad is known, that region can be directly sequenced (e.g., by Sanger sequencing) and the targeted gene can be identified. For example, if a mutant phenotype is observed, the synthetic landing pad is sequenced, and the index sequence will encode a fragment of gene X. Gene X can then be sequenced at its native location and the mutation is identified.

In one example, the first portion of the sequence in each of the plurality of index sequences is a randomized genomic fragment from an organism of interest, and the second portion of the sequence in the synthetic landing pad further comprises a CRISPR guide RNA, and wherein the cell further comprises a Cas9 protein. The reconstituted sequence is modified by activated Cas9 to produce a mutagenized sequence. In particular examples, the mutagenized sequence is identified by sequencing. In another example, the amplicon product from the synthetic landing pad is hybridized to an array (such as a gene array), in order to identify the mutagenized gene.

Analysis of evolution of adaptation. In this embodiment, the index sequences (e.g., a disclosed array) include small, randomized DNA sequences (e.g. barcodes). In some examples, the barcode is about 4-20 nucleotides in length (such as about 4, 5, 6, 7, 8, 9, 10, 11, 12, 13, 14, 15, 16, 17, 18, 19, or 20 nucleotides long). In other examples, the barcode is greater than 20 nucleotides in length, such as greater than 25, greater than 30, greater than 40, or greater than 50 nucleotides long. Once integrated in a synthetic landing pad, the sequences are locked to the genome and can be observed or traced through a lineage, for example, for analyzing evolution.

In some examples, the first portion of the sequence in each of the plurality of index sequences is a unique barcode sequence, and expression of the reconstituted sequence is monitored by detection of the barcode. In particular examples, the method is performed in vivo (e.g., in *C. elegans*) and the lineage of a cell can be traced by detecting the barcode.

Discovery of functional residues. In this embodiment, the index sequences (e.g., a disclosed array) include variants of single gene fragments which have been systematically or randomly varied, to change residues upon translation. The landing pad includes a portion of the gene coding sequences that does not vary, including the gene's regulatory sequences. Once integrated, these variants are expressed and can be analyzed (e.g. by a phenotype assay). Variants with a selected phenotype can be determined by sequencing and correlated with their effects. In one example, the array is an alanine scanning library, which allows variation of each residue.

Figure 5:
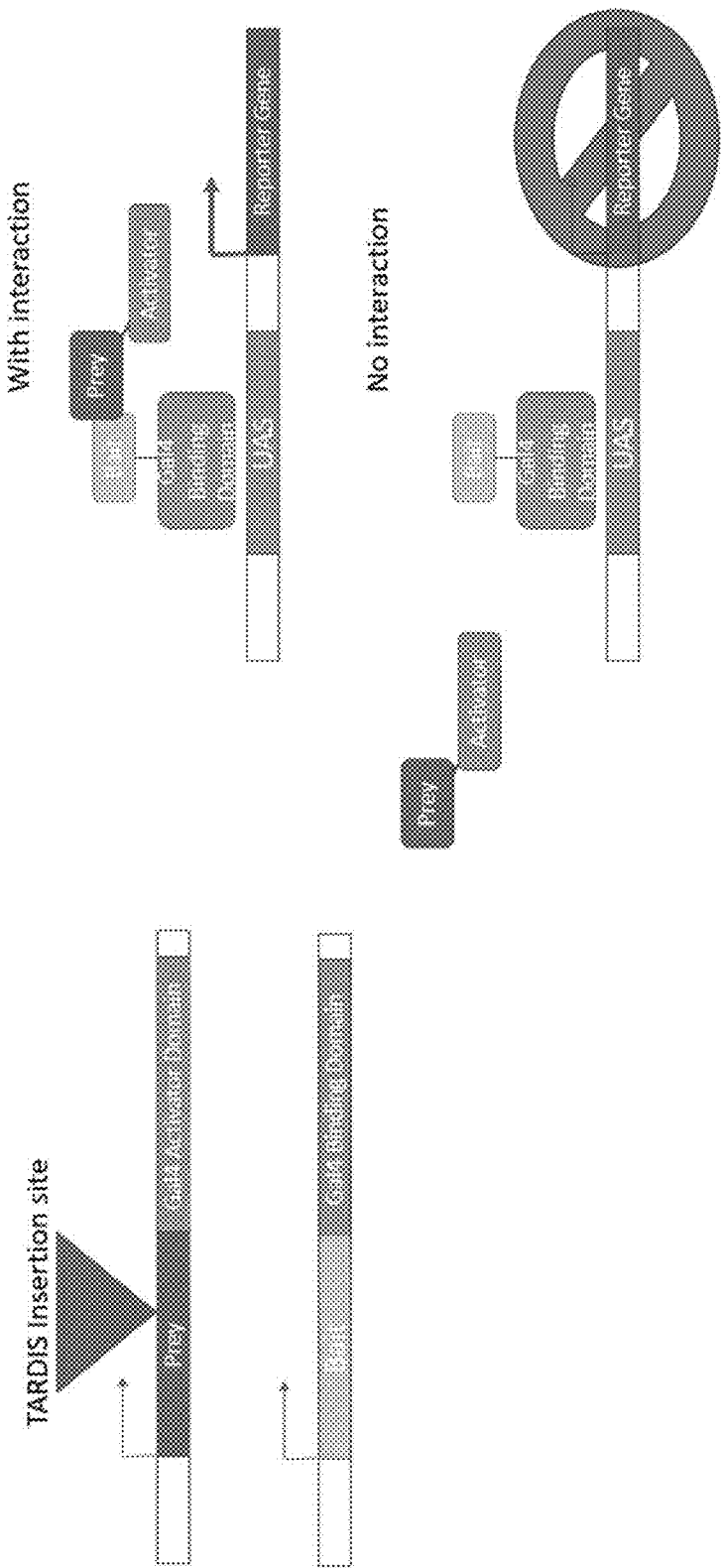
FIG. 5 is a schematic diagram illustrating an embodiment method for detecting protein-protein interactions. For example, the landing pad (e.g., "TARDIS insertion site") includes gene regulatory sequences and the coding sequence for a peptide that can be used as a readout for protein-protein interactions. Upon integration of a protein coding sequence (prey) from the array, the landing pad site produces a hybrid protein that contains both the prey and the peptide used to detect protein-protein interactions. In addition, a second protein sequence is expressed (from the same or a different genomic location) that is hybrid for the test sequence used to test for protein-protein interactions (bait) and a second peptide sequence with functional relevance. If the bait and prey interact, then the two functional peptides are brought into contact and result in a functional readout.

Protein-protein interactions. In this embodiment, the index sequences (e.g., a disclosed array) include potential protein coding sequences (e.g., synthesized or obtained through genomic fragmentation). A schematic of an exemplary embodiment is shown in FIG. 5. For example, the landing pad (e.g., "TARDIS insertion site") includes gene regulatory sequences and the coding sequence for a peptide that can be used as a readout for protein-protein interactions. Upon integration of a protein coding sequence (prey) from the array, the landing pad site produces a hybrid protein that contains both the prey and the peptide used to detect protein-protein interactions. In addition, a second protein sequence is expressed (from the same or a different genomic location) that is hybrid for the test sequence used to test for protein-protein interactions (bait) and a second peptide sequence with functional relevance. If the bait and prey interact, then the two functional peptides are brought into contact and result in a functional readout. In some examples, this assay could reconstitute a functional transcriptional regulator where transcription of a reporter is modulated, for example, reconstitution of a fluorescent reporter so that fluorescence indicates interaction, bringing together two fluorophores whose interaction can be monitored (e.g., by FRET), or reconstitution of a functional phenotype, such as antibiotic resistance. In one non-limiting example, the peptides that provide a functional readout are a Gal4 activator domain and a Gal4 binding domain and the reporter is operably linked to an upstream activator sequence (UAS) for Gal4. If the bait and prey interact, the reporter gene is expressed, providing information about the protein-protein interaction. If the bait and prey do not interact, then the reporter gene is not expressed.

Changing native localization of genes. In this embodiment, the index sequences (e.g., a disclosed array) includes gene promoter fragments and the landing pad includes an inactive CRISPR guide RNA, which becomes active upon recombination with the promoter sequence and targets an inactive version of Cas9 coupled to a tissue-specific transcription factor to the native promoter. This results in altered tissue expression of the gene. Thus in some examples, the first portion of the sequence in each of the plurality of index sequences is a different promoter element, and the second portion of the sequence in the synthetic landing pad further comprises a CRISPR guide RNA, and wherein the cell further comprises a catalytically inactive Cas9 linked to a tissue-specific factor. Tissue expression of the reconstituted sequence is altered upon activation of Cas9. Detecting changed expression of the native gene can be done in several ways, including qPCR to broadly assay changes in mRNA, single cell sequencing to detect cell-specific changes, in situ hybridization, or a phenotypic readout (including, but not limited to longevity). Alternatively, if the native gene has a fluorescent tag or other reporter, the location change of the expression can be determined by detecting the reporter.

EXAMPLES

The following examples are provided to illustrate certain particular features and/or embodiments. These examples should not be construed to limit the disclosure to the particular features or embodiments described.

Example 1

In Situ Donor Assembly and Integration

Two or six PCR fragments with 30 bp overlaps, covering the sqt-1(e1350) gene, were amplified from pDD285 using Q5 polymerase (NEB) in accordance with manufacturer instructions. Homology arms with 30 bp overlaps with the sqt-1(e1350) gene were similarly amplified from pMS81. These homology arms were then complexed with the adjoining sqt-1(e1350) PCR fragment through a second round of PCR.

For in-situ assembly and integration, a mixture consisting of 50 ng/μL pMS79, 5 ng/μL pZCS16 and 40 fmol/μL of each of the appropriate PCR products was microinjected into the gonad of young adult PX696 landing pad (SEQ ID NO: 43) worms. As a control, 10 ng/μL pZCS52 was substituted for the PCR products. Following injection, all worms were maintained at 25° C. for the duration of the experiment. After 24 hours, injected adults were moved to new plates to facilitate counting. F1 individuals were screened for red fluorescence and the roller phenotype at 3-4 days post injection. Hygromycin B was then added to plates at a final concentration of 250 μg/mL. Each day for five days post exposure, plates were scored for hygromycin resistance. Individuals resistant to hygromycin and with the roller phenotype were singled to new plates without hygromycin and screened for Mendelian inheritance of the roller phenotype to indicate an integration event. Lines with promising candidates were singled until they produced homozygous progeny, which were then screened by PCR and Sanger sequencing for correct transgene assembly and integration.

While plasmids offer the advantage of producing large quantities of the repair template, they can be laborious to produce. Standard cloning practices require a source of DNA, a ligation step, bacterial transformation, plasmid purification, and verification. This process can be costly in terms of time and funds while requiring technical expertise and lab equipment. As we sought to reduce the overall time-to-integration, we attempted to bypass the cloning step and utilize the *C. elegans* native homology directed repair to produce a transgene (FIG. 1). To test this approach, we utilized the sqt-1(e1350) mutant as it has a dominant roller phenotype allowing us to easily assay for in situ assembly. Confirmed correct in situ assembled and integrated sqt-1 gene was obtained using both two and six PCR fragments (Table 1). As expected, two parts were easier to correctly assemble and integrate compared to six parts. In some cases, hygromycin resistant individuals were observed without the sqt-1 roller phenotype. We believe these represent incorrect integration events, where at least the 5' hygromycin resistance coding fragment was integrated into the genome. As these cannot represent correct integration and assembly events, we did not pursue or characterize them.

TABLE 1

In situ assembly and integration efficiency

|  | Hygromycin Resistant Broods | | | In situ Assembly | | |
| --- | --- | --- | --- | --- | --- | --- |
|  | Marker positive broods | All roller | Mixed | All wt | Homozygous roller isolated | PCR confirmed integrations | Error free integrations |
| Plasmid | 15 | 3 | 0 | 0 | 3 | 3 | 3 (20.0%) |
| 2pc PCR | 41 | 6 | 3 | 0 | 8 | 6 | 3 (7.3%) |
| 6pc PCR | 51 | 0 | 8 | 5 | 1 | 1 | 0 (0.0%) |

For two-part assemblies, most hygromycin integration events were accompanied by sqt-1 assembly and integration, as indicated by the ability to isolate homozygous roller populations. However, not all of these insertions matched the expected sequence. Two of the 8 insertions could not be amplified by PCR, suggesting large insertions or deletions, while three had point mutations identified during sequencing and three had no detectable errors. In contrast, in the six-part experiment, all resistant plates had non-roller (incorrect) integration events, with a few having roller individuals as well (Table 1). In most cases, a homozygous roller line could not be isolated, suggesting these individuals were the result of correctly assembled genes in arrays paired with incorrect integrations. In one case a homozygous roller line could be isolated, indicating multiple integration events had taken place in that brood. In this case the roller causing integration had a correctly assembled sqt-1(e1350) gene but also contained a second copy of one of the homology arms.

Example 2

Generation of Barcoded *C. elegans* PCR Products for Donor Homology and Injection Mixture Amplicon 1 (barcode amplicon) was prepared by PCR amplification from ultramer ZCS133 with oligos ZCS134 and ZCS135 (Table 2) for ~30 cycles with Q5 polymerase (New England Biolabs). Amplicon 1 (134 bp) was gel extracted.

Amplicon 2 (left homology arm) was PCR amplified off pZCS32 with oligos ZCS273 and ZCS275 (Table 2) for ~30 cycles with Q5 polymerase and gel extracted (500 bp).

Amplicon 3 (right homology arm) was PCR amplified off pZCS32 with oligos ZCS236 and ZCS278 (Table 2) for ~30 cycles and gel extracted (500 bp).

Amplicon complex (compressed barcodes for array formation) was prepared by complexing PCR to fuse Amplicons 1, 2, and 3. All three amplicons were mixed at ~1 ng each, along with oligos ZCS273 and ZCS278 and PCR amplified for ~30 cycles with Q5 polymerase. The final amplicon product was gel extracted.

An injection mixture was prepared by mixing 10 ng/µL pZCS36 (pUC19-hsp-16.41::piOptCas9::tbb-2u), 0.5 ng/µL pZCS38 pUC19-prsp-27::NeoR::unc-54utr;), 15 ng/µL pZCS41 (SEQ ID NO: 36) (perfect homology sgRNA targeting to SLP 32.1PC), with ~45 ng/µL amplicon complex. The injection mix must be above 40 ng/µL, however, a toxic or upper limit has not yet been identified. The injection mixture was frozen at −20° C. until needed.

TABLE 2

PCR product barcode library from ZCS133

| Name | Sequence* | SEQ ID NO: |
| --- | --- | --- |
| Ultramer ZCS133 | CCGACGGATTCTACAAGgtaagtttaaacatatNN NNNNNNNNNNNNNtatttaaattttcagGACCGTT ACGTCTACC | 1 |
| ZCS134 | GATACGTCCTCCGTGTCAACTCCTGCGCCGACGGA TTCTACAAGgtaagtttaaacata | 2 |
| ZCS135 | ATTGGGAGGGCGGCGGAGGCGAAGTGACGGTAGAC GTAACGGTCctgaaaatttaaata | 3 |
| ZCS273 | CGCGTCTCTTCCGTGCG | 4 |
| ZCS275 | CGTCGGCGCAGGAGTT | 5 |
| ZCS276 | GTCTACCGTCACTTCGCCTCC | 6 |
| ZCS278 | GACCTCGTATTGGGAGTCTCCG | 7 |

*Uppercase signifies coding sequence and lowercase signifies non-coding sequence.

Injection of *C. elegans*

Day 0: Single L4 staged strain 32.1PC (Synthetic Landing Pad strain for Barcode Integration) were placed into a small NGM plate with food at 15c ° C. overnight.

Day 1: Injection mixture was spun in microcentrifuge at maximum speed for 10 minutes. About 30 young adult worms were injected and placed on individual plates at 20° C.

Day 4: Each injected worm plate was top spread with 1.56 mg/mL G418. If the plate was approaching starvation, 50-100 µL concentrated HB151 or OP50 was added. Water was added if necessary, to ensure enough liquid volume to cover the top of the plate. Plates were dried briefly on the benchtop, then placed back at 20° C.

Day 11: Plates were screened for those worms that survived G418 selection, indicating presence of TARDIS array. Lines were maintained on G418 to retain TARDIS array and each line was frozen down.

Day 11+: Several large plates were grown with G418 and concentrated food until the population was saturated and gravid. A bleaching event was performed to isolate the eggs. Briefly, worms and bacteria were pelleted in a 15 mL falcon tube. After pouring off supernatant, 5 mL M9 medium, 600 µL bleach, and 300 µL NaOH were added, and vortexed to mix briefly. Worms were allowed to dissolve in bleach for approximately 5 minutes, checking every minute afterwards for completely dissolved worms and free-floating eggs.

Once free-floating eggs were isolated, they were buffer extracted with M9 to wash away the bleach 3× times by pelleting the eggs, pouring off the supernatant, and repeating with M9. On the last wash, the falcon tube was filled with M9 and G418 added at 1.56 mg/mL. The eggs were allowed to hatch in M9 overnight in a nutator at 20° C. Only worms with the TARDIS array will hatch due to the Neomycin selection.

L1 worms were pelleted and washed with M9 2×. L1 worms were plated to desired density on a large plate without G418 and allowed to grow at 20° C. overnight. The L2/L3 population was heat shocked at 35.5° C. for 1 hour, inducing the heatshock Cas9, targeting the SLP and creating a break.

The worms were allowed to reach adulthood and start laying eggs. Then 250 μg/mL Hygromycin B was added to select for only barcode integrated worms. If the barcode integrated into the chromosome, the worms have a restored hygromycin resistance gene. If not, the worms will die.

Depending on how many worms were heat shocked and how many barcodes were in the TARDIS array, the population will be highly diverse. Around 1 in 10 worms heat shocked exhibited an integration event, and the TARDIS arrays have around 600 barcodes per independent array.

Example 3

Index Directed Genomic Screening

While forward genetic screens are invaluable in biological study, they suffer from three major weaknesses: (1) Gain-of-function mutations are exceedingly difficult to obtain; (2) Mutations in many genes relevant to the phenotype of interest are difficult or impossible to obtain due to epistasis; and (3) Tissue- or developmental stage-specific mutations are either exceedingly difficult or impossible to recover. These issues are addressed by the Index Directed Genomic Screening (IDGS) system that enables (1) controllable, "directional" mutations, (2) ~1,000 fold increase in transformation throughput, (3) recovery of mutations for target genes/phenotypes unobtainable by traditional mutagenesis (e.g. phenotypes that exhibit post-reproductively or genes that cannot be targeted due to epistasis), and (4) the reduction of months of mapping work to a simple Sanger sequencing reaction. The IDGS system enables the creation transgenic animals with unique index insertions targeting random genes specifically desired spatiotemporally controlled genetic changes. The IDGS technology represents a transformational change in genetic screening across all biological disciplines.

A Genomic Index Integration System

Genetically engineered genomic "synthetic landing pads" (SLPs) are used that can carry a portion of a selectable sequence (e.g., a hygromycin antibiotic resistance cassette (HygR)), sequences for facilitating integration of new DNA sequences (e.g., a synthetic Cas9 guide target, and homology arms for homology directed repair (HDR) (FIG. 3A)). Integration of index sequences reconstitute the selectable sequence (e.g., reconstitution of the functional HygR) by the native HDR machinery. Appropriate integrations are selected using the appropriate selection for the landing pad used. The throughput of integration can be increased using the "data compression" of the TARDIS system, in which injection of massively diverse index mixes results in neomycin selectable intermediate arrays that carry >1,000 indexes each (FIG. 3B). One array-carrying individual can give rise to large array carrying populations in which integration is induced (FIG. 3A). Once induced, only single indices are integrated, and subsequently expressed across the population, allowing the full library of indices to be expressed in single lineages. This approach holds many benefits over traditional mutagenesis in C. elegans. For example, inserted indexes can be cloned by simply sequencing a PCR product, a >1000-fold decrease in labor versus traditional mutation mapping. This allows identification of indexes in post-reproductive, developmental arrest, or sterility situations. While the synthetic landing pads make identification of the genetic alteration fast and cheap, the synthetic landing pads themselves can be engineered to couple the index with genetic regulatory systems for screens (see below).

Directional Regulatory Index Synthetic Landing Pads

Figure 4:
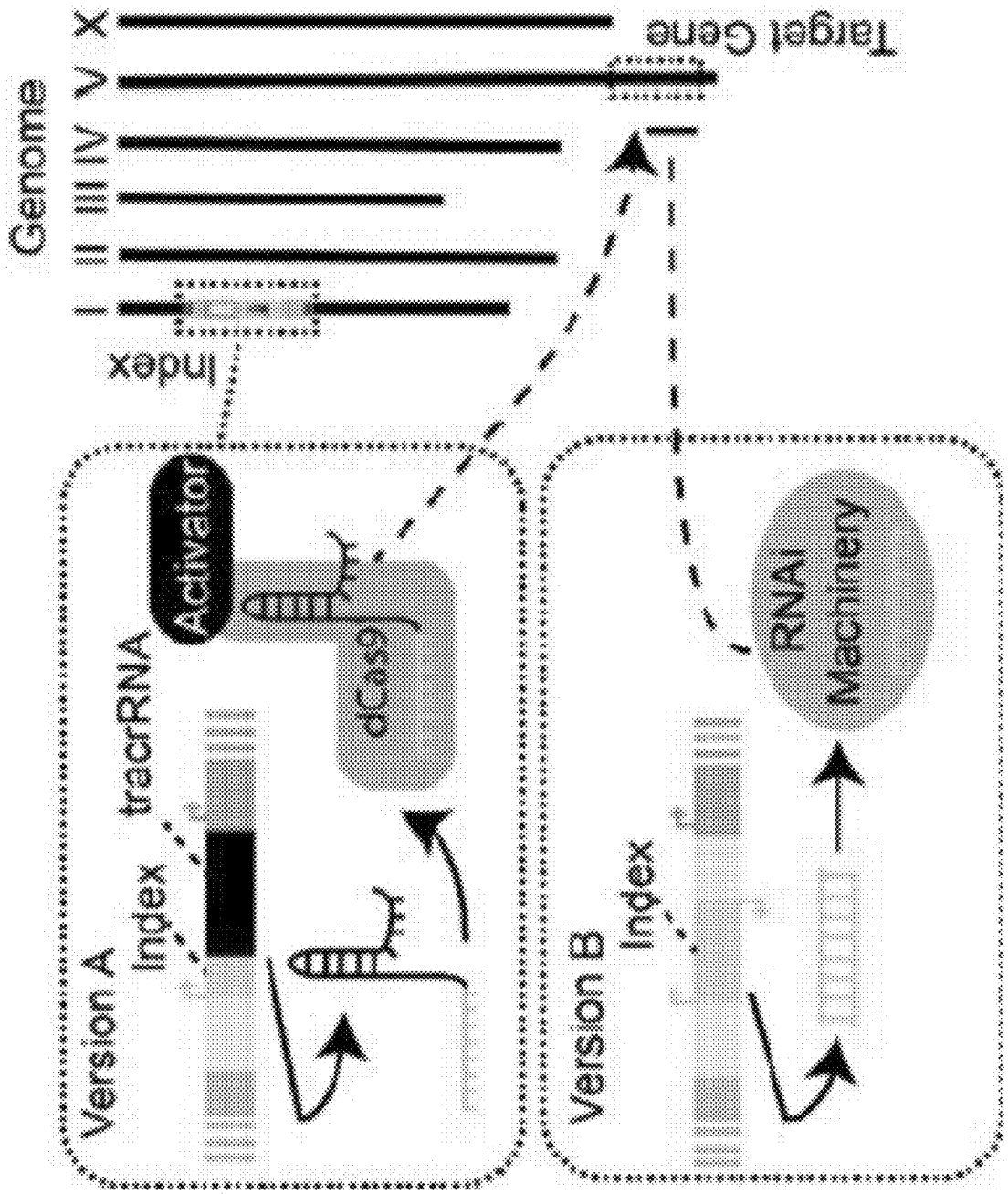
FIG. 4 illustrates index directed "directional" genomic screening. Two versions of the synthetic landing pads enable controlled, directional regulation of distant genomic loci. In Version A (top), after insertion, the index becomes the targeting sequence in a CRISPR gRNA-tracrRNA hybrid RNA molecule that is tethered to a transcriptional activator allowing positive regulation of genes with the appropriate indexed sequence. In Version B (bottom), the index is embedded in a bidirectionally transcribed location. The resultant dsRNA then feeds into the RNAi pathway to negatively regulate distant genes that feature the indexed sequence.

To perform genetic screens using index sequences the index sequence is coupled with regulatory machinery that will ultimately alter gene function in a sequence-specific fashion. Two example synthetic landing pad configurations for genetic screens are provided here, one specific for gene up-regulation and one for down-regulation (FIG. 4). The up-regulation synthetic landing pad embeds the index integration site into a CRISPR guide RNA expression cassette such that the index becomes the target sequence of the gRNA. This enables the index to guide Cas9 proteins to distant genomic loci in a sequence specific fashion. When coupled with a DNAse-deficient Cas9 (dCas9) variant that is tethered to a transcriptional activator for upregulation of genes, the indexed-gRNAs enable a high-throughput, forward genetic screen specific for upregulation of genes in a model animal. The second example synthetic landing pad is a dual-promoter system in which the index is transcribed in bi-directionally. The resultant dsRNA triggers an RNAi response for genes that contain the index sequence. In a genetic background without systemic RNAi, the loss of gene function is restricted to the tissues in which the index promoters are expressed.

For both synthetic landing pad versions, usage of spatially and temporally restricted promoters gives a unique, high-throughput forward genetic screening system with spatiotemporal control for altered gene function. This enables screening for mutational effects with tissue and developmental restriction not previously available. While two index mediated screening approaches are described in this Example, there are many other ways to use this highly adaptable system. Additional non-limiting exemplary applications are provided in Table 3.

TABLE 3

Exemplary applications of IDGS technology

| Index Synthetic Landing Pad | Effector | Uses |
|---|---|---|
| | | Genetic Screening |
| CRISPR Guide RNA | Cas9 | Targeted somatic mutation with temporal-spatial control from Cas9 and guide RNA promoters |
| | dCas9 with tethered positive transcriptional regulator | Targeted up-regulation of native genes with temporal-spatial control from dCas9 and guide RNA promoters |
| | dCas9 with tethered negative transcriptional regulator | Targeted down-regulation of native genes with temporal-spatial control from dCas9 and guide RNA promoters |
| Bi-directional promoter | Native RNAi machinery | Bidirectional transcription of index to create dsRNA for RNAi. In a sid-1(-) background the promoters used would give spatiotemporal control of gene inactivation for screening |

TABLE 3-continued

Exemplary applications of IDGS technology

| Index Synthetic Landing Pad | Effector | Uses |
|---|---|---|
| Expressed mRNA | Transitive RNAi | Transcription of index as part of an mRNA which is targeting for RNAi. Transitive RNAi would induce silencing of genes with the index sequence Screening Protein Function |
| Protein fusion used as prey in two-hybrid system | Another expressed protein which acts as the bait, which induces a phenotype when it physically interacts with the prey protein. | Protein-protein interactions in an animal where post-translational regulation, intercellular signaling, and tissue differences are available. Use of a synthetic landing pad attaching the index sequence to a split transcription factor enables organism level two-hybrid assays |

Example 4

Adaptive Barcoded Lineage Tracking

TARDIS was originally developed for adaptive barcoded lineage tracking. Lineage tracking aims to identify and quantify the selective advantage of unique lineages during experimental evolution. This was experimentally measured by sequencing barcodes. Barcodes were integrated in the genome of independent lineages, marking each with a unique sequence. Lineage tracking requires minimally tens of thousands of individual lineages competing with one another. For microbial systems, this is achieved with library transgenesis by transformation. For animal systems, the TARDIS system was developed.

Methods

Strains and Growth Conditions. Bristol N2-PD1073 and the derived strains PX740, PX742 and PX743 were maintained using standard *C. elegans* protocols (Stiernagle, T. (2006). Maintenance of *C. elegans*. WormBook, 1999, 1-11). In brief, strains were maintained on NGM-agar plates seeded with OP50 or HB101 *Escherichia coli* at 15° C. unless otherwise noted.

Molecular Biology. All plasmids were cloned by Gibson Ligation following standard HiFi protocol from New England Bio Labs. pUC19 vector was PCR amplified with ZCS149 (SEQ ID NO: 8) and ZCS150 (SEQ ID NO: 9) to open the MSC for all cloning. To generate heatshock inducible Cas9, hsp16.41 was derived from pMA122. The germline licensed piRNA depleted Cas9 and tbb-2 3' UTR (SEQ ID NO: 33) was derived from pCFJ150-Cas9(dpiRNA). The final construct hsp16.41p::Cas9dpiRNA::tbb-2 '3UTR was Gibson cloned into pUC19 to create pZCS36. To generate an empty gRNA vector, the U6 promoter (SEQ ID NO: 34) and gRNA scaffold sequence (SEQ ID NO: 35) was amplified from pDD162. The final construct U6p::(empty)gRNA::U6 Terminator was Gibson cloned into pUC19 to create pZCS11.

To generate the synthetic landing pad targeting plasmid pZCS41 (SEQ ID NO: 36), the synthetic target sequence GCGAAGTGACGGTAGACCGT (SEQ ID NO: 37) was added with primer overlaps and Gibson cloned into vector pZCS11. To generate the synthetic landing pad sequence pZCS32, the 5605 SEC homology vector pMS4 was PCR amplified with ZCS139 (SEQ ID NO: 10) and ZCS138 (SEQ ID NO: 11) to remove the let-858 terminator to create pZCS30. pZCS30 served as an intermediate to pZCS32. The broken hygromycin landing pad was constructed by removing the intron within the hygromycin resistance gene in pCFJ1663. The perfect homology targeting site was created by fusing exon 1 and exon 2, while also removing three codons from both exons. The vector backbone was amplified with ZCS140 (SEQ ID NO: 12) and ZCS145 (SEQ ID NO: 13) from pZCS30. The prsp-0p::HYGRΔ5' was amplified with ZCS141 (SEQ ID NO: 14) and ZCS154 (SEQ ID NO: 15) from pCFJ1663. The HYGRΔ3'::unc-54 3' UTR (SEQ ID NO: 39) was amplified with ZCS155 (SEQ ID NO: 16) and ZCS144 (SEQ ID NO: 17). The final plasmid was confirmed by Sanger Sequencing. The Neomycin Resistance co-marker pZCS38 was cloned by PCR amplifying prsp-27::NeoR::unc-54 3' UTR from pCFJ910 with primers ZCS164 (SEQ ID NO: 18) and ZCS165 (SEQ ID NO: 19), and was cloned into pUC19. To generate an additional fluorescent co-injection marker, eft-3p (SEQ ID NO: 40) and tbb-2 3' UTR (SEQ ID NO: 33) (amplified from pDD162) and wrmScarlet (SEQ ID NO: 41) (amplified from pSEM89; a gift from Thomas Boulin) were cloned into a pUC19 backbone to give pZCS16.

Base Landing Pad Strain Generation. Strain PX740, which serves as the base TARDIS strains for Array Quantification and Lineage Tracking, was made by injecting pZCS32 (10 ng/μL) (landing pad of SEQ ID NO: 51) along with pMS8 (50 ng/μL). pMS8 is a Cas9, guide RNA vector for targeting Chr. II. Screening for integrations was performed following Dickenson et. al. (2015) Genet. 200(4): 1035-49. A single post-Cre candidate was isolated and designated PX740.

For a separate application, independent of lineage tracking, TARDIS was applied to build a library of promoters to identify the expression pattern of thousands of genes. Three separate strains, GT300, GT331, and GT332, all three have split hygromycin selection landing pads similar to PX740. However, instead of being split within an intron, half of the coding sequence is integrated into the genome. On the opposite side of the split Hygromycin resistance gene is a partial coding sequence for mScarlet. The donor plasmid is constructed with a promoter, lacking partial mScarlet coding sequence, and the hygromycin resistance promoter, also lacking coding sequence. This arrangement enables easy identification of correctly inserted sequence units from the library because only correct integrants will exhibit hygromycin resistance and an observable fluorescent protein.

There are minor differences between the three strains: GT300 contains a co-marker, which is removed upon integration. GT300 is also an unc-119 mutant, causing a paralysis phenotype that is rescued with array-expression of cbr-unc-119. GT331 and GT332 are different in that one of these strains has a pest tag on mScarlet to degrade mScarlet quicker, preventing the buildup of the protein and possibly provide a finer-scale resolution of when the expression is occurring.

TARDIS Libraries for Lineage Tracking. The first TARDIS library constructed and utilized was the "500 bp homology library." The 500 bp homology library was constructed by PCR amplifying ZCS133 (SEQ ID NO: 1) with ZCS134 (SEQ ID NO: 2) and ZCS135. ZCS133 contains a set of 15 randomized sequences (NNN's) directly in the middle. The amplicon product served as a base for further PCRs. The Left Homology Arm (SEQ ID NO: 48) was amplified from pZCS32 with primers ZCS273 and ZCS275 to produce a 501 bp product. The Right Homology Arm (SEQ ID NO: 47) was amplified from pZCS32 with primers ZCS276 and ZCS278 to produce a 501 bp product. The final library was generated by complexing PCR with the initial product and the two homology arms in a single PCR reaction with primers ZCS273 and ZCS278 to produce a 1068 bp product (SEQ ID NO: 46).

This library was gel extracted to remove any templates and incorrect amplicon products. The library product (SEQ ID NO: 46) was injected along with pZCS36, pZCS41, ZCS38, and pZCS16 to create PX742.

The second TARDIS library constructed and utilized was the "150 bp homology library." The primary focus of this library was to increase the number of possible donors present in the array (SEQ ID NO: 52). This was achieved by focusing on the quantity of DNA, and the PCR cycle number. Two separate Q5 PCR reactions were performed with 2.5 µL 0.5 µM ZCS357 (SEQ ID NO: 20), 1.25 µL 10 µM ZCS134, 1.25 µL 10 µM ZCS135, 20 µL water, and 25 µL 2× Q5 Master Mix™. Four cycles of PCR were performed with 45 seconds of extension time at 72° C. annealing to produce the barcode base library. The product was column purified to retain as much product as possible. The 150 bp Right Homology Arm (SEQ ID NO: 50) was amplified with ZCS276 and ZCS286 (SEQ ID NO: 21) from pZCS32, the 150 bp Left Homology Arm (SEQ ID NO: 49) was amplified with ZCS285 (SEQ ID NO: 22) and ZCS275 from pZCS32. Both homology arm products were gel extracted. Four secondary complexing PCRs were performed with 1 barcode donor fragment:10 left homology arm:10 right homology arms, for 15 cycles with ZCS285 (SEQ ID NO: 22) and ZCS286 (SEQ ID NO: 21). The final library was gel extracted to avoid incomplete and template products. The final library was injected at 61.75 ng/µL with pZCS36 at 20 ng/µL, pZCS41 at 15 ng/µL, pZCS38 at 0.25 ng/µL, and pZCS16 at 3 ng/µL for a total concentration of 100 ng/µL to create PX743.

TARDIS Single Promoter. Injections into GT300 were done with 25 ng/µL pMS84 (gRNA targeting GT300 synthetic site (SEQ ID NO: 38)). 7 ng/µL heatshock Cas9 (dpiRNA) PCR product (analogous to pZCS36), 10 ng/µL pNU1495 (cbr-unc-119 rescue cassette; analogous to neomycin resistance in the lineage tracking TARDIS libraries), 10 ng/µL pDSP18 (daf-7 promoter with split mScarlet and split Hygromycin resistance). Candidate library strains were selected by rescue of the paralysis phenotype.

Multiple Promoter Libraries. For GT331 and GT332, the same injection mix was used: pMS84 at 15 ng/µL, pZCS36 at 20 ng/µL, pZCS38 at 0.5 ng/µL, pNU681 (an eft-3p::GFP co-marker for array identification) at 2 ng/µL. The promoter library was injected with the following plasmids and their corresponding promoters at 0.45 fmol/µL to facilitate approximately equal composition in the array library: pEA1 (ceh-20), pEA2 (ceh-23), pEA3 (ceh-40), pEA4 (egl-46), pEA5 (hlh-16), pEA6 (nhr-67), pEA9 (ceh-43), pEA10 (mdl-1), pEA11 (egl-43), pEA12 (aha-1), pEA13 (ceh-10), pEA14 (ahr-1), pEA15 (lin-11), and pDSP18 (daf-7).

Several TARDIS array lines were generated from the injections. Two were selected for testing, one from GT331 and one from GT332.

Dual Integrations. One possible benefit of the TARDIS system is the integration of multiple sequences into different sites. To address this possibility, a single strain was generated, GT344, with two unique landing pads. One landing site is similar to GT332, with split Hygromycin B selection and split mScarlet. The second landing pad is engineered with unc-119 split selection, which is similar in protocol to GT300. GT344 was injected with 50 ng/µL pMS79 (Cas9 targeted plasmid with guide RNA for both landing pads (SEQ ID NO: 42)), 10 ng/µL pDSP57 (SEQ ID NO: 44) (split mScarlet donor homology) and 10 ng/µL pDSP58 (SEQ ID NO: 45) (split unc-119 donor homology). After nine days, Hygromycin B was top-spread at a final concentration of 250 µg/mL. Survivors were screened for rescue of unc-119 indicating dual integrations.

TARDIS Integration Protocol for Barcoded Lineage Tracking. TARDIS array-bearing strains are grown at 15° C. to reduce expression of heatshock Cas9. Strains were grown with G418 at 1.56 mg/mL, which provides selection to maintain the array, unless otherwise specified. Large plates were grown until a sizable population of array bearing strains were gravid. Large gravid populations were bleached to isolate eggs following standard protocols. Synchronized L1 individuals were hatched overnight in M9 solution with G418 at 1.56 mg/mL. This ensures all progeny that hatch bear the TARDIS array library. Worms were centrifuged into a pellet and the supernatant was discarded. Worms were washed 2× with M9 to remove remaining G418. L1s were then plated at desired densities and allowed to grow at 15° C. overnight. The next day, L2 worms were heatshocked at 35.5° C. for 2 hours. Worms were then placed at a desired rearing temperature. Once the population reached Day One Adults, Hygromycin B was added at 250 µg/mL to select for barcode integration.

TARDIS Integration for Promoter Libraries. For the single promoter GT300 based library, stable array lines were isolated to large NGM plates and allowed to lay progeny for 4 days at 15° C. Plates were heatshocked at 34° C. for 1 hour. Plates were then incubated at 25° C. After 2 days, Hygromycin B was added at a final concentration of 250 µg/mL.

For mixed promoter libraries injected into GT331 and GT332, an identical integration protocol used for Lineage Tracking was used.

Array Quantification. Individual array line PX742 was lysed and amplified with ZCS287 (SEQ ID NO: 23) and ZCS288 (SEQ ID NO: 24), and sent for Illumina sequencing. Reads were acquired and quality filtered using custom Python code for only reads with quality scores of 30 or higher for the barcode region and barcodes having greater than 10 reads.

Individual array line PX743 was lysed and amplified with New England BioLabs (NEB) Next Ultra II™ kit Universal Primer and Index Primer 2 with 30 cycles. Reads were acquired and quality filtered using custom Python code for only reads with quality scores of 30 or higher for the barcode region and barcodes having greater than 10 reads.

Integration Efficiency. PX742: PX742 was grown, synchronized, and heatshocked, following the protocol above. After heatshock, 10 L3 individual were isolated to 20 plates. Once they reached Day One adulthood, Hygromycin B was top spread at 250 µg/mL. Plates were allowed to grow for several days before screening for survivors.

GT300: To address the efficiency of the GT300 landing pad, 60 individual array-bearing individuals were singled and allowed to lay progeny for four days at 15° C. Plates were heatshocked at 3° C. for 1 hour, and then incubated at 25° C. Two days later, a final concentration 250 µg/mL Hygromycin B was top spread.

To further address the developmental stage in which integration was occurring, several individuals were heatshocked at the L2, L3, L4, and young adult stages.

GT331 & GT332: These libraries were tested for integration efficiency, following the integration protocol listed below. To establish the efficiency of integration, population of 50 individuals/plate, 100 individuals/plate, 200 individuals/plate, and 1,000 worms/plate were synchronized. This was repeated with two separate TARDIS library arrays, one with the GT331 background and the other with GT332. After Hygromycin exposure, plates were screened for survival.

Integration Bias Checking Methods. PX742 counts and relative frequencies were compared to a population of individual worms after TARDIS-based integration. A large integrated population of synchronized L1 worms was heatshocked. The population was allowed to recover for one generation before being lysed and amplified. Two sets of amplification had to be performed to avoid the possibility of amplifying the array. First, four rounds of PCR were performed with ZCS305 (SEQ ID NO: 26) and ZCS304 (SEQ ID NO: 25). ZCS304 introduced a new specific primer binding site for the second round of amplification. The PCR product was column purified and the full product was amplified with ZCS306 (SEQ ID NO: 27) and ZCS307 (SEQ ID NO: 28). This final product was sent for Illumina sequencing. Identical Python code and criteria for array quantification was used to filter reads. Counts were then normalized to the total counts for filtered sequencing runs for both the PX742 array and for the integration population. Barcodes which did not integrate from the array were excluded from the analysis.

Lineage Trajectory Methods. A single parental lineage population was grown to starvation on a large 150 mm plate seeded with concentrated HB101. The parental population was split into 3 separate replicates. Each replicate was also grown on large 150 mm plates seeded with concentrated HB101 and allowed to grow until starvation (~2 generations). At starvation, half of the population was transferred, and half was lysed, for barcode amplification. A total of three transfers and three time points were checked. This approximates to six generations. Barcode amplification followed the protocol set forth above. Data was also analyzed following the same criteria. Normalized data was plotted as both lineage trajectories and as histograms.

PCR jackpotting has the potential to significantly increase the lineage measurement error. To address this, two separate transfers in replicates one and two were chosen to be PCR amplified twice following identical protocols and analysis.

Results

Figure 8:
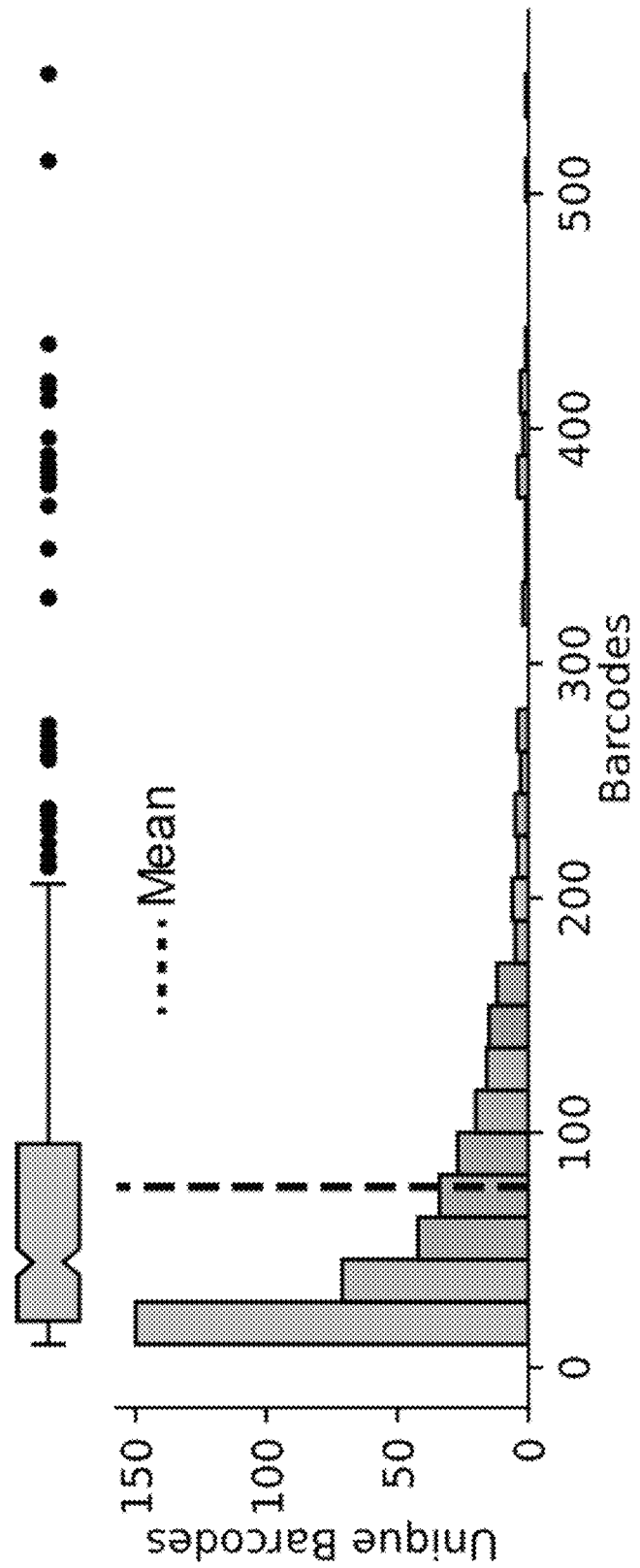
FIG. 8 is a histogram showing the distributions of reads/counts from PX742 sequencing. The X axis is the number of counts a unique index sequence had, and the Y-axis is the number of unique index sequences with that count.

Array Quantification. Approximately 33,137 reads were acquired for PX742 (FIG. 8). After quality filtering, 431 unique sequences were identified from the array line. As expected, barcodes were not injected in perfect equal molar quantities due to their PCR-based construction, and PCR amplification to generate the sequence libraries introduced additional bias. There were many barcodes with fewer reads than expected, with a long tail indicating the result of PCR jackpotting.

For PX743, 771,115 reads were obtained after quality filtering. Because the protocol was modified to reduce the donor homology size, and lower initial amplification cycles for the donor library, more barcodes were expected to be present in the array. 2,965 unique donor sequences were present. Lower cycles and reduced donor homology length increases the total number of barcodes that can be present in an array.

Integration Efficiency

Lineage Tracking-based Libraries. PX742 is the 500 bp large donor homology (SEQ ID NO: 46) TARDIS line, with a considerably small insert. Of the 20 plates, 17 had surviving resistant progeny, indicating a proper integration event. Five plates were randomly selected for Sanger Sequence to confirm the integration. Of the five, two showed two separate integration events, indicating that more than one worm from the ten on the plates had an integration event. Therefore, the integration efficiency was approximately one in ten heatshocked individuals integrated a barcode.

Promoter-based Libraries. GT300-based integrations: For GT300, eight days after dosing with hygromycin all five plates had live worms. Three individuals from each plate were selected for confirmation by PCR (MS376 (SEQ ID NO: 29)/MS248 (SEQ ID NO: 30)/ZCS84 (SEQ ID NO: 31) or MS376/MS121 (SEQ ID NO: 32). Two plates had correct insertions by PCR, two plates had incorrect insertions by PCR, and one plates was inconclusive. The incorrect insertions were attributed to co-marker integration into the landing pad, and this was removed for future builds (GT331 and GT332).

To address the integration efficiency, 60 individuals were screened for integrated progeny. Of the 60, 25 of 59 plates had Hygromycin B resistant progeny. One plate had very few live worms, so it was excluded from analysis. Candidates were not genotyped for proper vs improper integrations.

60 L4 array-bearing individuals were heatshocked and screened for hygromycin survival. Two of the 60 plates produced resistant progeny.

There was a difference in the developmental stage and the number of integrations; younger stages and young adults seemed to work better compared to L3/L4 staged individuals (Table 4).

TABLE 4

Developmental stages and integration efficiencies.

| Developmental Stage | Individuals | Integrations | Percentage |
|---|---|---|---|
| L2 | 20 | 6 | 30% |
| L3/L4 | 19 | 2 | 10.5% |
| L4 | 60 | 2 | 3.3% |
| Young Adult | 19 | 6 | 31.5% |

GT331 and GT332-based integrations: There was a noticeable difference in the integration efficiency of the two strains (Table 5).

TABLE 5

Integration efficiencies for GT331 and GT332.

| Survivors | GT331 (surviving plates/total plates) | GT332 (surviving plates/total plates) |
|---|---|---|
| 50 worms/plate | 1/5 | 0/5 |
| 100 worms/plate | 5/5 | 1/5 |
| 200 worms/plate | 4/5 | 2/4 |
| 1,000 worms/plate | 5/5 | 2/4 |

A clear bias was seen in the integration for GT332 compared to GT331. There are several variables involved, such as the time in which worms' eggs are exposed to bleach during the synchronization process, the total number of worms present in the synchronization, the stability of the array and copy number per cell, and variations in the exact composition from the same injection mixture.

Several promoters were isolated from the library. In some cases, multiple were isolated and noted within ( ): ceh-10(3), ceh-40(5), hlh-16(7), ahr-1(2), aha-1(2), mdl-1(2).

Dual Promoter integrations: One benefit of the TARDIS system is integration into multiple landing sites within a single strain. The strain GT334 was created to have two separate selectable landing pads with different fluorescent reporters. A correct integration was isolated from this injection.

Figure 9:
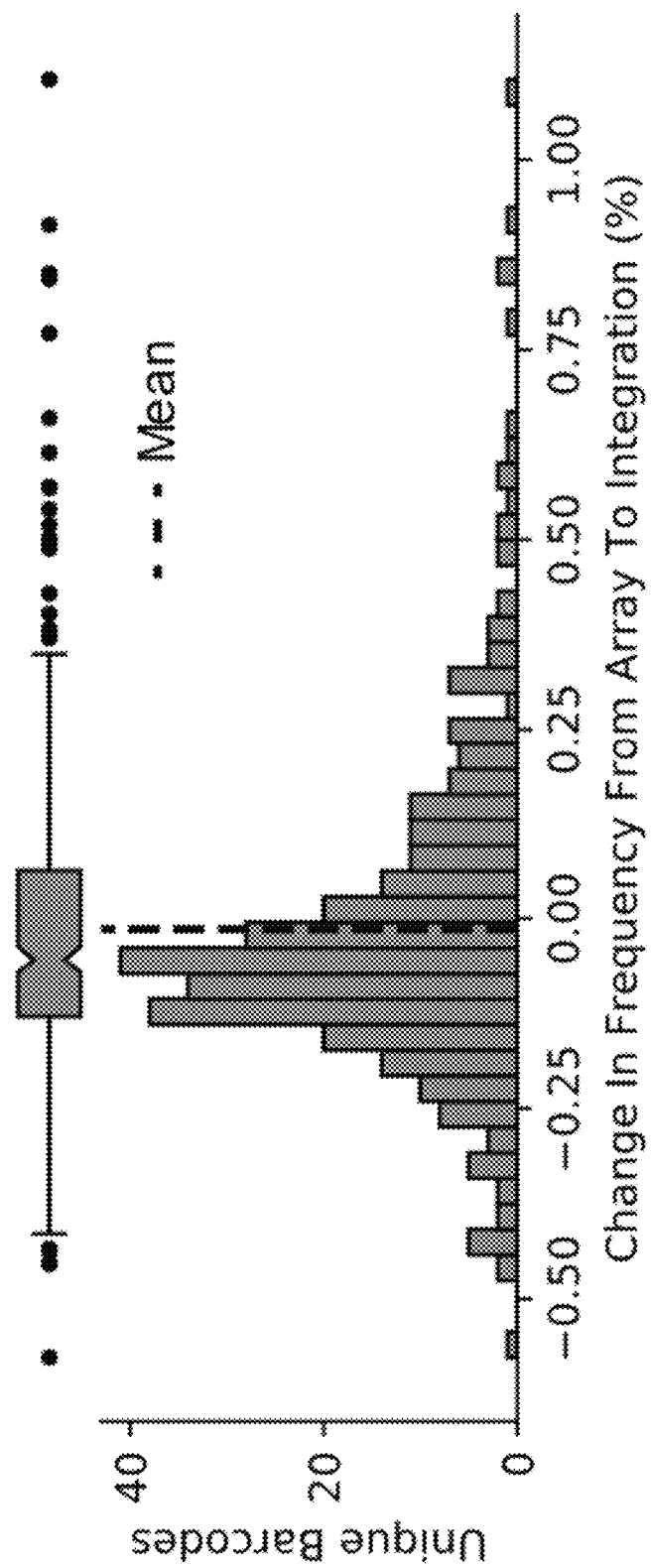
FIG. 9 is a histogram showing the number of unique index sequences ("barcodes") as a function of the change in frequency observed from the PX742 array to integrated population.

Integration Bias Checking Results. There was an approximately normal distribution of reads from the array to the integrated population (FIG. 9). In total, 331 independent lineages were identified. The majority of reads indicated a less than 0.5% change in frequency from the array. In this preliminary experiment, no designs were present to remove PCR jackpotting, thus any change in frequency from the array is likely an overestimate of bias. As a result, it appears that the process of integration exhibits little to no bias.

Figure 10:
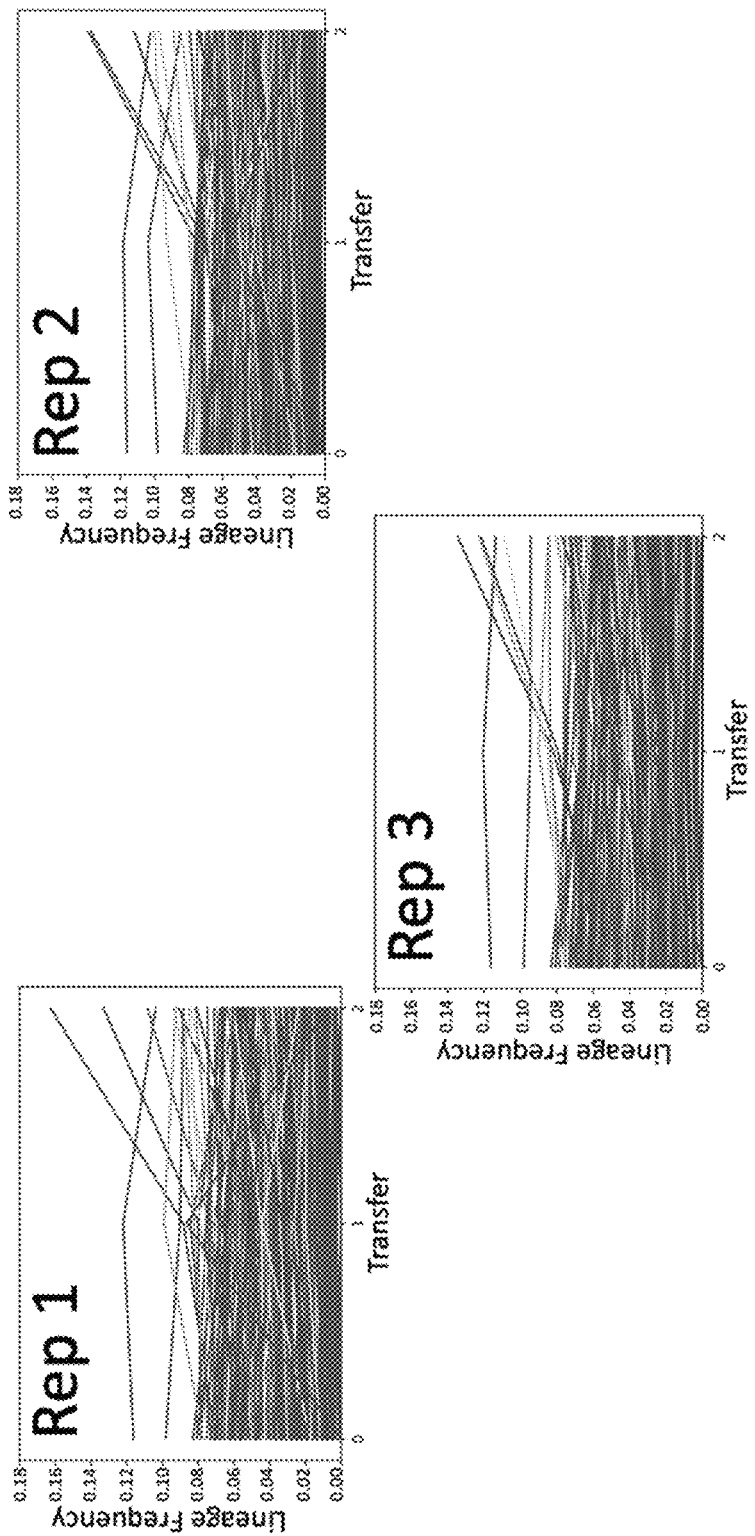
FIG. 10 shows line charts of lineage frequency as a function of transfer number observed in three independent replicates.
Figure 11:
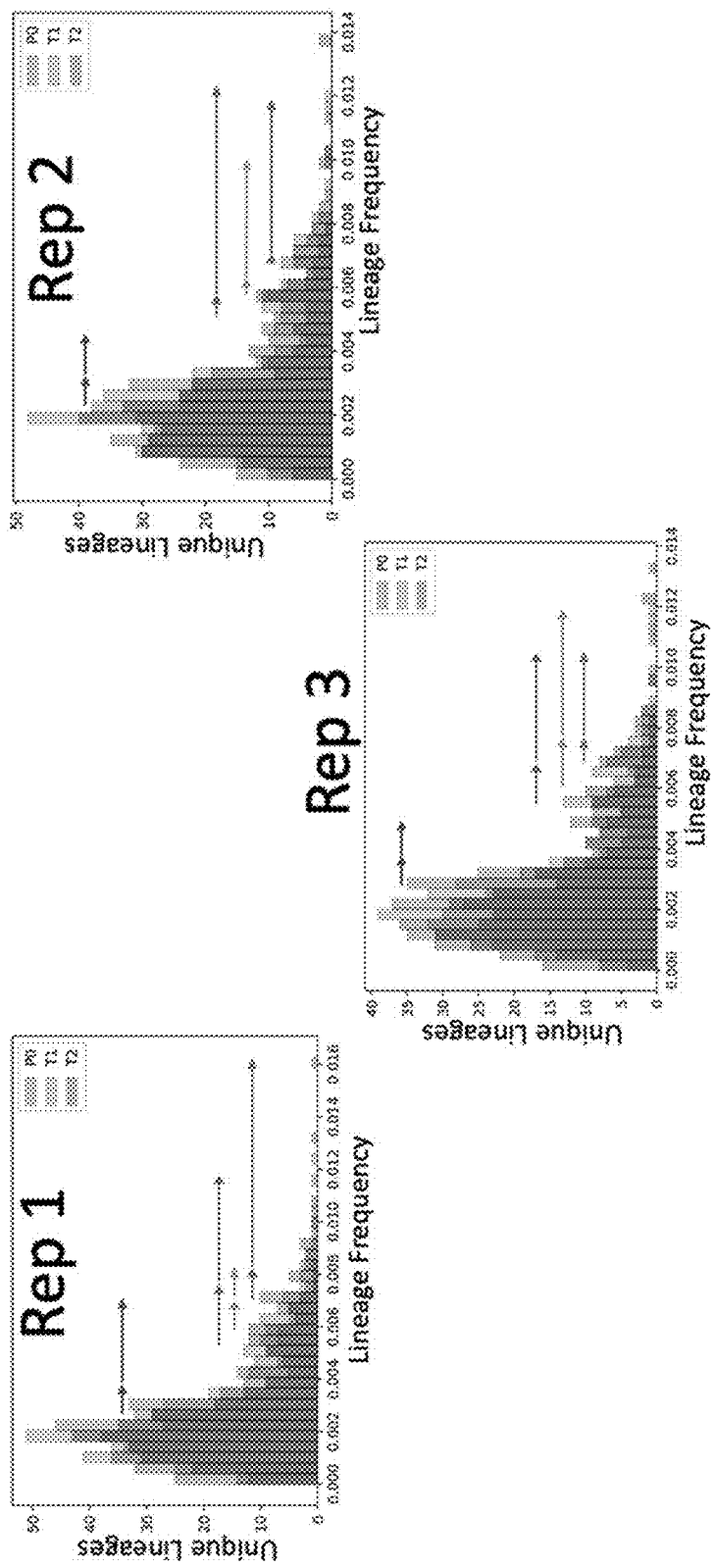
FIG. 11 illustrates histograms showing the change in frequency across unique lineages from the PX742 array to the integrated population observed in three independent replicates. Marked with arrows are the four lineages which increased the most from the P0.

Lineage Trajectory Results. Of the three replicates, each of them behaved similarly. Evolutionary drift would predict that lineages without strongly positive or negative selective pressure would change in frequency at random. Of the 331 lineages traced, four showed increased frequency, suggestive of positive selection (FIG. 10), while the majority of lineages decreased in frequency. When looking at the distribution of lineages frequencies, an increase in the spread of lineage frequencies was seen from the P0 distribution to the first transfer T1 across the three transfers and consistently across the three replicates, and again an increase in spread to T2, consistent with evolutionary drift (FIG. 11). Notably, the trajectories are not identical, and there is variation across the selective benefit of the lineages. With the best performing lineages varying as much as a few percentages from replicate to replicate.

Figure 12:
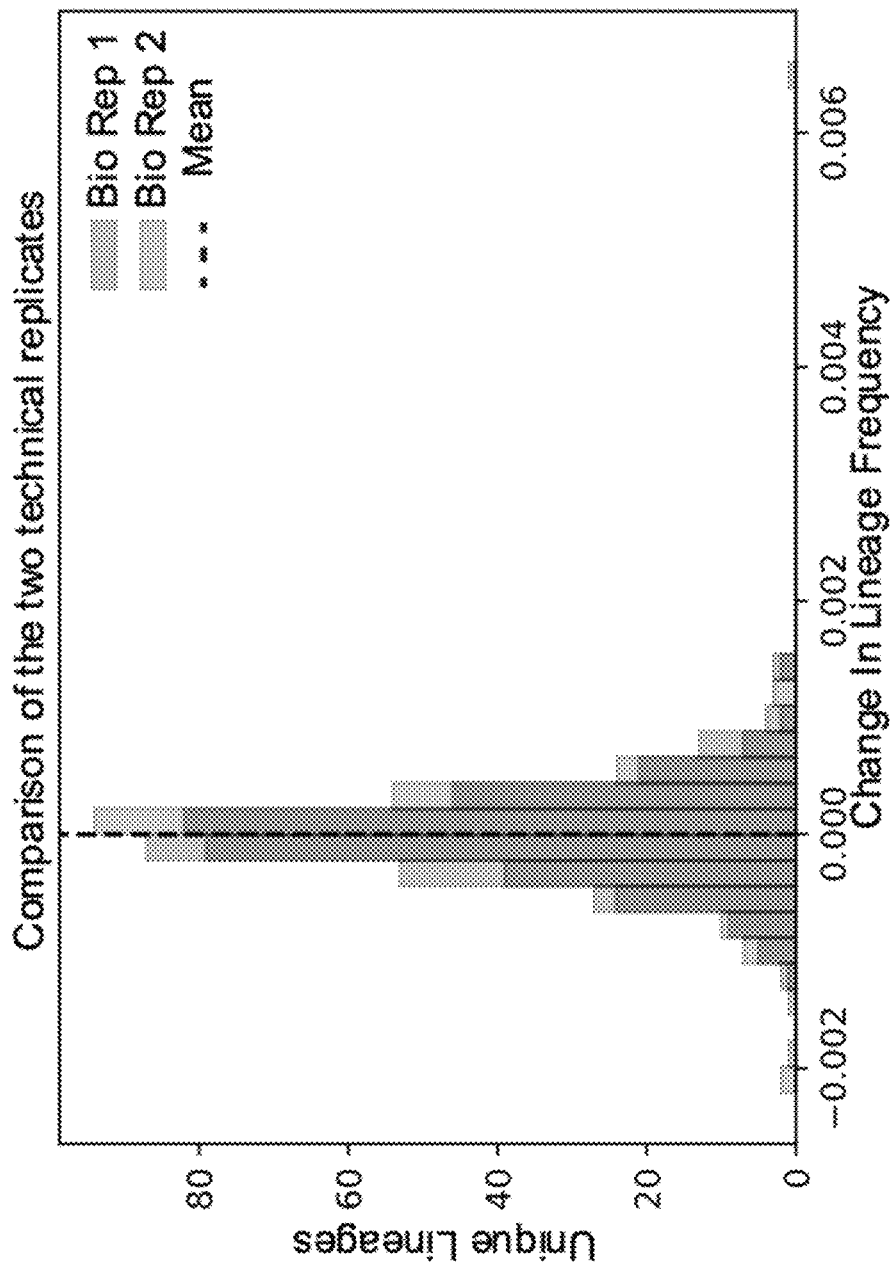
FIG. 12 shows a lineage histogram showing the change in frequency across unique lineages for two independent PCR replicates, compared for a difference in frequency.

PCR jackpotting may significantly and artificially alter the frequency of a lineage. Molecular identifiers can solve this problem: Two independent PCR replicates were compared for a difference in frequency (FIG. 12). Again, a spread in frequencies increased from the P0 distribution to the first transfer T1, and again an increase in spread to T2, consistent with evolutionary drift. On average the variation between replicates was strikingly low, with the majority being less than 0.2% different (FIG. 12). Therefore, the changes in lineage frequencies are most likely not due to artificial increases or decreased from the PCR protocol.

In view of the many possible embodiments to which the principles of the disclosure may be applied, it should be recognized that the illustrated embodiments are only examples and should not be taken as limiting the scope of the invention. Rather, the scope of the invention is defined by the following claims. We therefore claim as our invention all that comes within the scope and spirit of these claims.

We claim:

1. A method of producing a plurality of genetically modified multi-cellular organisms, comprising:
   injecting a nucleic acid molecule comprising a plurality of index sequences into a cell of a single multi-cellular organism, the cell comprising a genomic polynucleotide comprising a synthetic landing pad, to produce a cell comprising the genomic polynucleotide comprising the synthetic landing pad and the nucleic acid molecule comprising the plurality of index sequences, wherein each of the plurality of index sequences comprises a first portion of a nucleotide sequence and is flanked by homology arms, and the synthetic landing pad comprises a second portion of the nucleotide sequence;
   generating a plurality of progeny multi-cellular organisms from the multi-cellular organism, wherein each of the plurality of progeny multi-cellular organisms comprises the genomic polynucleotide comprising the synthetic landing pad and the nucleic acid molecule comprising the plurality of index sequences;
   integrating a single index sequence of the plurality of index sequences into the synthetic landing pad in each of the plurality of progeny multi-cellular organisms, thereby linking the first and second portions of the nucleotide sequence; and
   selecting progeny multi-cellular organisms each comprising a single integrated index sequence based on presence or activity of the linked first and second portions of the nucleotide sequence, thereby producing a plurality of genetically modified multi-cellular organisms wherein the multi-cellular organism is *C. elegans*.

2. The method of claim 1, wherein the nucleic acid molecule comprising the plurality of index sequences comprises 500-3,000 index sequences.

3. The method of claim 1, wherein the first portion and the second portion of the nucleotide sequence reconstitute a functional gene when linked.

4. The method of claim 3, wherein the functional gene is a selectable marker or reporter gene.

5. The method of claim 3, wherein the synthetic landing pad further comprises a site-specific nuclease (SSN) recognition site and homology arms flanking the SSN recognition site, wherein the homology arms flanking the SSN recognition site are the same as the homology arms flanking the first portion of a nucleotide sequence in each of the plurality of index sequences.

6. The method of claim 5, wherein each of the homology arms is 150-500 nucleotides in length.

7. The method of claim 5, wherein integrating the single index sequence into the synthetic landing pad comprises introducing a DNA break at the SSN recognition site utilizing the SSN, and site-specific integration of the single index sequence into the synthetic landing pad.

8. The method of claim 7, wherein the SSN is a Cas, zinc-finger nuclease, or TALEN.

9. The method of claim 1, wherein the nucleic acid molecule comprising the plurality of index sequences is an extrachromosomal array, a plasmid, or an artificial chromosome.

10. The method of claim 1, wherein each of the plurality of index sequences comprises a homologous fragment of the genomic polynucleotide, and wherein each of the plurality of index sequences are different.

11. The method of claim 10, wherein the genomic polynucleotide is an intron or exon of a gene, or a promoter element.

12. The method of claim 1, wherein the lineage of the multi-cellular organism is traced by detecting an index sequence in a progeny multi-cellular organism of the plurality of progeny multi-cellular organisms, or in a genetically modified multi-cellular organism of the plurality of genetically modified multi-cellular organisms.

13. The method of claim 1, wherein each of the plurality of index sequences comprises a sequence variant of a reference coding sequence, a sequence variant of a reference non-coding sequence, a library sequence, a randomized sequence, or a promoter element.

14. The method of claim 13, further comprising:
selecting a single sequence variant of the reference coding sequence by selecting a genetically modified multi-cellular organism comprising the reference coding sequence variant;
selecting a single sequence variant of the reference non-coding sequence by selecting a genetically modified multi-cellular organism comprising the reference non-coding sequence variant;
selecting a single library sequence by selecting a genetically modified multi-cellular organism comprising the library sequence;
selecting a single randomized sequence by selecting a genetically modified multi-cellular organism comprising the randomized sequence; or
selecting a single promoter element by selecting a genetically modified multi-cellular organism comprising a screenable marker or reporter gene operably linked to the promoter element in the genomic polynucleotide wherein the multi-cellular organism is *C. elegans*.

15. The method of claim 1, further comprising:
selecting a genetically modified multi-cellular organism comprising an index sequence by an assay phenotype, or by expression of a selectable marker or reporter;
generating variants of the index sequence;
introducing a nucleic acid molecule comprising the variants of the index sequence into a cell of a single multi-cellular organism, the cell comprising a genomic polynucleotide comprising a synthetic landing pad, to produce a cell comprising the genomic polynucleotide comprising the synthetic landing pad and the nucleic acid molecule comprising the variants of the index sequence, wherein each of the variants of the index sequence comprises a first portion of a nucleotide sequence and the synthetic landing pad comprises a second portion of the nucleotide sequence;
generating a plurality of progeny multi-cellular organisms from the multi-cellular organism, wherein each of the plurality of progeny multi-cellular organisms comprises the genomic polynucleotide comprising the synthetic landing pad and the nucleic acid molecule comprising the variants of the index sequence;
integrating a single variant of the variants of the index sequences into the synthetic landing pad in each of the plurality of progeny multi-cellular organisms, thereby linking the first and second portions of the nucleotide sequence; and
selecting progeny multi-cellular organisms each comprising a single integrated variant of the index sequence based on presence or activity of the linked first and second portions of the nucleotide sequence wherein the multi-cellular organism is *C. elegans*.

* * * * *